US011376040B2

(12) United States Patent
Kalina, Jr. et al.

(10) Patent No.: US 11,376,040 B2
(45) Date of Patent: Jul. 5, 2022

(54) SYSTEMS AND METHODS FOR DELIVERING MULTIPLE OCULAR IMPLANTS

(71) Applicant: GLAUKOS CORPORATION, San Clemente, CA (US)

(72) Inventors: Charles Raymond Kalina, Jr., Irvine, CA (US); Todd N. Fjield, Irvine, CA (US); Douglas Daniel Crimaldi, San Marcos, CA (US); Emma Claire Benjaminson, Laguna Hills, CA (US); Tyler Joseph Brown, Dana Point, CA (US); Richard William Martin, San Marcos, CA (US)

(73) Assignee: Glaukos Corporation, San Clemente, CA (US)

( * ) Notice: Subject to any disclaimer, the term of this patent is extended or adjusted under 35 U.S.C. 154(b) by 823 days.

(21) Appl. No.: 16/132,252

(22) Filed: Sep. 14, 2018

(65) Prior Publication Data

US 2019/0105077 A1 Apr. 11, 2019

Related U.S. Application Data

(60) Provisional application No. 62/671,286, filed on May 14, 2018, provisional application No. 62/578,273,
(Continued)

(51) Int. Cl.
*A61F 9/007* (2006.01)
*A61F 9/00* (2006.01)
(Continued)

(52) U.S. Cl.
CPC .......... *A61B 17/3468* (2013.01); *A61F 9/007* (2013.01); *A61F 9/0017* (2013.01);
(Continued)

(58) Field of Classification Search
CPC ....... A61B 17/3468; A61B 2017/00367; A61F 9/0017; A61F 9/007; A61F 9/00781; A61F 2250/0064
See application file for complete search history.

(56) References Cited

U.S. PATENT DOCUMENTS

| 2,269,963 A | 1/1942 | Frederick |
| 3,416,530 A | 12/1968 | Ness |
| (Continued) | | |

FOREIGN PATENT DOCUMENTS

| AU | 200072059 | 12/2000 |
| CA | 2273331 | 6/1998 |
| (Continued) | | |

OTHER PUBLICATIONS

Bucciarelli, Patrice D., "Working Model is Next Step in Team's Long Journey to Commercial Product", Healthfirst, Business First of Louisville, louisville.bizjournals.com, Feb. 27, 2004.
(Continued)

*Primary Examiner* — Benjamin J Klein
(74) *Attorney, Agent, or Firm* — Knobbe Martens Olson & Bear LLP

(57) ABSTRACT

Systems and methods for delivering multiple ocular implants to reduce intraocular pressure are disclosed. The ocular implants can be implanted at multiple sites within a single human eye without requiring removal of the delivery apparatus from the eye. A system for delivering multiple ocular implants can include a plurality of implants, an external housing, and an introducer assembly. The external housing can provide access to an implant singulation actuator and an implant delivery actuator. The introducer assembly can comprise an auto-retracting introducer portion. The
(Continued)

delivery apparatus can include an infinite activation mechanism/portion and/or a manual singulation mechanism/portion.

20 Claims, 40 Drawing Sheets

Related U.S. Application Data filed on Oct. 27, 2017, provisional application No. 62/569,458, filed on Oct. 6, 2017.

(51) Int. Cl.
  *A61B 17/34* (2006.01)
  *A61B 17/00* (2006.01)
(52) U.S. Cl.
  CPC .............. *A61F 9/00781* (2013.01); *A61B 2017/00367* (2013.01); *A61F 2250/0064* (2013.01)

(56) References Cited

U.S. PATENT DOCUMENTS

| | | | |
|---|---|---|---|
| 3,439,675 A | 4/1969 | Cohen |
| 3,948,271 A | 4/1976 | Aklyama |
| 3,948,871 A | 4/1976 | Butterfield et al. |
| 3,976,077 A | 8/1976 | Kerfoot, Jr. |
| 4,113,088 A | 9/1978 | Binkhorst |
| 4,299,227 A | 11/1981 | Lincoff |
| 4,366,582 A | 1/1983 | Faulkner |
| 4,449,529 A | 5/1984 | Burns et al. |
| 4,501,274 A | 2/1985 | Skjaerpe |
| 4,560,383 A | 12/1985 | Leiske |
| 4,578,058 A | 3/1986 | Grandon |
| 4,634,418 A | 1/1987 | Binder |
| 4,642,090 A | 2/1987 | Ultrata |
| 4,782,819 A | 11/1988 | Adair |
| 4,800,870 A | 1/1989 | Reid, Jr. |
| 4,800,890 A | 1/1989 | Cramer |
| 4,846,172 A | 7/1989 | Berlin |
| 4,846,793 A | 7/1989 | Leonard et al. |
| 4,867,173 A | 9/1989 | Leoni |
| 4,870,953 A | 10/1989 | DonMichael et al. |
| 4,900,300 A | 2/1990 | Lee |
| 4,905,667 A | 3/1990 | Foerster et al. |
| 4,991,602 A | 2/1991 | Amplatz et al. |
| 5,053,040 A | 10/1991 | Goldsmith, III |
| 5,053,044 A | 10/1991 | Mueller et al. |
| 5,095,887 A | 3/1992 | Leon et al. |
| 5,129,895 A | 7/1992 | Vassiliadis et al. |
| 5,169,386 A | 12/1992 | Becker et al. |
| 5,180,362 A | 1/1993 | Worst |
| 5,207,685 A | 5/1993 | Cinberg et al. |
| 5,221,255 A | 6/1993 | Mahurkar et al. |
| 5,246,451 A | 9/1993 | Trescony et al. |
| 5,284,476 A | 2/1994 | Koch |
| 5,290,295 A | 3/1994 | Querals et al. |
| 5,324,306 A | 6/1994 | Makower et al. |
| 5,342,370 A | 8/1994 | Simon et al. |
| 5,360,399 A | 11/1994 | Stegmann |
| 5,409,457 A | 4/1995 | del Cerro et al. |
| 5,415,666 A | 5/1995 | Gourlay et al. |
| 5,423,330 A | 6/1995 | Lee |
| 5,445,637 A | 8/1995 | Bretton |
| 5,462,558 A | 10/1995 | Kolesa et al. |
| 5,472,440 A | 12/1995 | Beckman |
| 5,486,165 A | 1/1996 | Stegmann |
| 5,556,400 A | 9/1996 | Tunis |
| 5,558,637 A | 9/1996 | Allonen et al. |
| 5,626,588 A | 5/1997 | Sauer et al. |
| 5,643,321 A | 7/1997 | McDevitt |
| 5,651,782 A | 7/1997 | Simon et al. |
| 5,651,783 A | 7/1997 | Reynard |
| 5,653,724 A | 8/1997 | Imonti |
| 5,669,501 A | 9/1997 | Hissong et al. |
| 5,676,679 A | 10/1997 | Simon et al. |
| 5,681,323 A | 10/1997 | Arick |
| 5,695,479 A | 12/1997 | Jagpal |
| 5,702,414 A | 12/1997 | Richter et al. |
| 5,702,419 A | 12/1997 | Berry et al. |
| 5,725,546 A | 3/1998 | Samson |
| 5,733,256 A | 3/1998 | Costin |
| 5,741,282 A | 4/1998 | Anspach, III et al. |
| 5,741,292 A | 4/1998 | Mendius |
| 5,762,625 A | 6/1998 | Igaki |
| 5,792,099 A | 8/1998 | DeCamp et al. |
| 5,807,244 A | 9/1998 | Barot |
| 5,817,100 A | 10/1998 | Igaki |
| 5,833,694 A | 11/1998 | Poncet |
| 5,836,939 A | 11/1998 | Negus et al. |
| D402,757 S | 12/1998 | Davis et al. |
| 5,846,199 A | 12/1998 | Hijlkema et al. |
| 5,865,831 A | 2/1999 | Cozean et al. |
| 5,868,697 A | 2/1999 | Ritcher et al. |
| 5,891,084 A | 4/1999 | Lee |
| 5,893,837 A | 4/1999 | Eagles et al. |
| 5,927,585 A | 7/1999 | Moorman et al. |
| 5,941,250 A | 8/1999 | Aramant et al. |
| 5,984,913 A | 11/1999 | Kritzinger et al. |
| 6,004,302 A | 12/1999 | Brierley |
| 6,030,416 A | 2/2000 | Huo et al. |
| 6,036,678 A | 3/2000 | Giungo |
| 6,036,682 A | 3/2000 | Lange et al. |
| 6,045,557 A | 4/2000 | White et al. |
| 6,050,999 A | 4/2000 | Paraschac et al. |
| 6,071,286 A | 6/2000 | Mawad |
| 6,074,395 A | 6/2000 | Trott et al. |
| 6,135,977 A | 10/2000 | Drasler et al. |
| 6,142,990 A | 11/2000 | Burk |
| 6,146,387 A | 11/2000 | Trott et al. |
| 6,187,016 B1 | 2/2001 | Hedges et al. |
| 6,203,513 B1 | 3/2001 | Yaron et al. |
| 6,221,078 B1 | 4/2001 | Bylsma |
| 6,224,570 B1 | 5/2001 | Le et al. |
| 6,254,612 B1 | 7/2001 | Hieshima |
| 6,264,668 B1 | 7/2001 | Prywes |
| 6,287,313 B1 | 9/2001 | Sasso |
| 6,299,603 B1 | 10/2001 | Hecker et al. |
| 6,342,058 B1 | 1/2002 | Portney |
| 6,355,033 B1 | 3/2002 | Moorman et al. |
| 6,361,519 B1 | 3/2002 | Knudson et al. |
| 6,363,938 B2 | 4/2002 | Saadat |
| 6,375,642 B1 | 4/2002 | Grieshaber et al. |
| 6,378,526 B1 | 4/2002 | Bowman et al. |
| 6,402,734 B1 | 6/2002 | Weiss |
| 6,405,732 B1 | 6/2002 | Edwards et al. |
| 6,428,501 B1 | 8/2002 | Reynard |
| 6,428,566 B1 | 8/2002 | Holt |
| 6,450,937 B1 | 9/2002 | Mercereau et al. |
| 6,450,984 B1 | 9/2002 | Lynch et al. |
| 6,454,787 B1 | 9/2002 | Maddalo et al. |
| 6,464,724 B1 | 10/2002 | Lynch et al. |
| 6,524,275 B1 | 2/2003 | Lynch et al. |
| 6,530,896 B1 | 3/2003 | Elliott |
| 6,544,249 B1 | 4/2003 | Yu et al. |
| 6,582,426 B2 | 6/2003 | Moorman et al. |
| 6,585,680 B2 | 7/2003 | Bugge |
| 6,589,203 B1 | 7/2003 | Mitrev |
| 6,607,542 B1 | 8/2003 | Wild |
| 6,613,343 B2 | 9/2003 | Dillingham et al. |
| 6,620,154 B1 | 9/2003 | Amirkhanian et al. |
| 6,626,858 B2 | 9/2003 | Lynch et al. |
| 6,629,981 B2 | 10/2003 | Bui et al. |
| 6,638,239 B1 | 10/2003 | Bergheim et al. |
| 6,666,841 B2 | 12/2003 | Gharib et al. |
| 6,676,607 B2 | 1/2004 | De Juan, Jr. et al. |
| 6,699,272 B2 | 3/2004 | Slepian et al. |
| 6,726,676 B2 | 4/2004 | Stegmann et al. |
| D490,152 S | 5/2004 | Myall et al. |
| 6,730,056 B1 | 5/2004 | Ghaem et al. |
| 6,736,791 B1 | 5/2004 | Tu et al. |
| 6,763,833 B1 | 7/2004 | Khera et al. |
| 6,764,439 B2 | 7/2004 | Schaaf et al. |

(56) References Cited

U.S. PATENT DOCUMENTS

| | | |
|---|---|---|
| 6,767,346 B2 | 7/2004 | Damasco et al. |
| 6,780,164 B2 | 8/2004 | Bergheim et al. |
| 6,780,165 B2 | 8/2004 | Kadziauskas et al. |
| 6,783,544 B2 | 8/2004 | Lynch et al. |
| 6,827,699 B2 | 12/2004 | Lynch et al. |
| 6,827,700 B2 | 12/2004 | Lynch et al. |
| 6,827,738 B2 | 12/2004 | Willis et al. |
| 6,902,577 B2 | 6/2005 | Lipshitz et al. |
| 6,939,298 B2 | 9/2005 | Brown et al. |
| 6,955,656 B2 | 10/2005 | Bergheim et al. |
| 6,966,888 B2 | 11/2005 | Cullen |
| 6,969,384 B2 | 11/2005 | De Juan, Jr. et al. |
| 6,981,958 B1 | 1/2006 | Gharib et al. |
| 7,077,821 B2 | 7/2006 | Durgin |
| 7,077,848 B1 | 7/2006 | de Juan et al. |
| 7,090,681 B2 | 8/2006 | Weber et al. |
| 7,094,225 B2 | 8/2006 | Tu et al. |
| 7,135,009 B2 | 11/2006 | Tu et al. |
| 7,135,016 B1 | 11/2006 | Asia et al. |
| 7,163,543 B2 | 1/2007 | Smedley et al. |
| 7,186,232 B1 | 3/2007 | Smedley et al. |
| 7,192,412 B1 | 3/2007 | Zhou et al. |
| 7,217,263 B2 | 5/2007 | Humayun et al. |
| 7,220,238 B2 | 5/2007 | Lynch et al. |
| 7,273,475 B2 | 9/2007 | Tu et al. |
| 7,297,130 B2 | 11/2007 | Bergheim et al. |
| 7,331,984 B2 | 2/2008 | Tu et al. |
| 7,344,528 B1 | 3/2008 | Tu et al. |
| 7,431,710 B2 | 10/2008 | Tu et al. |
| 7,468,065 B2 | 12/2008 | Weber et al. |
| 7,488,303 B1 | 2/2009 | Haffner et al. |
| 7,520,876 B2 | 4/2009 | Reesemann et al. |
| D592,746 S | 5/2009 | Highley et al. |
| 7,563,241 B2 | 7/2009 | Tu et al. |
| D606,190 S | 12/2009 | Pruitt et al. |
| 7,678,065 B2 | 3/2010 | Haffner et al. |
| 7,708,711 B2 | 5/2010 | Tu et al. |
| 7,713,228 B2 | 5/2010 | Robin |
| 7,758,624 B2 | 7/2010 | Dorn et al. |
| 7,771,388 B2 | 8/2010 | Olsen et al. |
| 7,850,637 B2 | 12/2010 | Lynch et al. |
| 7,857,782 B2 | 12/2010 | Tu et al. |
| 7,867,186 B2 | 1/2011 | Haffner et al. |
| 7,867,205 B2 | 1/2011 | Bergheim et al. |
| 7,879,001 B2 | 2/2011 | Haffner et al. |
| 7,879,079 B2 | 2/2011 | Tu et al. |
| 7,905,904 B2 | 3/2011 | Stone et al. |
| 7,931,660 B2 | 4/2011 | Aranyi et al. |
| 7,945,336 B2 | 5/2011 | Sauter/Starace et al. |
| 7,951,155 B2 | 5/2011 | Smedley et al. |
| 7,959,632 B2 | 6/2011 | Fugo |
| 7,967,772 B2 | 6/2011 | McKenzie et al. |
| 8,007,459 B2 | 8/2011 | Haffner et al. |
| D645,489 S | 9/2011 | Gille et al. |
| D645,490 S | 9/2011 | Gille et al. |
| 8,062,244 B2 | 11/2011 | Tu et al. |
| 8,070,290 B2 | 12/2011 | Gille et al. |
| 8,075,511 B2 | 12/2011 | Tu et al. |
| 8,118,768 B2 | 2/2012 | Tu et al. |
| 8,142,364 B2 | 3/2012 | Haffner et al. |
| 8,152,752 B2 | 4/2012 | Lynch et al. |
| 8,197,418 B2 | 6/2012 | Lal et al. |
| 8,267,882 B2 | 9/2012 | Euteneuer et al. |
| 8,273,050 B2 | 9/2012 | Bergheim et al. |
| 8,307,701 B2 | 11/2012 | Laricchiuta |
| 8,333,742 B2 | 12/2012 | Bergheim et al. |
| 8,337,445 B2 | 12/2012 | Tu et al. |
| 8,348,877 B2 | 1/2013 | Tu et al. |
| 8,388,568 B2 | 3/2013 | Lynch et al. |
| 8,506,515 B2 | 8/2013 | Burns et al. |
| 8,540,659 B2 | 9/2013 | Berlin |
| 8,579,846 B2 | 11/2013 | Tu et al. |
| 8,617,094 B2 | 12/2013 | Smedley et al. |
| 8,679,089 B2 | 3/2014 | Berlin |
| 8,771,217 B2 | 7/2014 | Lynch et al. |
| 8,801,648 B2 | 8/2014 | Bergheim et al. |
| 8,801,649 B2 | 8/2014 | De Juan, Jr. et al. |
| 8,808,219 B2 | 8/2014 | Bergheim et al. |
| 8,814,820 B2 | 8/2014 | Bergheim et al. |
| 8,852,137 B2 | 10/2014 | Horvath et al. |
| 8,852,266 B2 | 10/2014 | Brooks et al. |
| 8,882,781 B2 | 11/2014 | Smedley et al. |
| 8,998,983 B2 | 4/2015 | Auld |
| 9,066,782 B2 | 6/2015 | Tu et al. |
| 9,155,654 B2 | 10/2015 | Tu et al. |
| 9,155,656 B2 | 10/2015 | Schaller et al. |
| 9,173,775 B2 | 11/2015 | Haffner et al. |
| 9,220,632 B2 | 12/2015 | Smedley et al. |
| 9,301,875 B2 | 4/2016 | Tu et al. |
| 9,492,320 B2 | 11/2016 | Lynch et al. |
| 9,554,940 B2 | 1/2017 | Haffner et al. |
| 9,561,131 B2 | 2/2017 | Tu et al. |
| 9,572,963 B2 | 2/2017 | Tu et al. |
| 9,592,151 B2 | 3/2017 | Rangel-Friedman et al. |
| 9,597,230 B2 | 3/2017 | Haffner et al. |
| 9,603,738 B2 | 3/2017 | Haffner et al. |
| 9,636,255 B2 | 5/2017 | Haffner et al. |
| 9,668,915 B2 | 6/2017 | Haffner et al. |
| 9,693,899 B2 | 7/2017 | Wardle et al. |
| 9,730,638 B2 | 8/2017 | Haffner et al. |
| 9,789,001 B2 | 10/2017 | Tu et al. |
| 9,827,143 B2 | 11/2017 | Lynch et al. |
| 9,849,027 B2 | 12/2017 | Highley et al. |
| 9,962,290 B2 | 5/2018 | Burns et al. |
| 9,987,472 B2 | 6/2018 | Tu et al. |
| 9,993,368 B2 | 6/2018 | Bergheim et al. |
| D833,008 S | 11/2018 | Kalina, Jr. et al. |
| 10,159,601 B2 | 12/2018 | Berlin |
| 10,188,551 B2 | 1/2019 | Rangel-Friedman et al. |
| 10,206,813 B2 | 2/2019 | Haffner et al. |
| D846,738 S | 4/2019 | Kalina, Jr. et al. |
| 10,245,178 B1 | 4/2019 | Heitzmann et al. |
| 10,271,989 B2 | 4/2019 | Haffner et al. |
| 10,285,853 B2 | 5/2019 | Rangel-Friedman et al. |
| 10,285,856 B2 | 5/2019 | Tu et al. |
| 10,406,029 B2 | 9/2019 | Tu et al. |
| 10,485,701 B2 | 11/2019 | Haffner et al. |
| 10,485,702 B2 | 11/2019 | Bergheim et al. |
| 10,492,950 B2 | 12/2019 | Lynch et al. |
| 10,499,809 B2 | 12/2019 | Kalina, Jr. et al. |
| 10,517,759 B2 | 12/2019 | Crimaldi et al. |
| 10,568,762 B2 | 2/2020 | Lynch et al. |
| D886,997 S | 6/2020 | Kalina, Jr. et al. |
| 10,674,906 B2 | 6/2020 | Kalina, Jr. et al. |
| 10,780,218 B2 | 9/2020 | Novakovic et al. |
| 10,813,789 B2 | 10/2020 | Haffner et al. |
| D901,683 S | 11/2020 | Kalina, Jr. et al. |
| 10,828,195 B2 | 11/2020 | Burns et al. |
| 10,828,473 B2 | 11/2020 | Haffner et al. |
| 10,959,941 B2 | 3/2021 | Haffner |
| 11,019,996 B2 | 6/2021 | Kalina, Jr. et al. |
| 11,019,997 B2 | 6/2021 | Kalina, Jr. et al. |
| 11,116,625 B2 | 9/2021 | Kalina, Jr. |
| D938,585 S | 12/2021 | Kalina, Jr. et al. |
| 11,197,780 B2 | 12/2021 | Haffner et al. |
| 2001/0000527 A1 | 4/2001 | Yaron et al. |
| 2001/0025150 A1 | 9/2001 | de Juan et al. |
| 2002/0052640 A1 | 5/2002 | Bigus et al. |
| 2002/0072673 A1 | 6/2002 | Yamamoto et al. |
| 2002/0111608 A1 | 8/2002 | Baerveldt et al. |
| 2002/0120284 A1 | 8/2002 | Schachar et al. |
| 2002/0120285 A1 | 8/2002 | Schachar et al. |
| 2002/0133168 A1 | 9/2002 | Smedley et al. |
| 2002/0143284 A1 | 10/2002 | Tu et al. |
| 2002/0165522 A1 | 11/2002 | Holmen |
| 2002/0177856 A1 | 11/2002 | Richter et al. |
| 2003/0014021 A1 | 1/2003 | Holmen |
| 2003/0014092 A1 | 1/2003 | Neuhann |
| 2003/0055372 A1 | 3/2003 | Lynch et al. |
| 2003/0060752 A1 | 3/2003 | Bergheim et al. |
| 2003/0074008 A1 | 4/2003 | Ou |
| 2003/0079329 A1 | 5/2003 | Yaron et al. |
| 2003/0093084 A1 | 5/2003 | Nissan et al. |
| 2003/0097117 A1 | 5/2003 | Buono |

(56) References Cited

U.S. PATENT DOCUMENTS

| | | |
|---|---|---|
| 2003/0097151 A1 | 5/2003 | Smedley et al. |
| 2003/0105456 A1 | 6/2003 | Lin |
| 2003/0109907 A1 | 6/2003 | Shadduck |
| 2003/0135149 A1 | 7/2003 | Cullen et al. |
| 2003/0139729 A1 | 7/2003 | Stegmann et al. |
| 2003/0181848 A1 | 9/2003 | Bergheim et al. |
| 2003/0187384 A1 | 10/2003 | Bergheim et al. |
| 2003/0195438 A1 | 10/2003 | Petillo |
| 2003/0208217 A1 | 11/2003 | Dan |
| 2003/0212383 A1 | 11/2003 | Cote et al. |
| 2003/0229303 A1 | 12/2003 | Haffner et al. |
| 2003/0236484 A1 | 12/2003 | Lynch et al. |
| 2004/0024345 A1 | 2/2004 | Gharib et al. |
| 2004/0088048 A1 | 5/2004 | Richter et al. |
| 2004/0098122 A1 | 5/2004 | Lee et al. |
| 2004/0102729 A1 | 5/2004 | Haffner et al. |
| 2004/0111050 A1 | 6/2004 | Smedley et al. |
| 2004/0147870 A1 | 7/2004 | Burns et al. |
| 2004/0154946 A1 | 8/2004 | Solovay et al. |
| 2004/0210185 A1 | 10/2004 | Tu et al. |
| 2004/0216749 A1 | 11/2004 | Tu |
| 2004/0236343 A1 | 11/2004 | Taylor et al. |
| 2004/0243227 A1 | 12/2004 | Starksen et al. |
| 2004/0249404 A1 | 12/2004 | Haefliger |
| 2004/0254517 A1 | 12/2004 | Quiroz/Mercado et al. |
| 2004/0254519 A1 | 12/2004 | Tu et al. |
| 2004/0254520 A1 | 12/2004 | Porteous et al. |
| 2004/0260228 A1 | 12/2004 | Lynch et al. |
| 2005/0049578 A1 | 3/2005 | Tu et al. |
| 2005/0096639 A1 | 5/2005 | Slatkine et al. |
| 2005/0125003 A1 | 6/2005 | Pinchuk et al. |
| 2005/0165385 A1 | 7/2005 | Simon |
| 2005/0171562 A1 | 8/2005 | Criscuolo et al. |
| 2005/0209549 A1 | 9/2005 | Bergheim et al. |
| 2005/0209672 A1 | 9/2005 | George et al. |
| 2005/0240222 A1 | 10/2005 | Shipp |
| 2005/0250788 A1 | 11/2005 | Tu et al. |
| 2005/0266047 A1 | 12/2005 | Tu et al. |
| 2005/0267478 A1 | 12/2005 | Corradi et al. |
| 2005/0277864 A1 | 12/2005 | Haffner et al. |
| 2005/0288619 A1 | 12/2005 | Gharib et al. |
| 2006/0032507 A1 | 2/2006 | Tu |
| 2006/0074375 A1 | 4/2006 | Bergheim et al. |
| 2006/0084907 A1 | 4/2006 | Bergheim et al. |
| 2006/0106370 A1 | 5/2006 | Baerveldt et al. |
| 2006/0116626 A1 | 6/2006 | Smedley et al. |
| 2006/0155300 A1 | 7/2006 | Stamper et al. |
| 2006/0173397 A1 | 8/2006 | Tu et al. |
| 2006/0195055 A1 | 8/2006 | Bergheim et al. |
| 2006/0195056 A1 | 8/2006 | Bergheim et al. |
| 2006/0200113 A1 | 9/2006 | Haffner et al. |
| 2006/0210605 A1 | 9/2006 | Chang et al. |
| 2006/0217741 A1 | 9/2006 | Ghannoum |
| 2006/0241580 A1 | 10/2006 | Mittelstein et al. |
| 2006/0241749 A1 | 10/2006 | Tu et al. |
| 2007/0021653 A1 | 1/2007 | Hattenbach et al. |
| 2007/0031473 A1 | 2/2007 | Peyman |
| 2007/0073275 A1 | 3/2007 | Conston et al. |
| 2007/0078471 A1 | 4/2007 | Schachar et al. |
| 2007/0088432 A1 | 4/2007 | Solovay et al. |
| 2007/0118065 A1 | 5/2007 | Pinchuk et al. |
| 2007/0118066 A1 | 5/2007 | Pinchuk et al. |
| 2007/0123812 A1 | 5/2007 | Pinchuk et al. |
| 2007/0123919 A1 | 5/2007 | Schachar et al. |
| 2007/0149927 A1 | 6/2007 | Itou et al. |
| 2007/0161981 A1 | 7/2007 | Sanders et al. |
| 2007/0179471 A1 | 8/2007 | Christian et al. |
| 2007/0191863 A1 | 8/2007 | De Juan, Jr. et al. |
| 2007/0276315 A1 | 11/2007 | Haffner |
| 2007/0282244 A1 | 12/2007 | Tu et al. |
| 2007/0282245 A1 | 12/2007 | Tu et al. |
| 2007/0287958 A1 | 12/2007 | McKenzie et al. |
| 2007/0293807 A1 | 12/2007 | Lynch et al. |
| 2007/0293872 A1 | 12/2007 | Peyman |
| 2007/0293873 A1 | 12/2007 | Chang |
| 2008/0027304 A1 | 1/2008 | Pardo et al. |
| 2008/0033351 A1 | 2/2008 | Trogden et al. |
| 2008/0045878 A1 | 2/2008 | Bergheim et al. |
| 2008/0051681 A1 | 2/2008 | Schwartz |
| 2008/0058704 A1 | 3/2008 | Hee et al. |
| 2008/0082078 A1 | 4/2008 | Berlin |
| 2008/0091224 A1 | 4/2008 | Griffis, III et al. |
| 2008/0097214 A1 | 4/2008 | Meyers et al. |
| 2008/0097335 A1 | 4/2008 | Trogden et al. |
| 2008/0108933 A1 | 5/2008 | Yu et al. |
| 2008/0109037 A1 | 5/2008 | Steiner et al. |
| 2008/0114440 A1 | 5/2008 | Hlavka et al. |
| 2008/0125691 A1 | 5/2008 | Yaron et al. |
| 2008/0140059 A1 | 6/2008 | Schachar et al. |
| 2008/0147083 A1 | 6/2008 | Vold et al. |
| 2008/0183289 A1 | 7/2008 | Werblin |
| 2008/0188860 A1 | 8/2008 | Vold |
| 2008/0200860 A1 | 8/2008 | Tu et al. |
| 2008/0200923 A1 | 8/2008 | Beckman et al. |
| 2008/0208176 A1 | 8/2008 | Loh |
| 2008/0215062 A1 | 9/2008 | Bowen et al. |
| 2008/0221501 A1 | 9/2008 | Cote et al. |
| 2008/0228127 A1 | 9/2008 | Burns et al. |
| 2008/0243156 A1 | 10/2008 | John |
| 2008/0255545 A1 | 10/2008 | Mansfield et al. |
| 2008/0269730 A1 | 10/2008 | Dotson |
| 2008/0281250 A1 | 11/2008 | Bergsneider et al. |
| 2008/0306429 A1 | 12/2008 | Shields et al. |
| 2009/0043242 A1 | 2/2009 | Bene et al. |
| 2009/0043321 A1 | 2/2009 | Conston et al. |
| 2009/0043365 A1 | 2/2009 | Friedland et al. |
| 2009/0076436 A2 | 3/2009 | Gharib et al. |
| 2009/0112245 A1 | 4/2009 | Haefliger |
| 2009/0124973 A1 | 5/2009 | D'Agostino et al. |
| 2009/0132040 A1 | 5/2009 | Frion et al. |
| 2009/0137989 A1 | 5/2009 | Kataoka |
| 2009/0182421 A1 | 7/2009 | Silvestrini et al. |
| 2009/0198213 A1 | 8/2009 | Tanaka |
| 2009/0204053 A1 | 8/2009 | Nissan et al. |
| 2009/0227933 A1 | 9/2009 | Karageozian |
| 2009/0227934 A1 | 9/2009 | Euteneuer et al. |
| 2009/0264813 A1 | 10/2009 | Chang |
| 2009/0280158 A1 | 11/2009 | Butuner |
| 2009/0287233 A1 | 11/2009 | Huculak |
| 2010/0004581 A1 | 1/2010 | Brigatti et al. |
| 2010/0010416 A1 | 1/2010 | Juan, Jr. et al. |
| 2010/0010452 A1 | 1/2010 | Paques et al. |
| 2010/0030150 A1 | 2/2010 | Paques et al. |
| 2010/0056979 A1 | 3/2010 | Smedley et al. |
| 2010/0057093 A1 | 3/2010 | Ide et al. |
| 2010/0076419 A1 | 3/2010 | Chew et al. |
| 2010/0121248 A1 | 5/2010 | Yu et al. |
| 2010/0121249 A1 | 5/2010 | Yu et al. |
| 2010/0121342 A1 | 5/2010 | Schieber et al. |
| 2010/0137981 A1 | 6/2010 | Silvestrini et al. |
| 2010/0152626 A1 | 6/2010 | Schwartz |
| 2010/0158980 A1 | 6/2010 | Kopczynski et al. |
| 2010/0173866 A1 | 7/2010 | Hee et al. |
| 2010/0185138 A1 | 7/2010 | Yaron et al. |
| 2010/0185205 A1 | 7/2010 | Novakovic et al. |
| 2010/0191103 A1 | 7/2010 | Stamper et al. |
| 2010/0225061 A1 | 9/2010 | Bath |
| 2010/0240987 A1 | 9/2010 | Christian et al. |
| 2010/0255061 A1 | 10/2010 | de Juan, Jr. et al. |
| 2010/0262174 A1 | 10/2010 | Sretavan |
| 2010/0274258 A1 | 10/2010 | Silvestrini et al. |
| 2010/0278898 A1 | 11/2010 | Hughes et al. |
| 2010/0280317 A1 | 11/2010 | Silvestrini et al. |
| 2011/0009874 A1 | 1/2011 | Wardle et al. |
| 2011/0009958 A1 | 1/2011 | Wardle et al. |
| 2011/0022065 A1 | 1/2011 | Shipp |
| 2011/0028883 A1 | 2/2011 | Juan, Jr. et al. |
| 2011/0028983 A1 | 2/2011 | Silvestrini et al. |
| 2011/0046536 A1 | 2/2011 | Stegmann et al. |
| 2011/0071524 A1 | 3/2011 | Keller |
| 2011/0077626 A1 | 3/2011 | Baerveldt et al. |
| 2011/0082385 A1 | 4/2011 | Diaz et al. |
| 2011/0092965 A1 | 4/2011 | Slatkine et al. |
| 2011/0098629 A1 | 4/2011 | Juan, Jr. et al. |

(56) References Cited

U.S. PATENT DOCUMENTS

| | | |
|---|---|---|
| 2011/0098809 A1 | 4/2011 | Wardle et al. |
| 2011/0112546 A1 | 5/2011 | Juan, Jr. et al. |
| 2011/0118649 A1 | 5/2011 | Stegmann et al. |
| 2011/0118835 A1 | 5/2011 | Silvestrini et al. |
| 2011/0144641 A1 | 6/2011 | Dimalanta, Jr. et al. |
| 2011/0202049 A1 | 8/2011 | Jia et al. |
| 2011/0224597 A1 | 9/2011 | Stegmann et al. |
| 2011/0230877 A1 | 9/2011 | Huculak et al. |
| 2011/0257658 A1 | 10/2011 | Chen et al. |
| 2011/0306915 A1 | 12/2011 | De Juan, Jr. et al. |
| 2011/0319793 A1 | 12/2011 | Hyhynen |
| 2011/0319806 A1 | 12/2011 | Wardle |
| 2012/0016286 A1 | 1/2012 | Silvestrini et al. |
| 2012/0022409 A1 | 1/2012 | Gertner et al. |
| 2012/0022424 A1 | 1/2012 | Yamamoto et al. |
| 2012/0022429 A1 | 1/2012 | Silvestrini et al. |
| 2012/0035524 A1 | 2/2012 | Silvestrini |
| 2012/0035525 A1 | 2/2012 | Silvestrini |
| 2012/0065570 A1 | 3/2012 | Yeung et al. |
| 2012/0071908 A1 | 3/2012 | Sorensen et al. |
| 2012/0078158 A1 | 3/2012 | Haffner et al. |
| 2012/0078281 A1 | 3/2012 | Cox et al. |
| 2012/0078362 A1 | 3/2012 | Haffner et al. |
| 2012/0123439 A1 | 5/2012 | Romoda et al. |
| 2012/0123440 A1 | 5/2012 | Horvath et al. |
| 2012/0165721 A1 | 6/2012 | Grabner et al. |
| 2012/0165722 A1 | 6/2012 | Horvath et al. |
| 2012/0165723 A1 | 6/2012 | Horvath et al. |
| 2012/0165933 A1 | 6/2012 | Haffner et al. |
| 2012/0197175 A1 | 8/2012 | Horvath et al. |
| 2012/0203262 A1 | 8/2012 | Connors et al. |
| 2012/0220917 A1 | 8/2012 | Silvestrini et al. |
| 2012/0232570 A1 | 9/2012 | Jenson et al. |
| 2012/0238994 A1 | 9/2012 | Nazzaro et al. |
| 2012/0257167 A1 | 10/2012 | Gille et al. |
| 2012/0259195 A1 | 10/2012 | Haffner et al. |
| 2012/0271272 A1 | 10/2012 | Hammack et al. |
| 2012/0283557 A1 | 11/2012 | Berlin |
| 2012/0310137 A1 | 12/2012 | Silvestrini |
| 2012/0323159 A1 | 12/2012 | Wardle et al. |
| 2013/0006165 A1 | 1/2013 | Eutenener et al. |
| 2013/0018295 A1 | 1/2013 | Haffner et al. |
| 2013/0018296 A1 | 1/2013 | Bergheim et al. |
| 2013/0018412 A1 | 1/2013 | Journey et al. |
| 2013/0079701 A1 | 3/2013 | Schieber et al. |
| 2013/0079759 A1 | 3/2013 | Dotson et al. |
| 2013/0085507 A1 | 4/2013 | Nagasaka |
| 2013/0090534 A1 | 4/2013 | Burns et al. |
| 2013/0110125 A1 | 5/2013 | Silvestrini et al. |
| 2013/0184631 A1 | 7/2013 | Pinchuk |
| 2013/0245532 A1 | 9/2013 | Tu et al. |
| 2013/0253404 A1 | 9/2013 | Tu |
| 2013/0253405 A1 | 9/2013 | Tu |
| 2013/0253528 A1* | 9/2013 | Haffner ............... A61F 9/0017 606/107 |
| 2013/0281910 A1 | 10/2013 | Tu |
| 2013/0289467 A1 | 10/2013 | Haffner et al. |
| 2013/0310930 A1 | 11/2013 | Tu et al. |
| 2014/0052046 A1 | 2/2014 | Peartree et al. |
| 2014/0081194 A1 | 3/2014 | Burns et al. |
| 2014/0135916 A1 | 5/2014 | Clauson et al. |
| 2014/0155803 A1 | 6/2014 | Silvestrini |
| 2014/0207137 A1 | 7/2014 | Keller |
| 2014/0276901 A1 | 9/2014 | Auld |
| 2015/0223981 A1 | 8/2015 | Smedley et al. |
| 2015/0342875 A1 | 12/2015 | Haffner |
| 2016/0256323 A1 | 9/2016 | Horvath et al. |
| 2016/0354309 A1 | 12/2016 | Heitzmann et al. |
| 2017/0105750 A1 | 4/2017 | Cote et al. |
| 2017/0135857 A1 | 5/2017 | Haffner et al. |
| 2018/0021170 A1 | 1/2018 | Haffner et al. |
| 2018/0028361 A1 | 2/2018 | Haffner et al. |
| 2018/0085065 A1 | 3/2018 | Haffner et al. |
| 2018/0104102 A1 | 4/2018 | Lynch et al. |
| 2018/0161205 A1 | 6/2018 | Tu et al. |
| 2018/0177633 A1 | 6/2018 | Haffner et al. |
| 2018/0280194 A1 | 10/2018 | Heitzmann et al. |
| 2018/0303665 A1 | 10/2018 | Heitzmann et al. |
| 2018/0303752 A1 | 10/2018 | Haffner |
| 2018/0333296 A1 | 11/2018 | Heitzmann et al. |
| 2019/0000673 A1 | 1/2019 | Fjield et al. |
| 2019/0021991 A9 | 1/2019 | Heitzmann et al. |
| 2019/0053704 A1 | 2/2019 | Burns et al. |
| 2019/0083307 A1 | 3/2019 | Burns et al. |
| 2019/0083313 A1 | 3/2019 | Berlin |
| 2019/0091012 A1 | 3/2019 | Kalina, Jr. |
| 2019/0104936 A1 | 4/2019 | Gunn et al. |
| 2019/0125581 A1 | 5/2019 | Heitzmann et al. |
| 2019/0224046 A1 | 7/2019 | Heitzmann et al. |
| 2019/0314199 A1 | 10/2019 | Haffner et al. |
| 2019/0321220 A1 | 10/2019 | Rangel-Friedman et al. |
| 2019/0321225 A1 | 10/2019 | Smedley et al. |
| 2019/0321226 A1 | 10/2019 | Haffner et al. |
| 2020/0155349 A1 | 5/2020 | Haffner et al. |
| 2020/0179171 A1 | 6/2020 | Crimaldi et al. |
| 2020/0214560 A1 | 7/2020 | Kalina, Jr. et al. |
| 2020/0214561 A1 | 7/2020 | Kalina, Jr. et al. |
| 2020/0367745 A1 | 11/2020 | Kalina, Jr. et al. |
| 2021/0015662 A1 | 1/2021 | Haffner et al. |
| 2021/0137737 A1 | 5/2021 | Burns et al. |
| 2021/0154449 A1 | 5/2021 | Haffner et al. |
| 2021/0298948 A1 | 9/2021 | Haffner et al. |
| 2021/0315806 A1 | 10/2021 | Haffner |
| 2021/0369447 A1 | 12/2021 | Kalina, Jr. |
| 2022/0000663 A1 | 1/2022 | Haffner et al. |
| 2022/0015628 A1 | 1/2022 | Kalina, Jr. et al. |

FOREIGN PATENT DOCUMENTS

| | | |
|---|---|---|
| CA | 2244646 | 2/1999 |
| CA | 2311244 | 6/1999 |
| CA | 2643357 | 11/1999 |
| CA | 2766131 | 1/2011 |
| CA | 2762536 | 11/2020 |
| CH | 92111244 | 7/1993 |
| CN | 1976732 | 6/2007 |
| CN | 106456372 A | 2/2017 |
| CN | 107126315 | 9/2017 |
| CN | 107498340 | 12/2017 |
| CN | 107530190 A | 1/2018 |
| CN | 109156098 | 1/2019 |
| CN | 106029019 A | 7/2020 |
| CN | 107205815 A | 9/2020 |
| EP | 0436232 | 7/1991 |
| EP | 0550791 | 7/1993 |
| EP | 2088976 | 8/2009 |
| FR | 2349469 | 11/1977 |
| JP | 2005-533619 | 11/2005 |
| JP | 2007-500063 | 1/2007 |
| JP | 2009-542370 | 12/2009 |
| JP | 2010-533565 | 10/2010 |
| JP | 2016-511108 | 4/2016 |
| RU | 2143250 | 12/1999 |
| WO | WO 1991/08784 | 6/1991 |
| WO | WO 1992/08406 | 5/1992 |
| WO | WO 1998/23237 | 6/1998 |
| WO | WO 1998/37831 | 9/1998 |
| WO | WO 1999/26567 | 6/1999 |
| WO | WO 2000/64389 | 11/2000 |
| WO | WO 2000/64390 | 11/2000 |
| WO | WO 2000/64391 | 11/2000 |
| WO | WO 2000/64393 | 11/2000 |
| WO | WO 2001/68016 | 9/2001 |
| WO | WO 2001/78631 | 10/2001 |
| WO | WO 2001/085065 | 11/2001 |
| WO | WO 2001/97727 | 12/2001 |
| WO | WO 2002/36052 | 5/2002 |
| WO | WO 2002/074052 | 9/2002 |
| WO | WO 2002/080811 | 10/2002 |
| WO | WO 2002/087418 | 11/2002 |
| WO | WO 2002/089699 | 11/2002 |
| WO | WO 2003/015659 | 2/2003 |
| WO | WO 2003/041622 | 5/2003 |
| WO | WO 2003/073968 | 9/2003 |

(56) References Cited

FOREIGN PATENT DOCUMENTS

| | | |
|---|---|---|
| WO | WO 2004/014218 | 2/2004 |
| WO | WO 2004/043231 | 5/2004 |
| WO | WO 2005/016418 | 2/2005 |
| WO | WO 2005/105197 | 11/2005 |
| WO | WO 2005/107845 | 11/2005 |
| WO | WO 2006/036715 | 4/2006 |
| WO | WO 2007/130393 | 11/2007 |
| WO | WO 2008/061043 | 5/2008 |
| WO | WO 2008/083118 | 7/2008 |
| WO | WO 2009/012406 | 1/2009 |
| WO | WO 2009/126569 | 10/2009 |
| WO | WO 2009/151543 | 12/2009 |
| WO | WO 2010/006053 | 1/2010 |
| WO | WO 2010/077987 | 7/2010 |
| WO | WO 2010/078063 | 7/2010 |
| WO | WO 2010/093945 | 8/2010 |
| WO | WO 2010/135369 | 11/2010 |
| WO | WO 2011/020633 | 2/2011 |
| WO | WO 2011/084550 | 7/2011 |
| WO | WO 2012/071476 | 5/2012 |
| WO | WO 2013/040079 | 3/2013 |
| WO | WO 2013/148275 | 10/2013 |
| WO | WO 2014/150292 | 9/2014 |
| WO | WO 2014/151070 | 9/2014 |
| WO | WO 2014/164569 | 10/2014 |
| WO | WO 2015/073571 | 5/2015 |
| WO | WO 2015/184173 | 12/2015 |
| WO | WO 2016/019160 | 2/2016 |
| WO | WO 2016/154066 | 9/2016 |
| WO | WO 2016/187355 | 11/2016 |
| WO | WO 2017/015633 | 1/2017 |
| WO | WO 2017/040853 | 3/2017 |
| WO | WO 2017/040855 | 3/2017 |
| WO | WO 2017/053885 | 3/2017 |
| WO | WO 2017/087713 | 5/2017 |
| WO | WO 2017/184881 | 10/2017 |
| WO | WO 2019/036025 | 2/2019 |
| WO | WO 2019/070385 | 4/2019 |
| WO | WO 2020/172615 | 8/2020 |

OTHER PUBLICATIONS

Chen et al., "Implantable Unpowered Parylene MEMS Intraocular Pressure Sensor", Microtechnologies in Medicine and Biology, 2006 International Conference on Publication Date: May 9-12, 2006, 5pp., downloaded from http://ieeezxplore.ieee.org/xpl/freeabs_all.jsp?arnumber=4281361.

De Juan et al., "Refinements in microinstrumentation for vitrous surgery," Am. J. Ophthalmol. 109:218-20 (1990).

https://entokey.com/gonioscopy-2/ Uploaded Oct. 2016.

Jordan et al., "A Novel Approach to Suprachoroidal Drainage for the Surgical Treatment of Intractable Glaucoma", J Glaucoma, vol. 15, No. 3, Jun. 2006, pp. 200-205.

Katuri et al., "Intraocular Pressure Monitoring Sensors", IEEE Sensors Journal, vol. 8, No. 1, Jan. 2008, 8 pp.

Online encyclopedia article "Hyaluronan," section on "Medical Applications" accessed Monday, Sep. 27, 2010. http://en.wikipedia.org/wiki/Hyaluronic_acid.

Rizq, et al., "Intraocular Pressure measurement at the Chroid Surface: A Feasibility Study with Implications for Implantable Microsystems", Br J Ophthalmol 2001; 85:868-871, Jul. 2001.

Ianchulev et al., "Minimally Invasive Ab-Interno Suprachoroidal Device (CyPass) for IOP Control in Open-Angle Glaucoma," presented at the Annual Meeting of the American Academy of Ophthalmology Oct. 16-19, 2010, Chicago, IL.

Walter et al., "Development of a Completely Encapsulated Intraocular Pressure Sensor", Ophthalmic Res 2000; 32:278-284. Nov. 5, 1999.

* cited by examiner

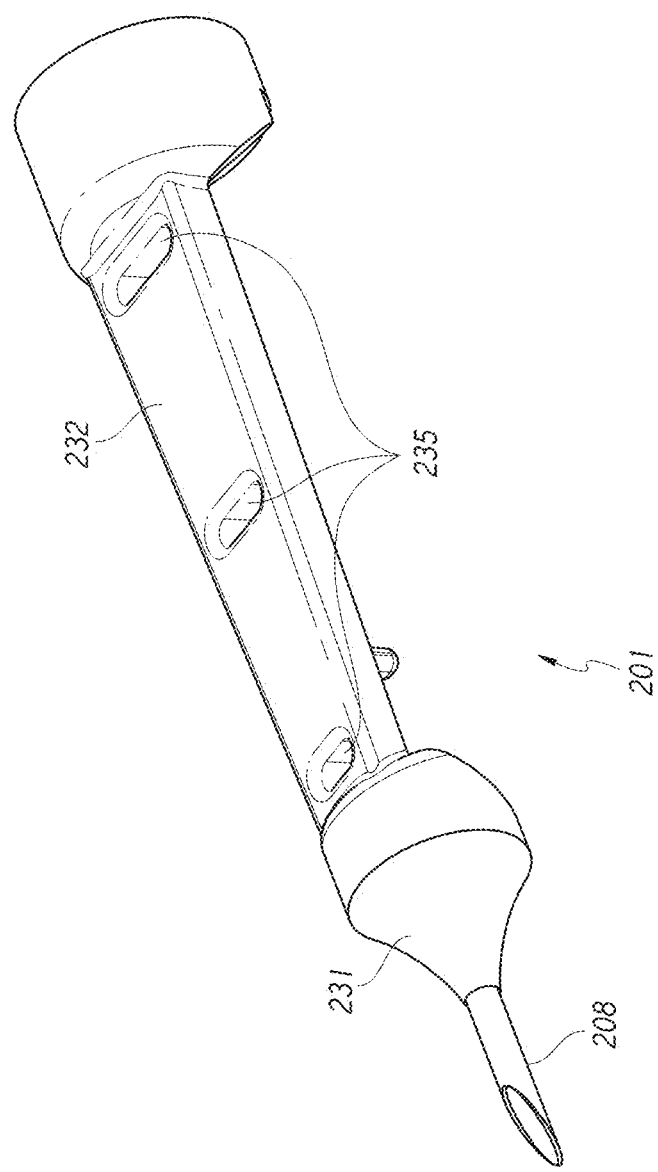

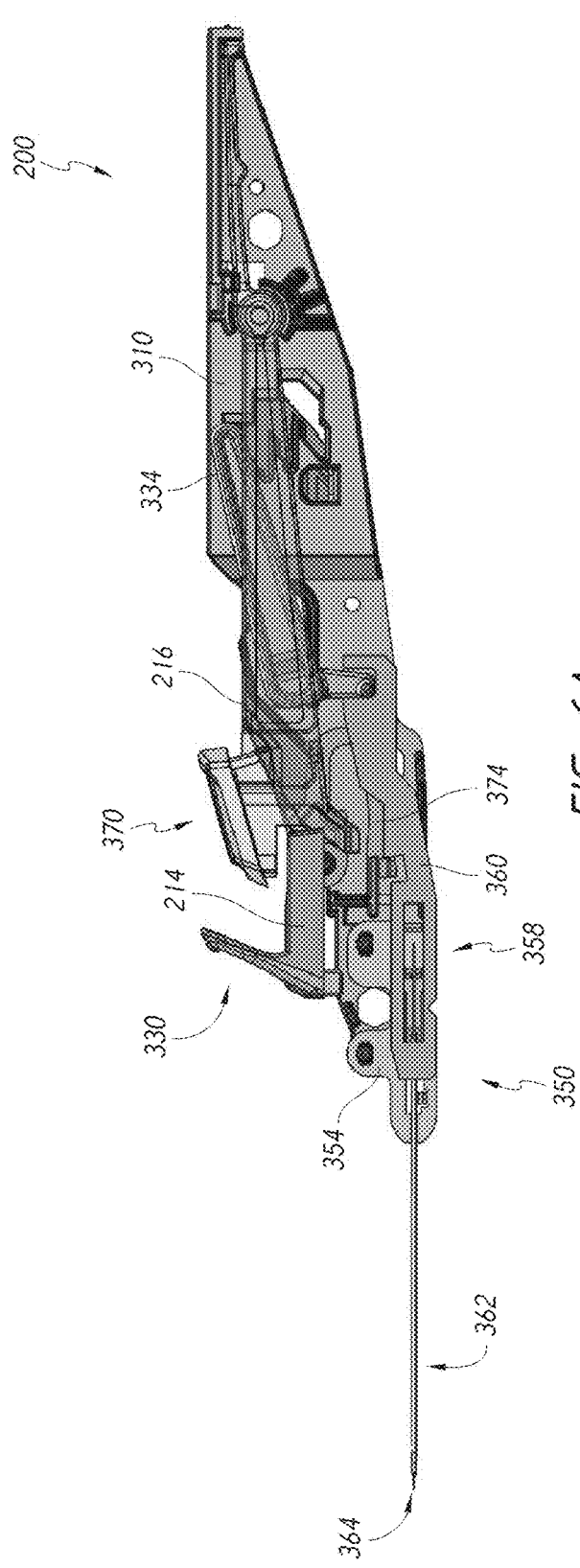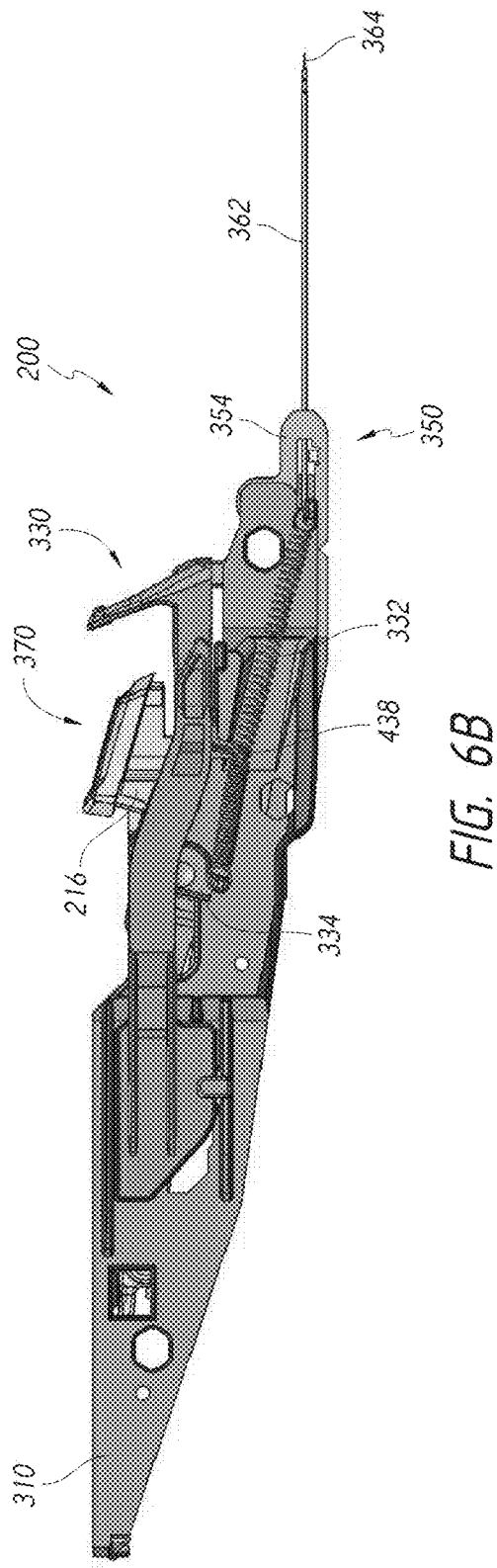
FIG. 6A
FIG. 6B

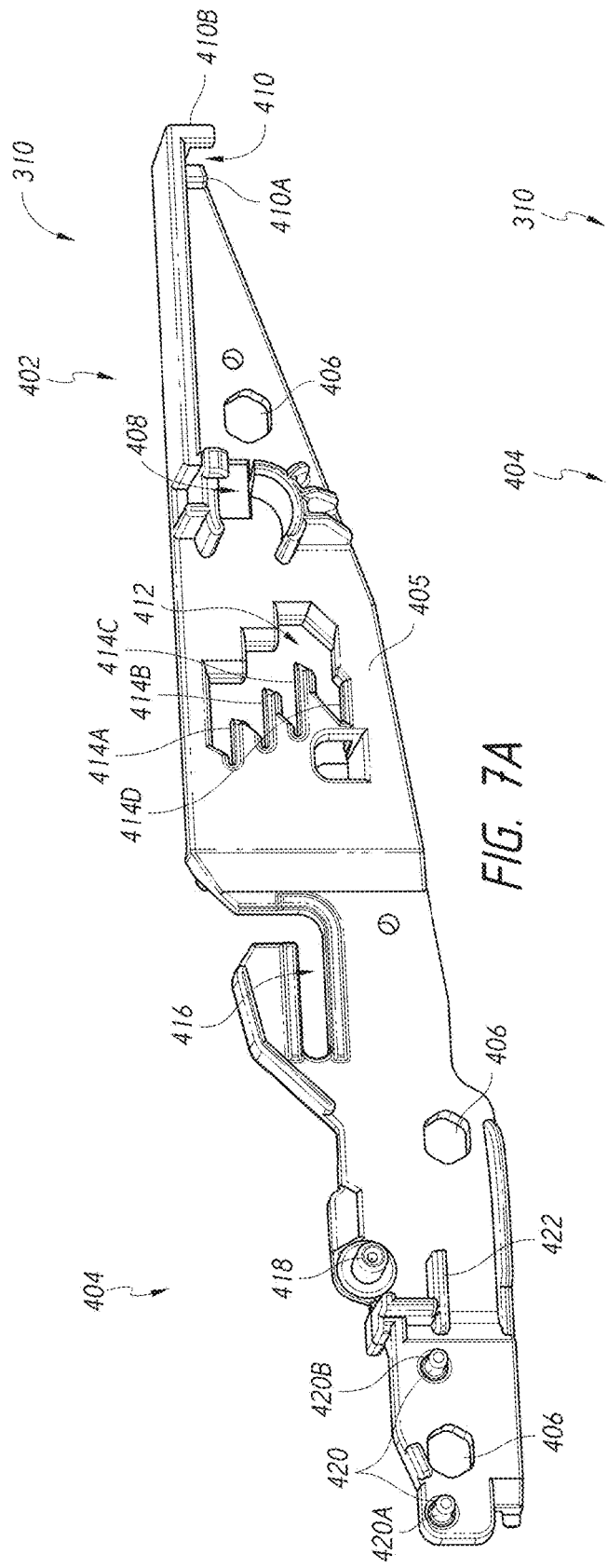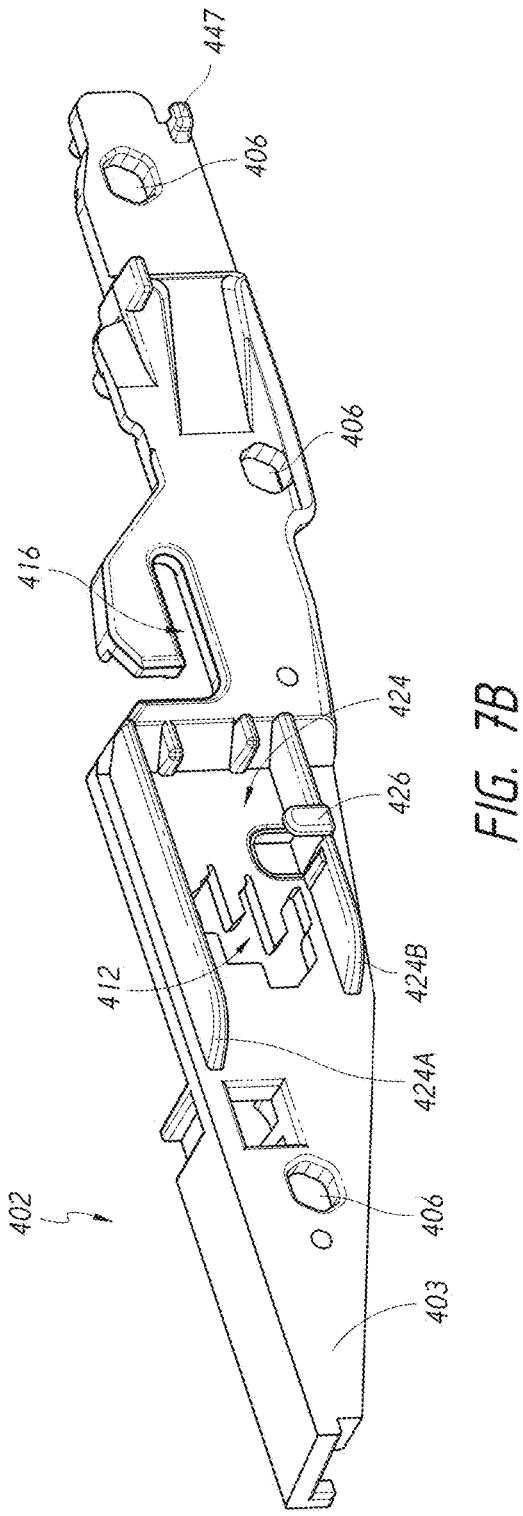
FIG. 7A
FIG. 7B

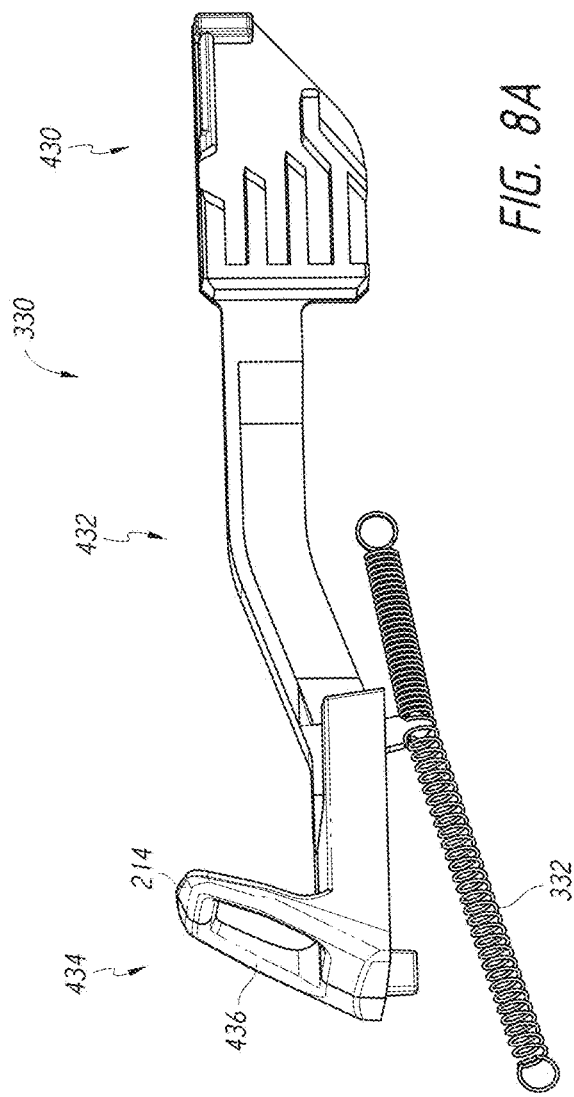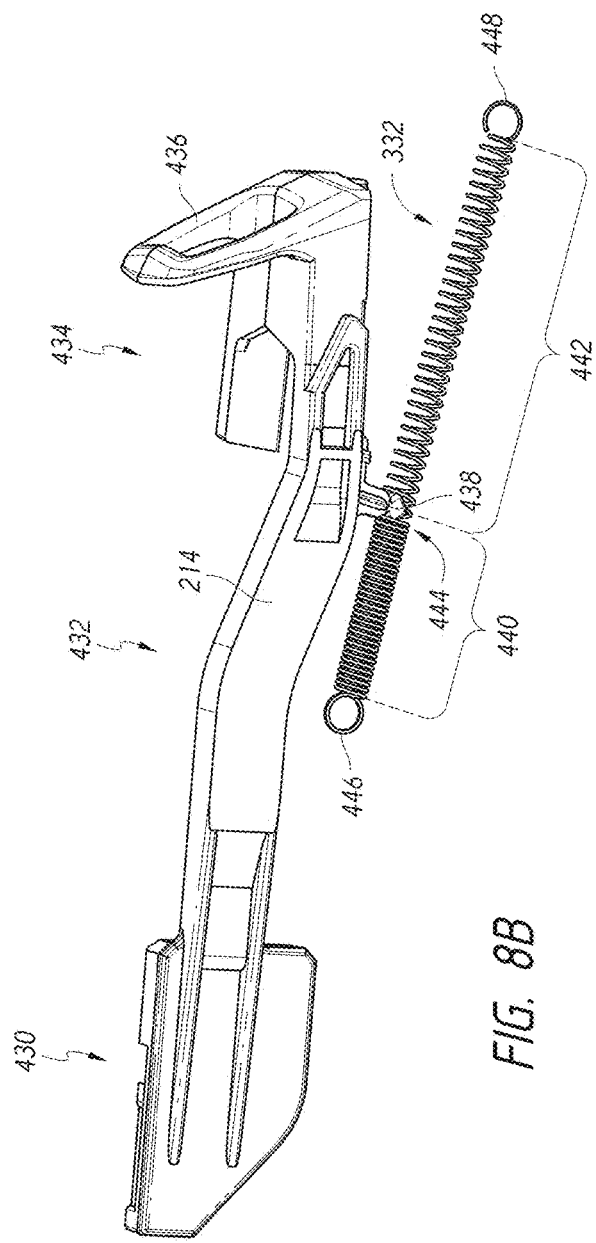

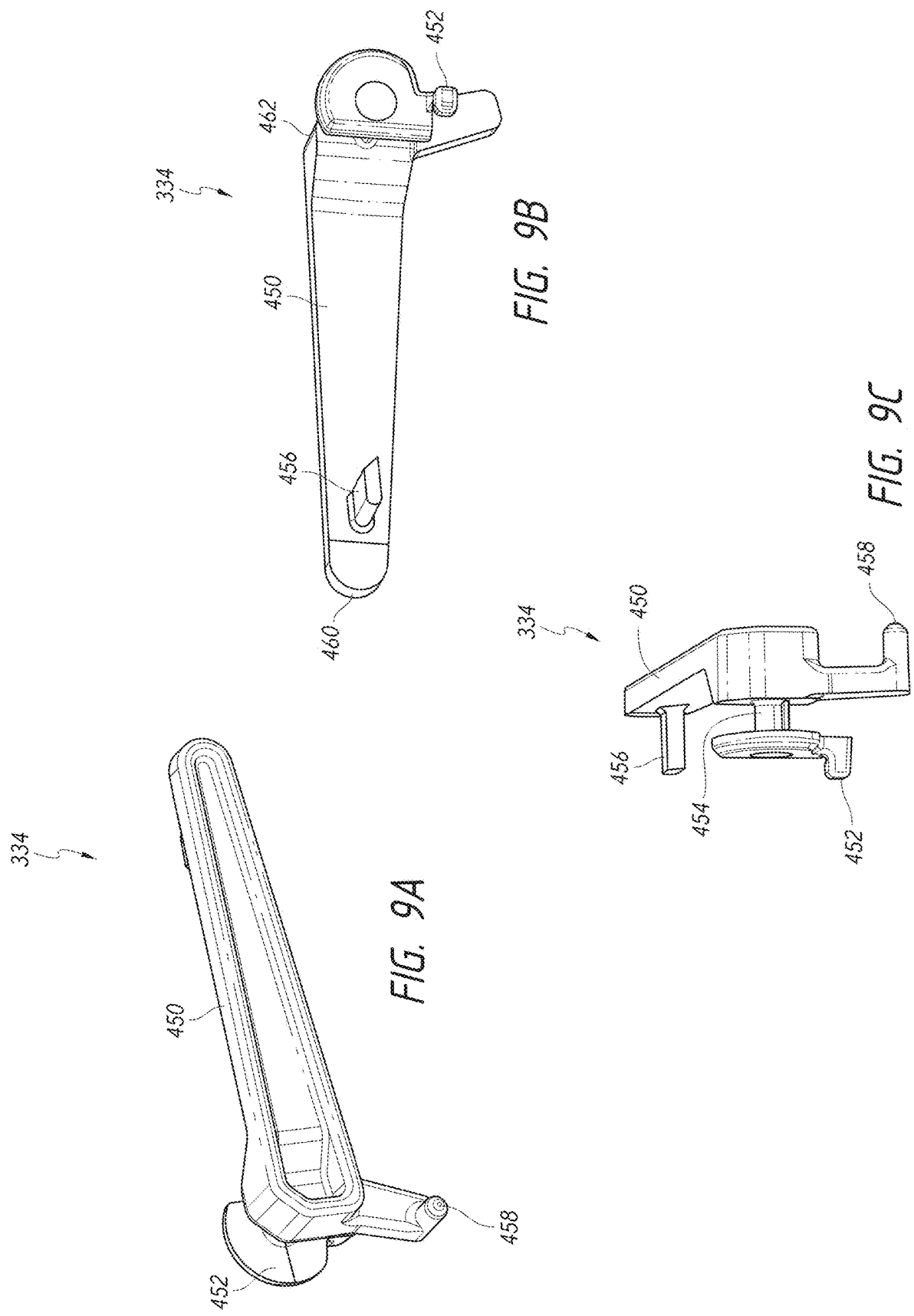

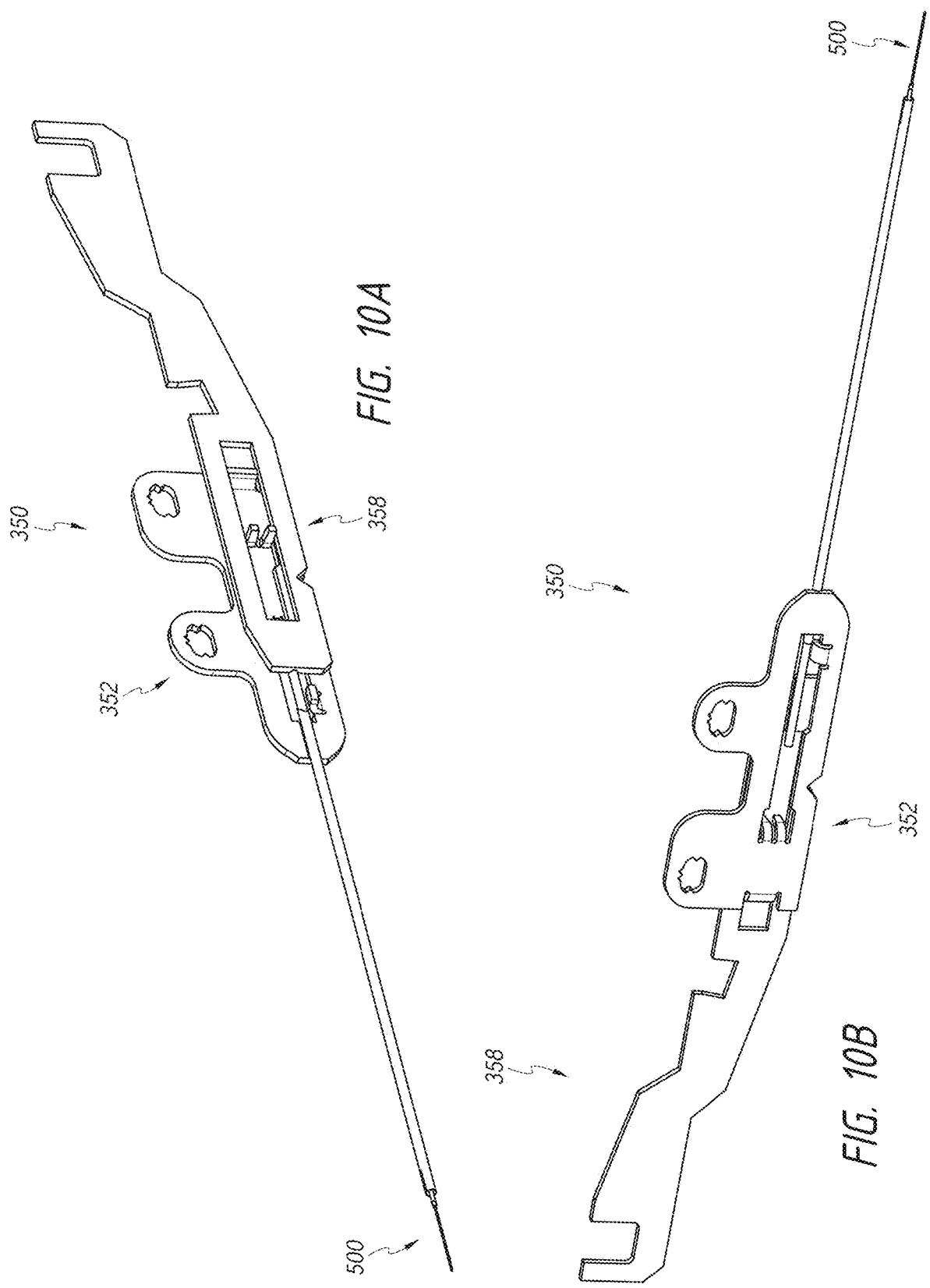

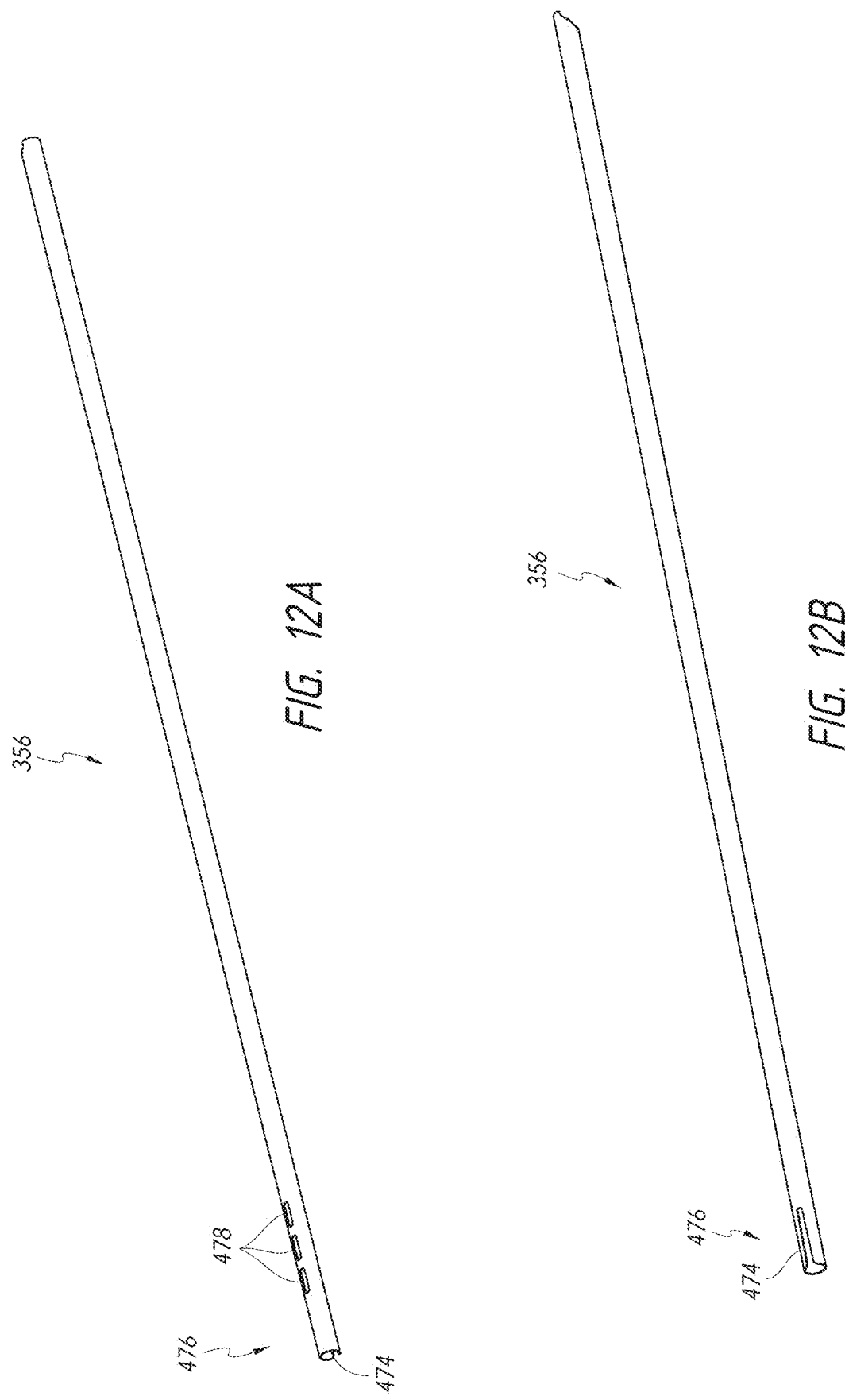

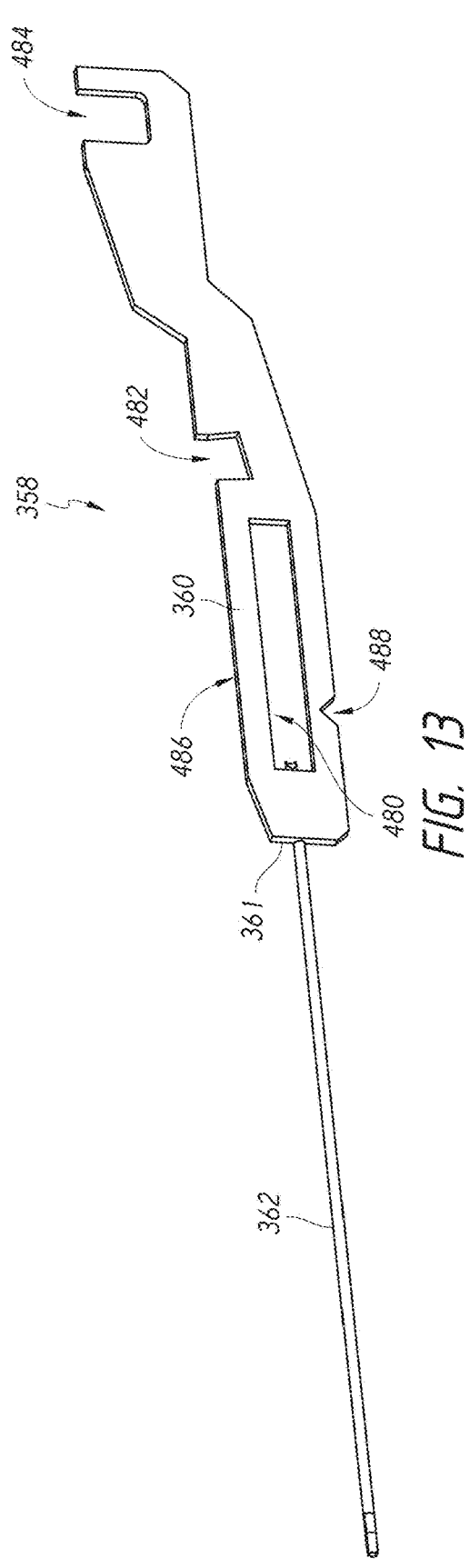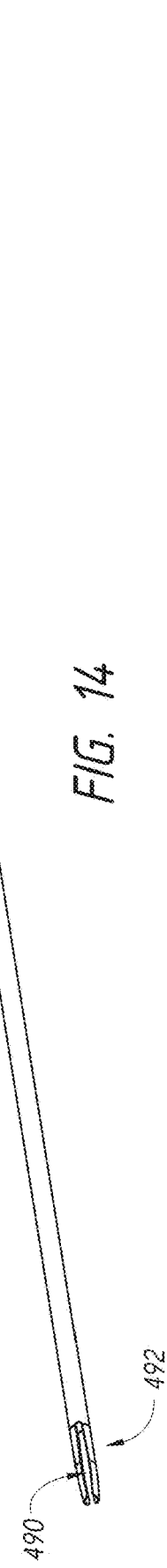

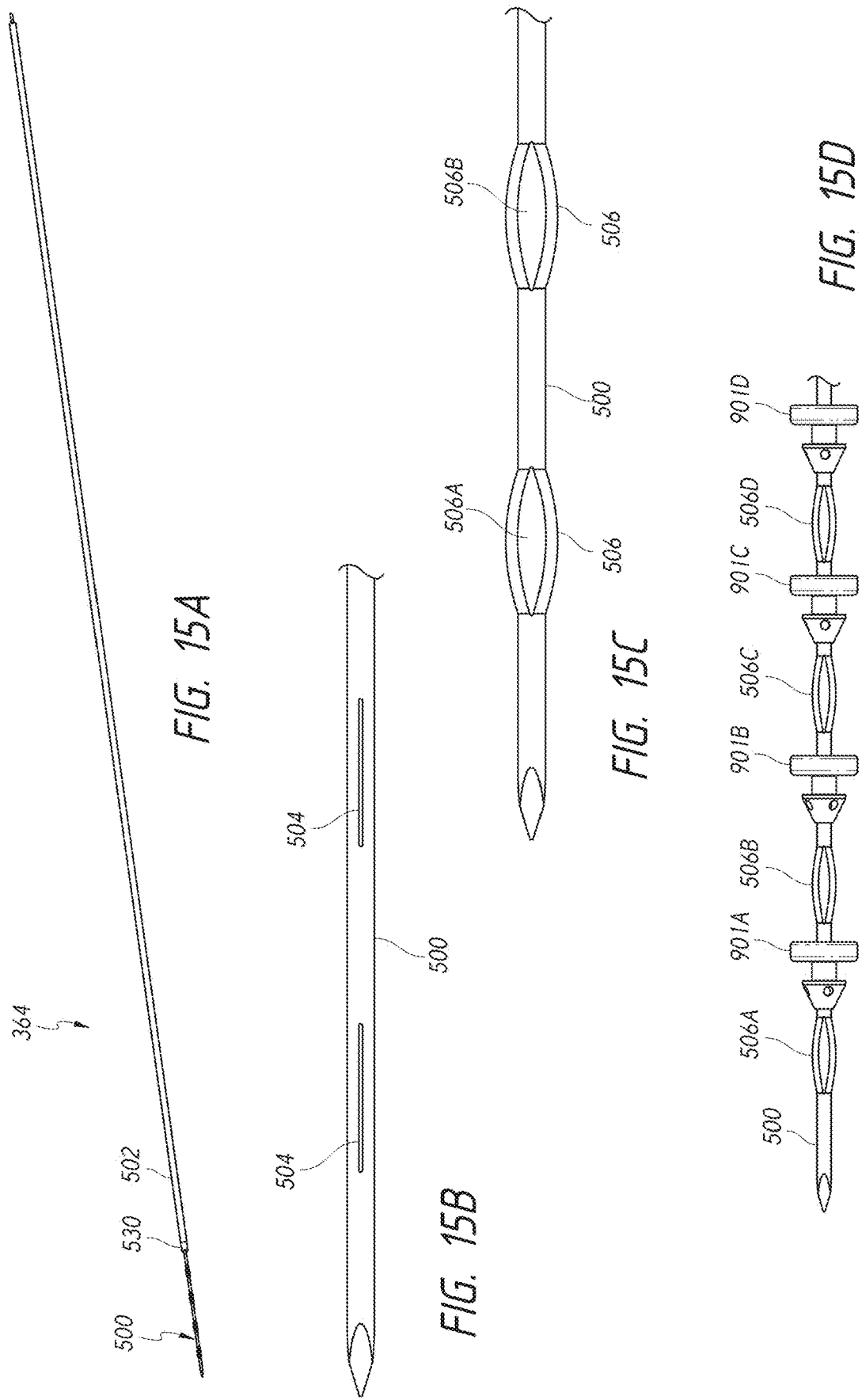

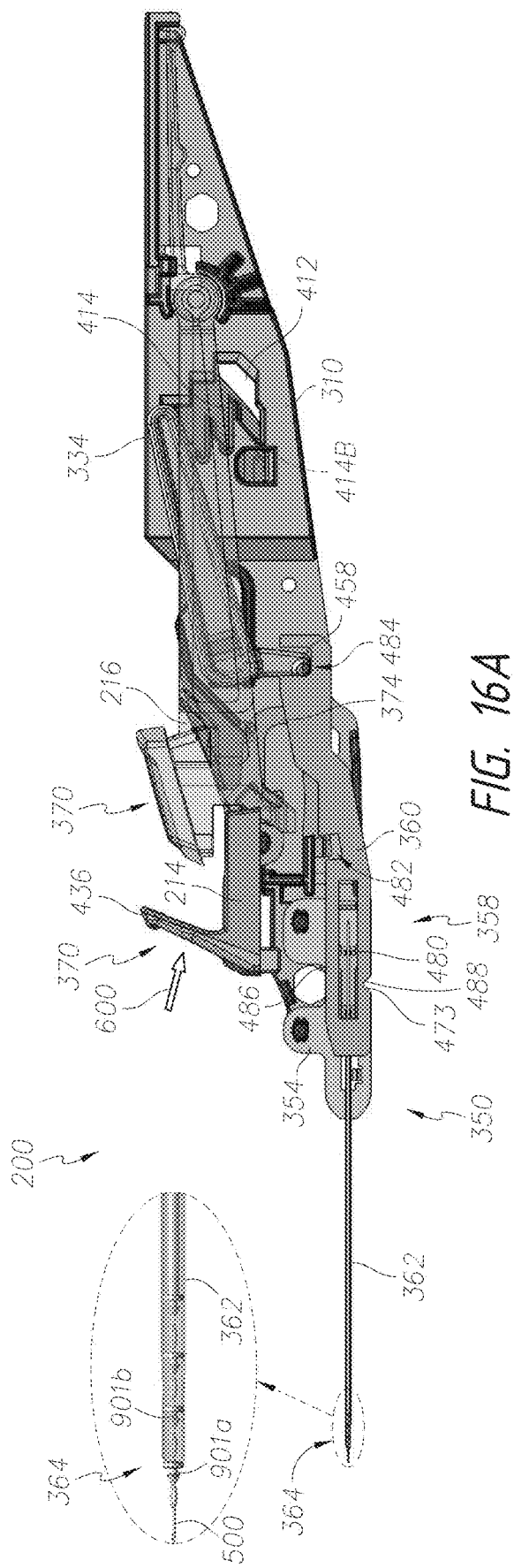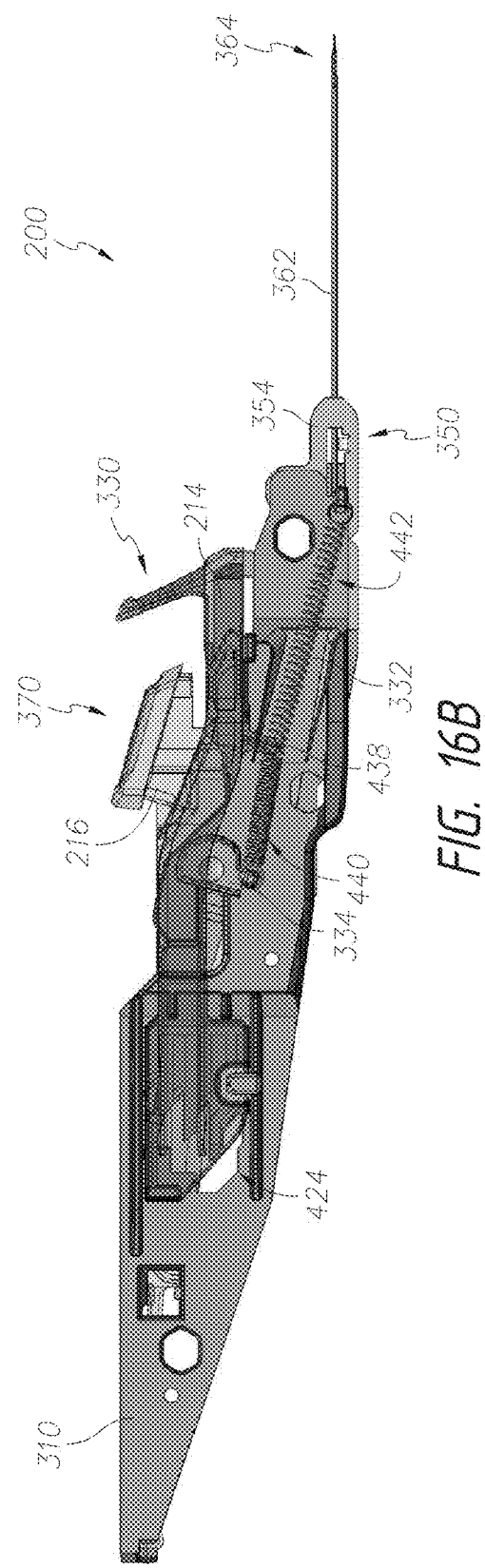
FIG. 16A
FIG. 16B

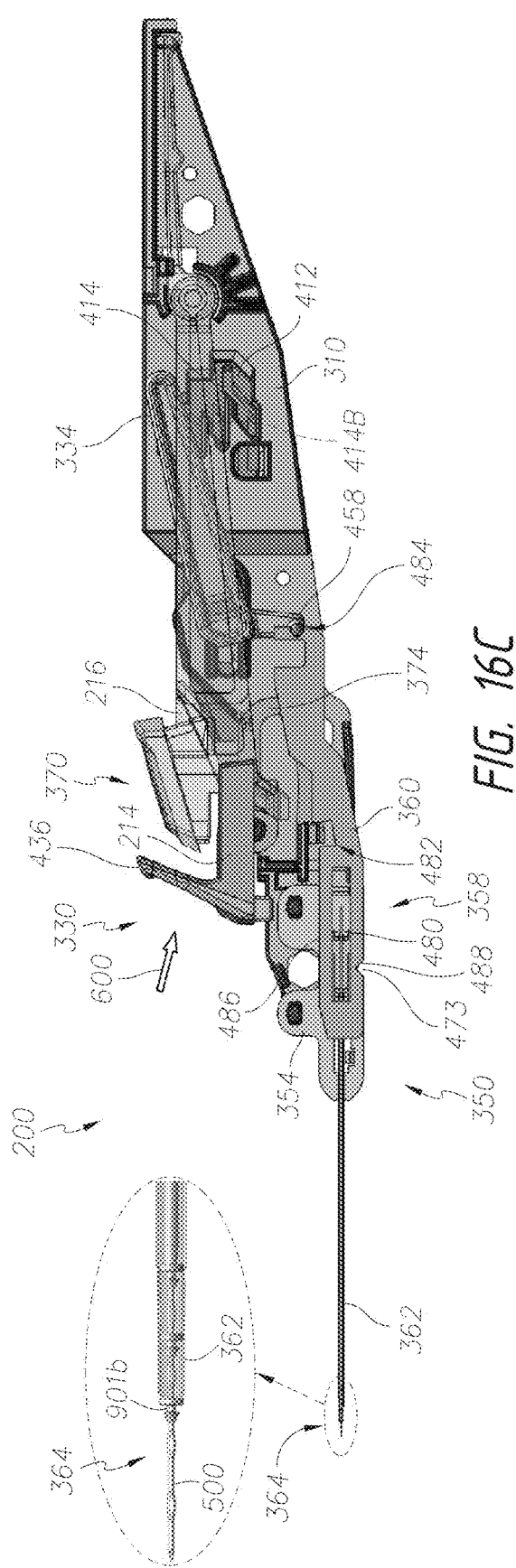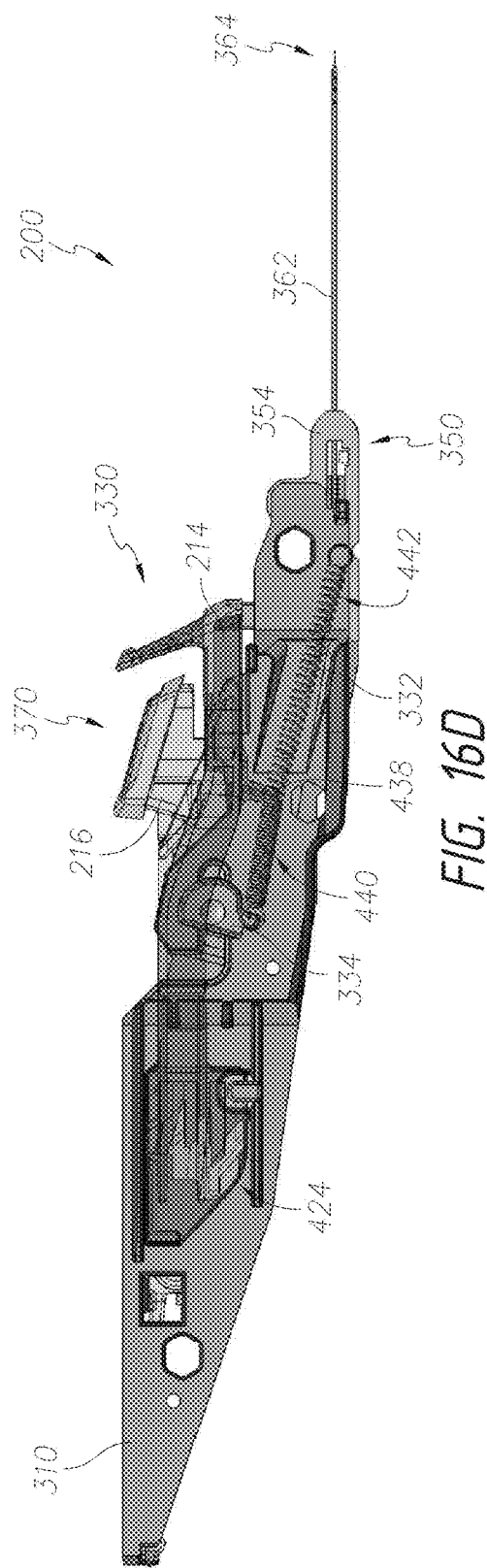
FIG. 16C
FIG. 16D

SYSTEMS AND METHODS FOR DELIVERING MULTIPLE OCULAR IMPLANTS

CROSS-REFERENCE TO RELATED APPLICATIONS

This application claims the benefit under 35 U.S.C. § 119(e) of U.S. Provisional Patent Application Nos. 62/569,458 filed Oct. 6, 2017; 62/578,273 filed Oct. 27, 2017; and 62/671,286 filed May 14, 2018; each of which is hereby incorporated by reference in its entirety and made a part of this specification for all that it discloses.

FIELD

Embodiments of the inventions generally relate to devices and methods for delivering multiple implants using a single delivery apparatus without having to remove the apparatus from a body of the subject between implantations.

BACKGROUND

A human eye is a specialized sensory organ capable of light reception and is able to receive visual images. Aqueous humor (hereinafter referred to as "aqueous") is a transparent liquid that fills at least the region between the cornea, at the front of the eye, and the lens. Aqueous is continuously secreted by ciliary processes of a ciliary body to the posterior chamber of the eye and the aqueous flows to the anterior chamber by crossing the pupil, so there is a constant flow of aqueous humor from the ciliary body to the anterior chamber of the eye. The aqueous fluid supplies nutrients to the avascular structures of the eye (for example, the cornea and the lens) and maintains intraocular pressure. Pressure within the eye is determined by a balance between the production of aqueous and its exit through canalicular outflow, uveo-scleral outflow, or other outflow routes or pathways.

Many open-angle glaucomas are caused by an increase in the resistance to aqueous drainage through the trabecular meshwork and/or Schlemm's canal (e.g., the canalicular outflow pathways). The tissue of the trabecular meshwork normally allows the aqueous to enter Schlemm's canal, which then empties into aqueous collector channels in the posterior wall of Schlemm's canal and then into aqueous veins, which form the episcleral venous system. The uveo-scleral outflow pathways can refer to the aqueous leaving the anterior chamber by diffusion through intercellular spaces among ciliary muscle fibers or through a supraciliary and/or suprachoroidal space.

Intraocular implants (for example, shunts or stents) can be implanted within the eye to facilitate the outflow of aqueous, thereby reducing intraocular pressure. Typical methods of implantation require relatively invasive surgical procedures, pose a risk of excessive trauma to the eye, and require excessive handling of the implant. For example, in a typical method of implantation, an incision is made through the sclera or cornea and the implant is inserted into the desired implantation location using forceps or another like manual grasping device. These forceps are configured for holding, and introducing into the eye only one implant at a time. This requires reloading and repositioning of the forceps prior to inserting each implant into the eye. Once the implants are deposited, the grasping device is removed and the incision is sutured closed.

SUMMARY

According to some embodiments, an implant delivery apparatus for treating an ocular disorder can include an external housing and an introducer assembly. The external housing can include an opening, a singulation portion, and an activation portion. The singulation portion can be actuated by a user. The activation portion can be actuated by the user. The auto-retracting introducer assembly can include a distal introducer tip and a flexible proximal retraction member. The distal introducer tip can extend from a distal end portion of the flexible retraction member. The introducer assembly can surround and be guided by at least a portion of an insertion tube. The introducer tip (and/or an introducer tube surrounded by the introducer tip) can extend from the external housing at an angle relative to a longitudinal axis of the implant delivery apparatus. The singulation portion is configured to be manually actuated by a user. The activation portion may be configured to be an infinite activation portion and the singulation portion may be configured to be manually actuated.

In accordance with several embodiments, a method of treating an ocular disorder includes advancing at least a portion of an implant delivery apparatus through an incision in an eye. The implant delivery apparatus may include an introducer assembly including an insertion tube defining a lumen and a trocar assembly pre-loaded with a plurality of implants, the trocar assembly configured to be positioned within the lumen, and an actuation assembly configured to facilitate delivery of a first implant of the plurality of implants, the actuation assembly comprising an actuator trigger portion configured to be accessible by a user. The method further includes piercing ocular tissue with the introducer assembly, positioning the implant delivery apparatus adjacent a desired implantation location and depressing the actuator trigger portion to effect delivery of the first implant by causing the insertion tube to contact the first implant, the actuator trigger portion configured to be depressed an infinite number of times to properly deliver the first implant. The implants may be ocular implants configured to facilitate drainage of aqueous humor from an anterior chamber of an eye to a physiologic outflow pathway (e.g., Schlemm's canal, collector channel, suprachoroidal space, supraciliary space) of the eye. The plurality of implants may consist of any one of two implants, three implants, and four implants without requiring reconfiguration. In other words, the apparatus operates in the same manner regardless of how many implants are loaded therein. In some embodiments, energy required to deliver each respective implant of the plurality of implants is generated by an actuation biasing member upon the depressing of the actuator trigger portion such that no energy is pre-stored by the actuation biasing member prior to the depressing of the actuator trigger portion.

In accordance with several embodiments, a method of treating an ocular disorder includes positioning an implant delivery apparatus within an eye. The implant delivery apparatus includes an introducer assembly including a singulation tube and a trocar assembly pre-loaded with a plurality of implants and a singulation assembly configured to facilitate selection of an implant of the plurality of implants, the singulation assembly including a singulation handle configured to be accessible by a user. The method also includes manipulating the singulation handle to effect selection of the implant, the manipulation configured to cause the singulation tube to slide over the at least one implant such that the singulation tube is positioned proximally relative to a proximally facing side of the implant.

In accordance with several embodiments, a method of treating an ocular disorder (e.g., glaucoma) includes positioning an implant delivery apparatus within an eye. The implant delivery apparatus includes a trocar pre-loaded with a plurality of implants and a singulation tube coaxially surrounding the trocar and being configured to move proximally and distally (e.g., rearward and forward) with respect to the trocar. The implant delivery apparatus also includes a singulation assembly configured to facilitate selection of a first implant of the plurality of implants. The singulation assembly includes a singulation handle configured to be accessible by an operator. The method further includes retracting the singulation handle toward the operator to effect selection of the first implant, the retraction configured to cause the singulation tube to slide over the first implant such that the singulation tube is positioned proximally relative to a proximally-facing side of the first implant.

The method may also include causing the singulation tube to propel the first implant toward a distal end of the trocar by actuating an implant delivery actuator of the implant delivery apparatus. The method may further include retracting the singulation handle toward the operator a second time to effect selection of a second implant of the plurality of implants, the retraction configured to cause the singulation tube to slide over the second implant such that the singulation tube is positioned proximally relative to a proximally-facing side of the second implant. The trocar may include a plurality of separation regions formed by slits in the trocar at spaced-apart locations along the length of the trocar. The separation regions may be configured to mechanically separate the plurality of implants from each other until the singulation tube engages the proximal end of a respective one of the plurality of implants and advances the implant to a ready-to-fire position along the trocar. The method may also include repositioning an implant delivery apparatus within an eye at a different location.

In accordance with several embodiments, an implant delivery apparatus configured to deliver a plurality of implants for treating an ocular disorder includes an external housing including an opening on an upper side of the external housing. The apparatus may also include an auto-retracting introducer assembly configured to facilitate introduction of a distal portion of the implant delivery apparatus into an eye of a subject. The introducer assembly includes a distal introducer tip and a flexible proximal retraction member extending from a distal end of the external housing. The apparatus further includes a singulation assembly configured to facilitate on-demand singulation of each of the plurality of implants upon manual actuation by an operator of a lever extending out of the opening of the external housing. The apparatus also includes an implantation actuator assembly configured to effect delivery of each of the plurality of implants following singulation. The implantation actuator assembly includes an implant delivery actuator including a trigger button extending out of the opening of the external housing that is configured to be actuated an infinite (e.g., unlimited) number of times by the operator.

The apparatus may further include an insertion tube extending from a distal end of the external housing at an angle relative to a longitudinal axis of the implant delivery apparatus, the insertion tube configured to retain the plurality of implants therein. The angle may be between 1 and 15 degrees (e.g., between 7 and 9 degrees, between 6 and 10 degrees, between 5 and 12 degrees, between 7 and 11 degrees, between 1 and 10 degrees, between 7 and 15 degrees, overlapping ranges thereof, or any value within the recited ranges).

The apparatus may also include a trocar positioned within the external housing, a distal end portion of the trocar being configured to extend within and along a length of a lumen of the insertion tube, wherein the plurality of implants are positioned along the distal end portion of the trocar. The apparatus may further include a collet holder assembly including a collet holder and a singulation tube extending from the collet holder. A distal end of the singulation tube may comprise multiple tines configured to facilitate retraction of the distal end of the singulation tube over a maximum cross-sectional dimension of a respective implant during singulation. The distal end of the singulation tube may be configured to engage a proximal end of the respective implant following singulation and to advance the respective implant to a ready-to-fire position along the trocar. The ready-to-fire position may advantageously be the same position for each successive implant of the plurality of implants.

The singulation assembly may further include a singulation arm coupled to the lever and to the collet holder and a singulation biasing member (e.g., a spring) coupled to the singulation arm and to a fixed frame within the external housing. Proximal retraction of the lever of the singulation assembly may cause the collet holder to retract proximally (e.g., rearwardly). Then, release of the lever may cause the singulation tube to engage the proximal end of the respective implant following singulation and to advance the respective implant to the ready-to-fire position along the trocar. The implantation actuator assembly may further include an actuator arm and an actuator biasing member (e.g., flat spring), wherein the energy sufficient to effect delivery of each respective implant is provided by the actuator biasing member (e.g., bending of the flat spring), and wherein the energy provided by the actuator biasing member is generated from pressing of the trigger button of the implant delivery actuator by the operator.

The trocar may include multiple singulation regions spaced apart along the length of the trocar. The singulation regions may be configured to facilitate mechanical separation of the plurality of implants from each other. The singulation regions may include splayed regions formed by slits in the trocar. The apparatus may be configured to deliver two, three, or four implants without requiring different configurations. In some embodiments, the fixed frame includes a singulation frame slot having a plurality of platforms or slots sized and shaped to facilitate singulation of the plurality of implants through interaction with one or more components of the singulation assembly.

In accordance with several embodiments, an implant delivery apparatus configured to deliver a plurality of implants for treating an ocular disorder includes an external housing including an opening, a trigger button configured to be actuated by a user extending out of the opening, an activation portion configured to be actuated by the user; and an introducer assembly. The introducer assembly includes an introducer tube extending from the external housing at an angle relative to a longitudinal axis of the implant delivery apparatus, the introducer tube configured to retain a plurality of implants therein. The angle may be between 1 and 15 degrees (e.g., between 7 and 9 degrees, between 6 and 10 degrees, between 5 and 12 degrees, between 7 and 11 degrees, between 1 and 10 degrees, between 7 and 15 degrees, overlapping ranges thereof, or any value within the recited ranges).

The introducer assembly may further include an auto-retracting introducer assembly configured to surround at least a portion of the introducer tube, the introducer assembly including a distal introducer tip and a flexible proximal retraction member, the distal introducer tip extending from a distal end portion of the flexible proximal retraction member. In some embodiments, the singulation portion is configured to be manually actuated by a user so as to facilitate on-demand manual singulation to effect selection of one of the plurality of implants for delivery one at a time. The actuation portion may include an actuator that is configured to be manually actuated by a user to effect ejection of an implant of the plurality of implants out of the introducer tube toward a distal end of the trocar. The actuation portion may be configured to allow manual actuation an infinite (e.g., unlimited) number of times. The apparatus may include a trocar configured to extend within and through the introducer tube. The plurality of implants are configured to be positioned and advanced along the trocar. The trocar may include a plurality of separation regions formed by slits along a length of the trocar at spaced-apart locations along the length of the trocar, the separation regions configured to separate the plurality of implants from each other until a singulation actuator of the singulation portion interacts with a respective one of the plurality of implants upon manual actuation of the singulation portion by the operator.

In accordance with several embodiments, an implant delivery apparatus with an activation portion configured to facilitate actuation of an implant delivery mechanism an infinite (e.g., unlimited) number of times includes an external housing including an opening within an upper side of the external housing, an implant delivery actuator including a trigger button extending out of the opening, an actuation biasing member (e.g., a flat spring), and an actuator arm. Depressing of the trigger button causes the actuation biasing member to store energy sufficient to eject, or propel, an implant toward a distal end of the implant delivery apparatus. Release of the trigger button causes the actuation biasing member to release the stored energy. In some embodiments, depressing of the trigger button causes the flat spring to bend, thereby storing the energy. The flat spring may be positioned in contact with the actuator arm so as to cause the flat spring to bend as the trigger button is depressed.

In accordance with several embodiments, an implant delivery apparatus having a manual "on-demand" singulation portion includes an external housing including an opening on an upper side of the external housing, a trocar having a plurality of implants loaded thereon, wherein each implant is spaced apart at a separation distance along the trocar, and a frame fixed to the external housing, the frame including a singulation frame slot configured to facilitate selection and movement to a ready-to-fire position along the trocar of one of the plurality of implants. The apparatus further includes a singulation assembly including a lever extending out of the opening of the external housing, the lever configured to be retracted proximally (e.g., rearwardly) by a finger or thumb of an operator. The singulation assembly also includes a singulation arm comprising a proximal end and a distal end, wherein the proximal end is coupled to the singulation frame slot and wherein the distal end is coupled to a collet holder assembly. The collet holder assembly includes a singulation tube.

In some embodiments, a singulation biasing member is coupled to the lever, to the distal end of the singulation arm, and to the frame within the external housing. Proximal retraction of the lever of the singulation assembly causes the collet holder assembly to retract proximally (e.g., rearwardly) and release of the lever causes the singulation tube of the collet holder assembly to engage a proximal end of one of the plurality of implants and advance the implant to the ready-to-fire position along the trocar. In some embodiments, the trocar includes a plurality of separation regions formed by slits in the trocar at spaced-apart locations along the length of the trocar. The separation regions may be configured to mechanically separate the plurality of implants from each other until the singulation tube engages the proximal end of a respective one of the plurality of implants and advances the implant to the ready-to-fire position along the trocar. The apparatus is configured to facilitate selection and delivery of two, three, or four implants without requiring different configurations.

According to several embodiments, the systems and methods described herein include one or more of the following advantages or benefits: (i) easy to assemble, (ii) inexpensive to manufacture (e.g., no overmolding, no adhesives, no lubricants), (iii) less concern about tight tolerances, (iv) similar use profile (e.g., singulated implants that look and feel the same to the clinician using the device), (v) improved surgical experience due to greater ease of use, equivalent stent delivery, less stent-to-stent or implantation to implantation variability, and less unit-to-unit variability; (vi) better recovery from under-implantation; (vii) no limit to the number of shots or implantation actuations available; and/or (viii) modularity of the design.

BRIEF DESCRIPTION OF THE DRAWINGS

These and other features, aspects, and advantages of the present disclosure will now be described with reference to the drawings of embodiments of the invention, which embodiments are intended to illustrate and not to limit the scope of the disclosure.

FIG. 3A is a close up top perspective view illustrating the introducer assembly of FIG. 2B.

FIG. 6A is a right side view of an embodiment of the internal components of the multiple-implant delivery apparatus of FIG. 2A.

FIG. 6B is a left side view of the internal components of FIG. 6A.

FIG. 7A is a right side view of an embodiment of a frame of the multiple-implant delivery apparatus of FIG. 2A.

FIG. 7B is a left side view of the frame of FIG. 7A.

FIG. 8A is a right side view of an embodiment of a singulation assembly of the multiple-implant delivery apparatus of FIG. 2A.

FIG. 8B is a left side view of the singulation assembly of FIG. 8A.

FIG. 9A is a right side perspective view of an embodiment of a singulation arm of the multiple-implant delivery apparatus of FIG. 2A.

FIG. 9B is a left side view of the singulation arm of FIG. 9A.

FIG. 9C is a left and distal side perspective view of the singulation arm of FIG. 9A.

FIG. 10A is a right side perspective view of an embodiment of a tube set assembly of the multiple-implant delivery apparatus of FIG. 2A.

FIG. 10B is a left side perspective view of the tube set assembly of FIG. 10A.

FIG. 12A is a right side perspective view of an embodiment of an insertion tube of the tube set assembly of FIG. 10A.

FIG. 12B is a left side perspective view of the insertion tube of FIG. 12A.

FIG. 13 is a right side perspective view of an embodiment of a collet holder subassembly of the tube set assembly of FIG. 10A.

FIG. 14 is a perspective view of an embodiment of a singulation tube of the tube set assembly of FIG. 10A.

FIG. 15A is a perspective view of an embodiment of a trocar assembly of the tube set assembly of FIG. 10A.

FIG. 15B is a top view of an embodiment of a trocar of the trocar assembly of FIG. 15A.

FIG. 15C is a top view of an embodiment of a trocar of the trocar assembly of FIG. 15A.

FIG. 15D is a top close-up view of an embodiment of a trocar of the trocar assembly of FIG. 15A.

FIG. 15E-3 shows a plurality of implants loaded on the trocar.

FIGS. 15G-1 and 15G-2 illustrate side views of an alternative embodiment of a trocar having a plurality of bend regions to facilitate singulation of implants.

FIGS. 15H-1 and 15H-2 illustrate side views of an embodiment of a "corkscrew" singulation assembly that includes a spiral wire configured to advance the implants along the trocar.

FIGS. 15I-1 to 15I-4 illustrate side and perspective views of two embodiments of an "ice-cube tray" singulation assembly.

FIGS. 15K-1 to 15K-3 and 15L-1 to 15L-3 illustrate side, top and perspective views of two embodiments of spring wire singulation assemblies.

FIGS. 15N-1 and 15N-2 illustrate side and perspective views of a singulation assembly including plurality of elongated snorkel stents, or implants, positioned along a trocar. FIG. 15N-3 illustrates a side view of an embodiment of one of the elongated snorkel stents.

FIG. 16A is right side view of an embodiment of the internal components of the multiple-implant delivery apparatus of FIG. 2A in a first singulation position.

FIG. 16B is a left side view of the internal components of the multiple-implant delivery apparatus in the first singulation position.

FIG. 16C is right side view of the internal components of the multiple-implant delivery apparatus of FIG. 16A in a second singulation position.

FIG. 16D is a left side view of the internal components of the multiple-implant delivery apparatus in the second singulation position.

DETAILED DESCRIPTION

I. Introduction

Embodiments of systems, devices and methods for delivering multiple (e.g. one, two, three, four, or more) ocular implants of various shapes and sizes are described herein. In the following description, numerous specific details are set forth to provide a thorough understanding of the embodiments; however, one skilled in the relevant art will recognize, based upon the disclosure herein, that the techniques described herein can be practiced without one or more of the specific details, or with other methods, components, materials, etc. In other instances, well-known structures, materials, or operations are not shown or described in detail to avoid obscuring certain aspects.

Reference throughout this description to "one embodiment" or "an embodiment" means that a particular feature, structure, or characteristic described in connection with the embodiment is included in at least one embodiment described herein. Thus, the appearances of the phrases "in one embodiment" or "in certain embodiments" in various places throughout this description are not necessarily all referring to the same embodiments. Furthermore, the particular features, structures, or characteristics may be combined in any suitable manner in one or more embodiments.

Figure 1A:
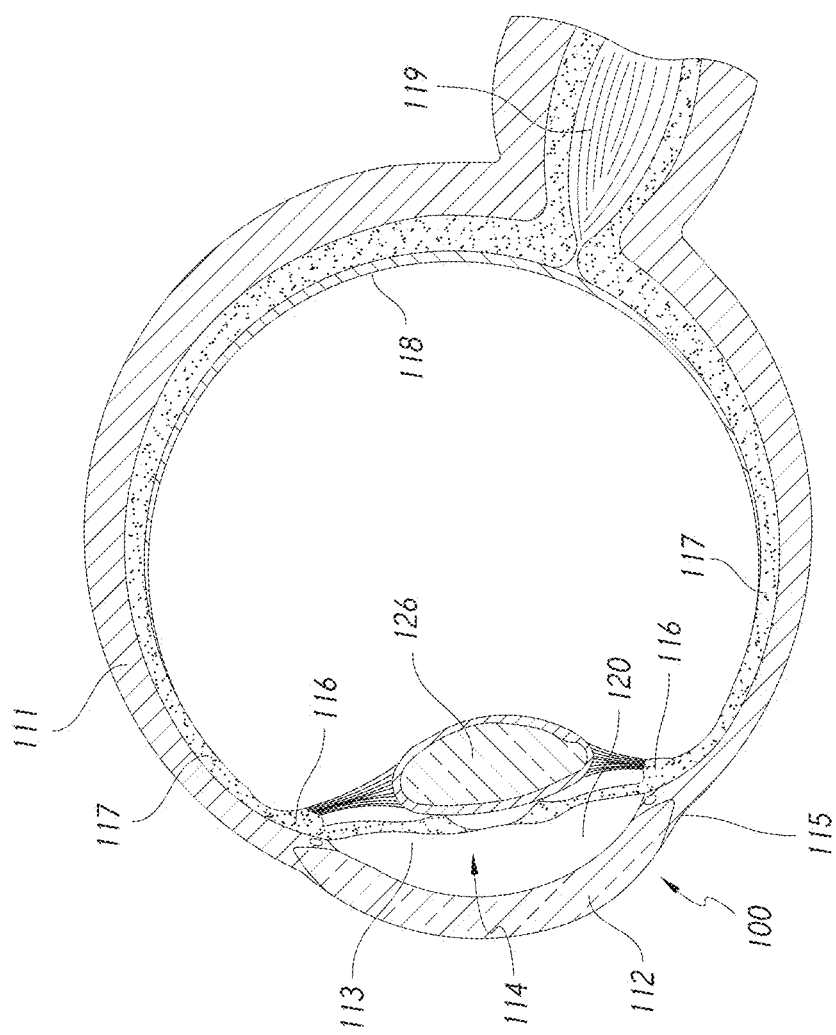
FIG. 1A is a schematic cross-sectional view of an eye.
Figure 1B:
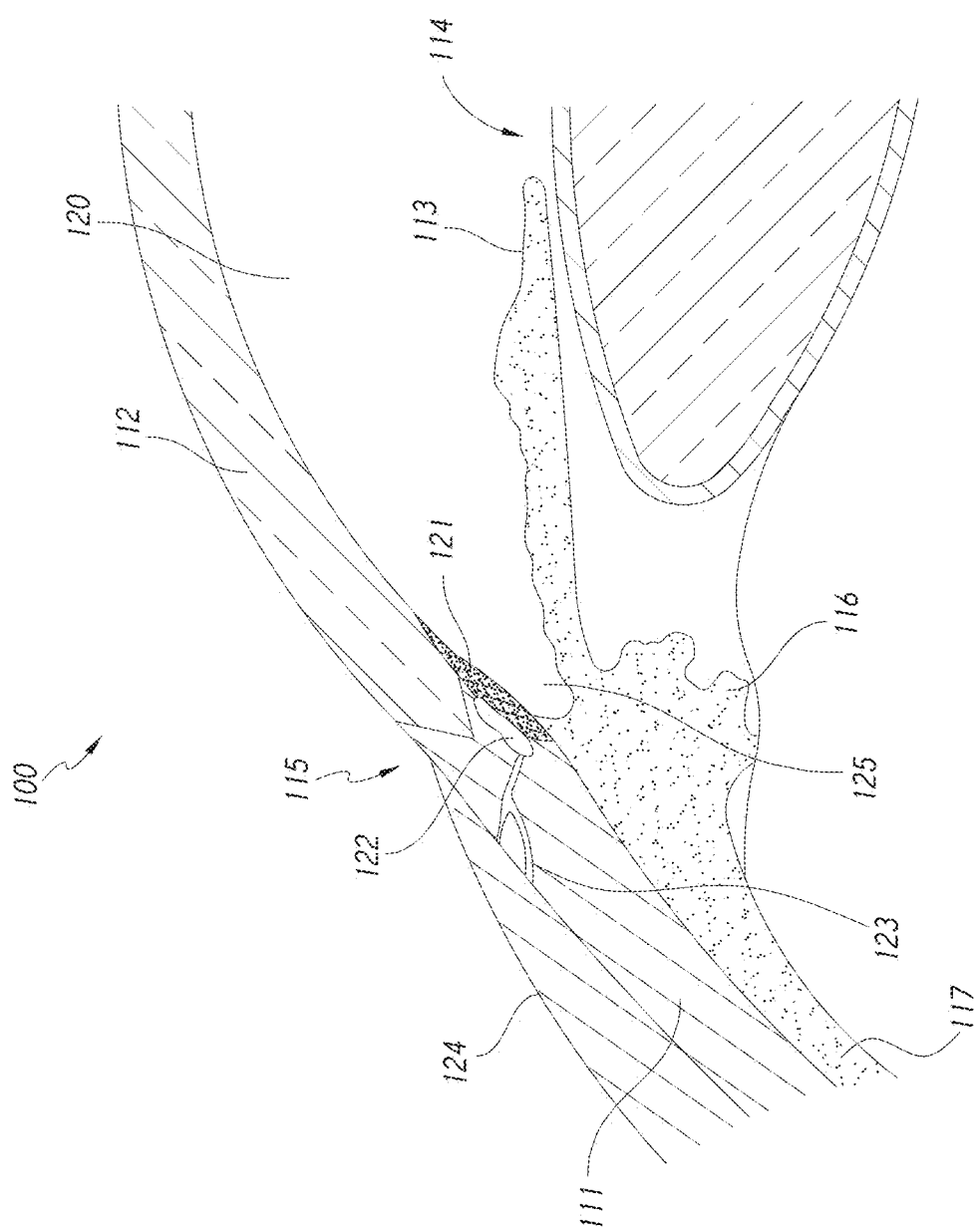
FIG. 1B is an enlarged cross-sectional view of an anterior chamber angle of the eye of FIG. 1A.
Figure 2A:
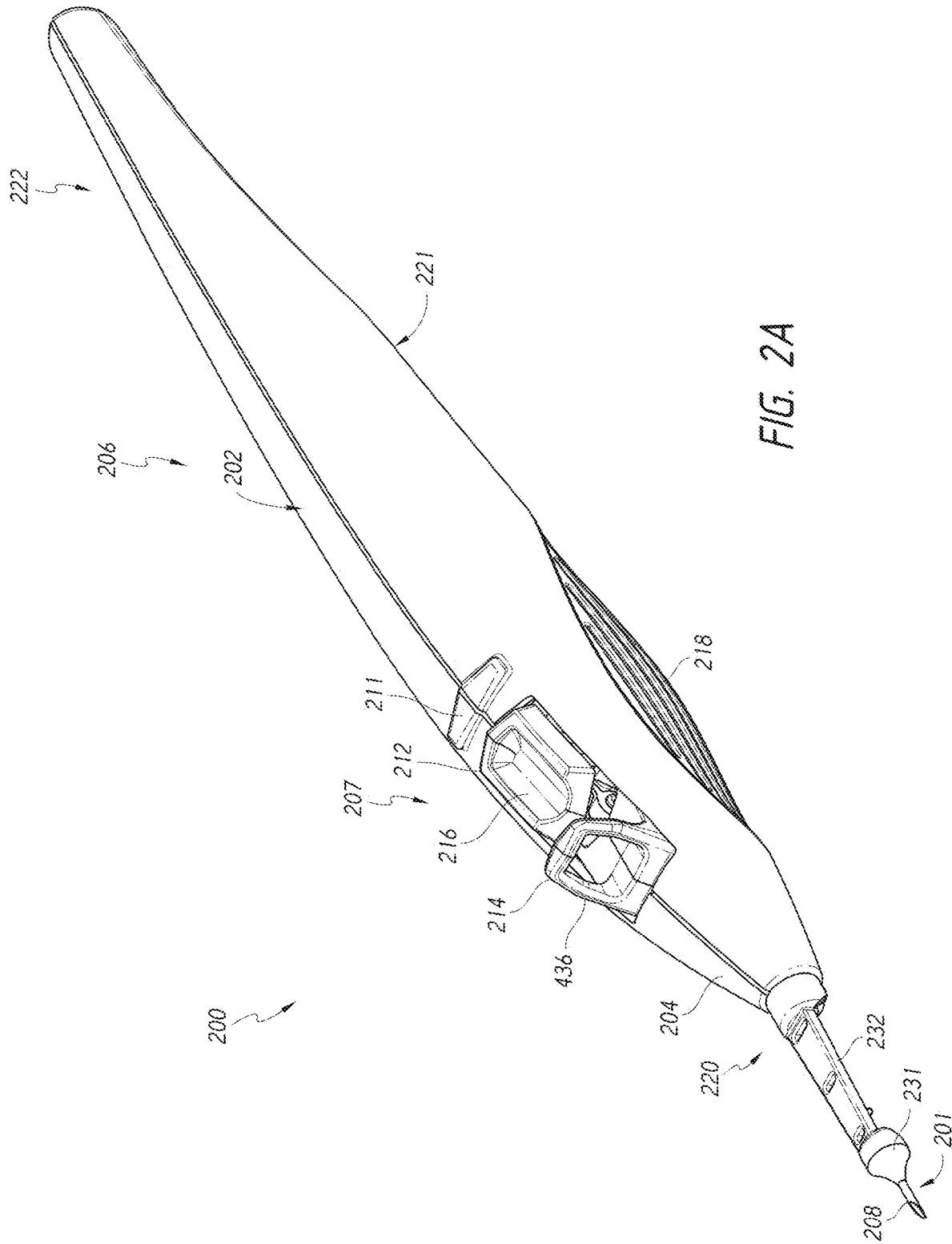
FIG. 2A is a perspective view illustrating an embodiment of a multiple-implant delivery apparatus.
Figure 2B:
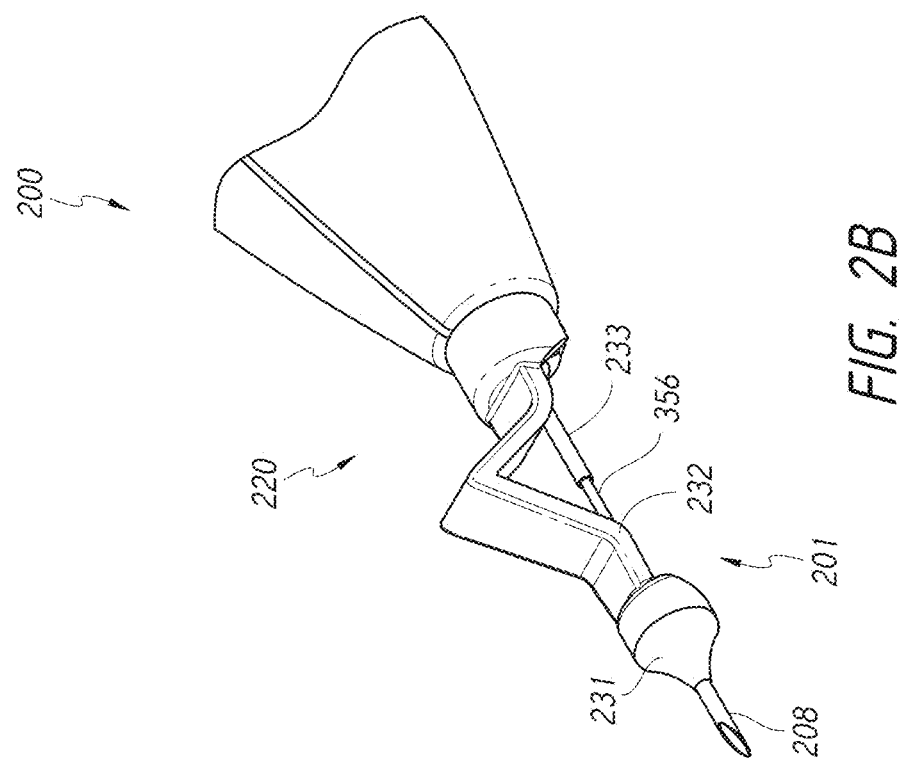
FIG. 2B is a close up perspective view illustrating an embodiment of an introducer assembly of the multiple-implant delivery apparatus of FIG. 2A.
Figure 2D:
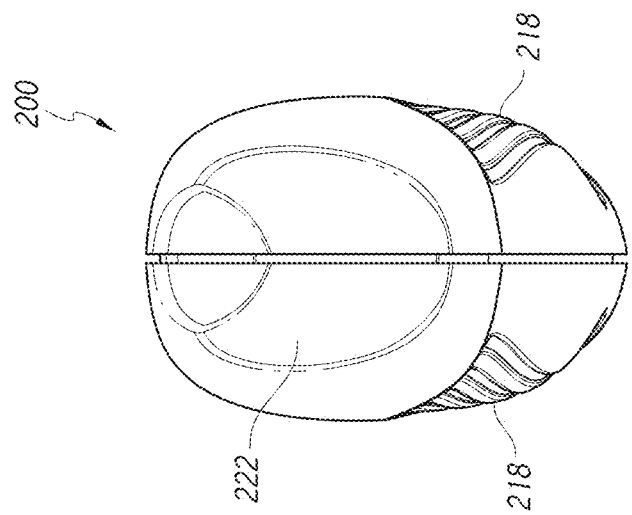
FIG. 2D is a rear view illustrating an embodiment of the multiple-implant delivery apparatus of FIG. 2A.
Figure 2C:
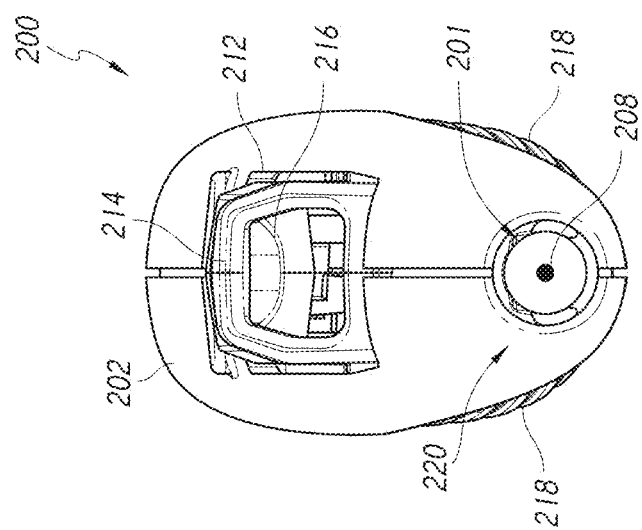
FIG. 2C is a front view illustrating an embodiment of the multiple-implant delivery apparatus of FIG. 2A.
Figure 2E:
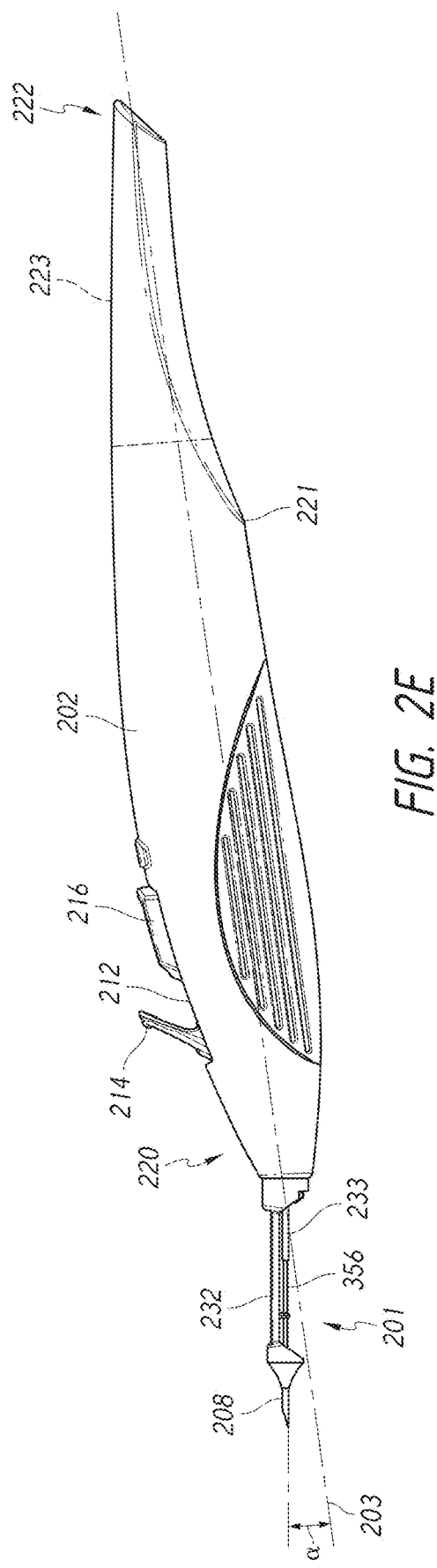
FIG. 2E is a side view illustrating an embodiment of the multiple-implant delivery apparatus of FIG. 2A.
Figure 2F:
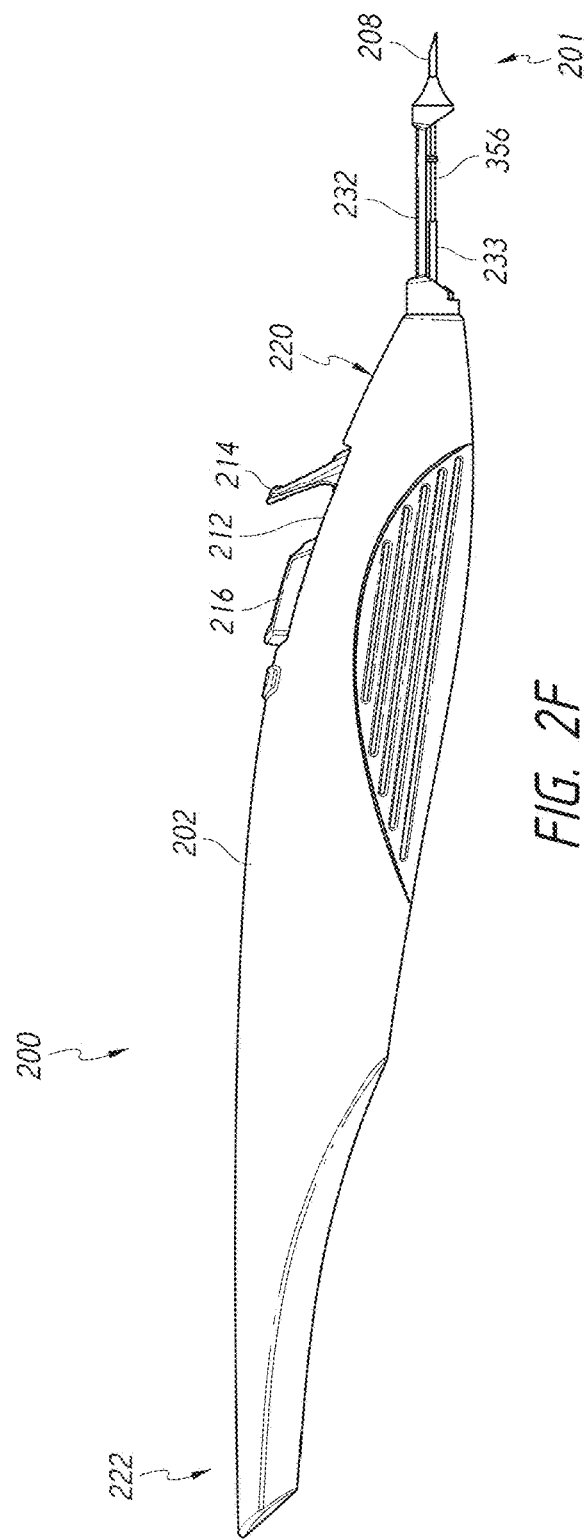
FIG. 2F is another side view illustrating an embodiment of the multiple-implant delivery apparatus of FIG. 2A.
Figure 2G:
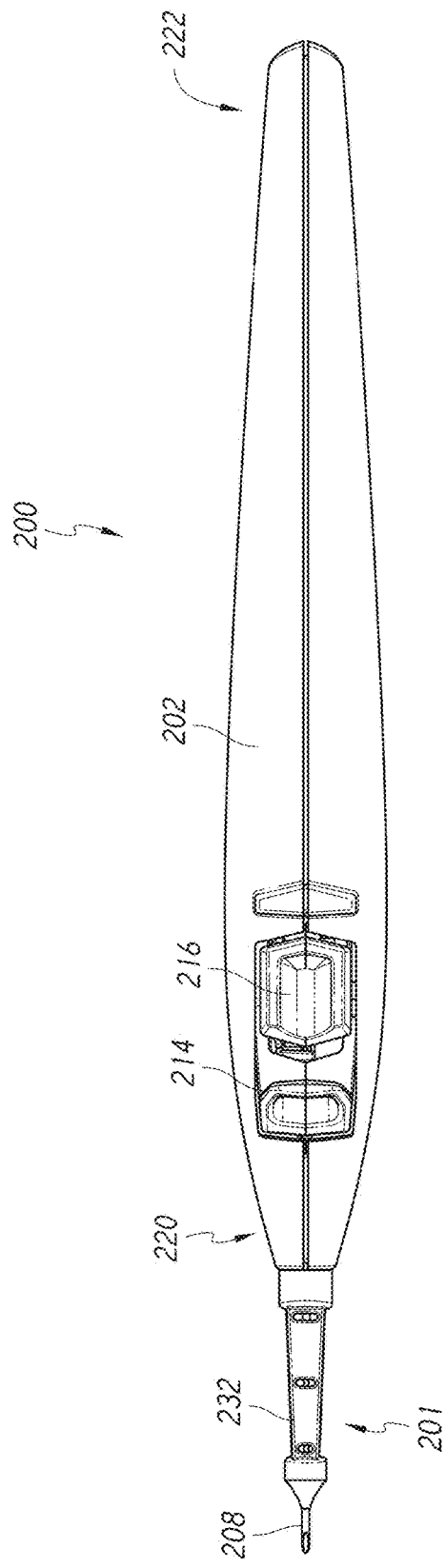
FIG. 2G is a top view illustrating an embodiment of the multiple-implant delivery apparatus of FIG. 2A.
Figure 2H:
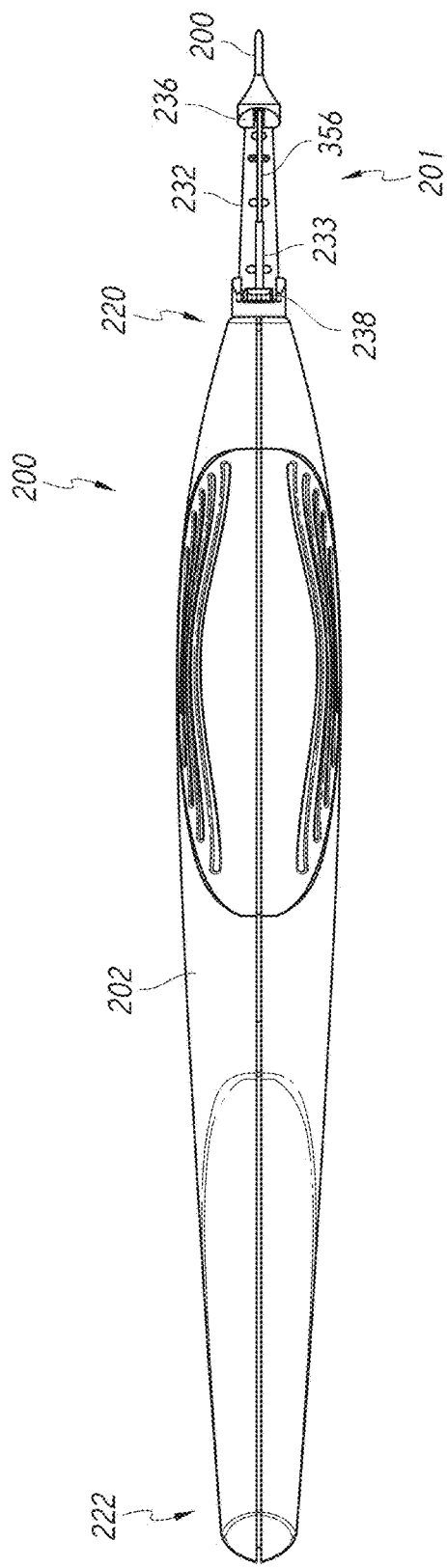
FIG. 2H is a bottom view illustrating an embodiment of the multiple-implant delivery apparatus of FIG. 2A.

FIG. 1A is a cross-sectional view of an eye 100. FIG. 1B is an enlarged sectional view of the eye showing the relative anatomical locations of a trabecular meshwork 121, an anterior chamber 120, and Schlemm's canal 122. With reference to FIGS. 1A and 1B, the sclera 111 is a thick collagenous tissue that covers the entire eye 100 except a portion that is covered by a cornea 112. The cornea 112 is a thin transparent tissue that focuses and transmits light into the eye and through a pupil 114, which is a circular hole in the center of an iris 113 (colored portion of the eye). The cornea 112 merges into the sclera 111 at a juncture referred to as a limbus 115. A ciliary body 116 is vascular tissue that extends along the interior of the sclera 111 from the outer edges of the iris in the limbal region to a choroid 117. The ciliary body 116 is comprised of ciliary processes and ciliary muscle. Ciliary zonules extend from the ciliary processes to a lens 126. The choroid 117 is a vascular layer of the eye 100, located between the sclera 111 and a retina 118. An optic nerve 119 transmits visual information to the brain and is the anatomic structure that is progressively destroyed by glaucoma.

With continued reference to FIGS. 1A and 1B, the anterior chamber 120 of the eye 100, which is bound anteriorly by the cornea 112 and posteriorly by the iris 113 and the lens 126, is filled with aqueous humor. Aqueous humor is produced primarily by the ciliary processes of the ciliary body 116 and flows into the posterior chamber, bounded posteriorly by the lens 126 and ciliary zonules and anteriorly by the iris 113. The aqueous humor then flows anteriorly through the pupil 114 and into the anterior chamber 120 until it reaches an anterior chamber angle 125, formed between the iris 113 and the cornea 112.

As best illustrated by the drawing of FIG. 1B, in a normal eye, at least some of the aqueous humor drains from the anterior chamber 120 through the trabecular meshwork 121 via the canalicular route. Aqueous humor passes through the trabecular meshwork 121 into Schlemm's canal 122 and thereafter through a plurality of collector ducts and aqueous veins 123, which merge with blood-carrying veins, and into systemic venous circulation. Intraocular pressure is maintained by an intricate balance between secretion and outflow of aqueous humor in the manner described above. Glaucoma is, in most cases, characterized by an increased outflow resistance of aqueous humor from the anterior chamber 120, which leads to an increase in intraocular pressure. Fluids are relatively incompressible, and thus intraocular pressure is distributed relatively uniformly throughout the eye 100.

As shown in FIG. 1B, the trabecular meshwork 121 lies adjacent a small portion of the sclera 111. Exterior to the sclera 111 is a conjunctiva 124. Traditional procedures that create a hole or opening for implanting a device through the tissues of the conjunctiva 124 and sclera 111 involve extensive surgery, as compared to surgery for implanting a device, such as described herein, which ultimately resides entirely within the confines of the sclera 111 and cornea 112.

In accordance with some embodiments, an ophthalmic implant system is provided that comprises multiple ocular implants and a delivery instrument for delivering and implanting the multiple ocular implants within eye tissue. The multiple implants may be preloaded within the delivery instrument at the time of assembly, manufacture or packaging. These ocular implants can be configured to drain fluid from the anterior chamber of a human eye into a physiologic outflow pathway, such as Schlemm's canal, aqueous collector channels, episcleral veins, the uveoscleral outflow pathway, the supraciliary space, and/or the suprachoroidal space. The physiologic outflow pathway can be an existing space or outflow pathway (such as Schlemm's canal) or a potential space or outflow pathway (such as the suprachoroidal space). In some embodiments, the ocular implants are configured to be delivered to a location such that the implant communicates or allows fluid to communicate with an outflow pathway. While this and other systems and associated methods and apparatuses may be described herein in connection with glaucoma treatment (e.g., phakic or pseudophakic mild to moderate or refractory open angle glaucoma), the disclosed systems, methods, and apparatuses can be used to treat other types of ocular disorders in addition to glaucoma or to implant other devices (such as pressure sensors or analyte sensors (e.g., glucose sensors)).

While a majority of the aqueous leaves the eye through the trabecular meshwork and Schlemm's canal, it is believed that a significant percentage of the aqueous in humans leaves through the uveoscleral pathway. The degree with which uveoscleral outflow contributes to the total outflow of the eye appears to be species dependent. As used herein, the term "uveoscleral outflow pathway" is to be given its ordinary and customary meaning to a person of ordinary skill in the art (and it is not to be limited to a special or customized meaning), and refers without limitation to the space or passageway whereby aqueous exits the eye by passing through the ciliary muscle bundles located at or near an angle of the anterior chamber and into the tissue planes between the choroid and the sclera, which extend posteriorly to the optic nerve. From these tissue planes, it is believed that the aqueous travels through the surrounding scleral tissue and drains via the scleral and conjunctival vessels, or is absorbed by the uveal blood vessels.

As used herein, the term "supraciliary space" is to be given its ordinary and customary meaning to a person of ordinary skill in the art (and it is not to be limited to a special or customized meaning), and refers without limitation to the portion of the uveoscleral pathway through the ciliary muscle and between the ciliary body and the sclera, and the term "suprachoroidal space" is to be given its ordinary and customary meaning to a person of ordinary skill in the art (and it is not to be limited to a special or customized meaning), and refers without limitation to the portion of the uveoscleral pathway between the choroid and sclera.

The following description will include references to distal and proximal ends of various components and right and left sides of various components. The terms "distal" and "proximal" are to be given their ordinary and customary meaning to a person of ordinary skill in the art (and are not to be limited to a special or customized meaning), and refer without limitation to opposite regions or ends of a particular structure. In some embodiments, the term "distal" is used to refer to a region or end farther away from a person using the systems and devices described herein or performing the methods described herein and the term "proximal" is used to refer to a region or end closer to the person using the systems and devices described herein or performing the methods described herein; however, the meanings of the terms can be swapped.

The term "right side" should be understood to mean the side of the component that, upon assembly, faces the right housing of the multiple-implant delivery apparatus and the term "left side" should be understood to mean the side of the component that, upon assembly, faces the left housing of the multiple-implant delivery apparatus. However, these terms, as well as terms of orientation such as "top," "bottom," "upper," "lower," "front," "rear," and "end" are used herein to simplify the description of the context of the illustrated embodiments. Likewise, terms of sequence, such as "first" and "second," are used to simplify the description of the illustrated embodiments. Because other orientations and sequences are possible, however, the claims should not be limited to the illustrated orientations or sequences. Those skilled in the art will appreciate, upon reading this disclosure, that other orientations of the various components described above are possible.

II. External Components of Multiple-Implant Delivery Apparatus

FIGS. 2A-2H illustrate various views of an embodiment of a multiple-implant delivery apparatus 200, as described in the Brief Description of the Drawings section above. The multiple-implant delivery apparatus 200 can include an external housing 202. The external housing 202 can include a distal end portion 220 and a proximal end portion 222. The external housing 202 can extend between a distal terminus of the distal end portion 220 and a proximal terminus of the proximal end portion 222. As shown in at least FIG. 2A, the proximal end portion 222 of the multiple-implant delivery apparatus 200 can be gradually tapered. In some embodiments, the distal end portion 220 is gradually tapered to form a somewhat nose-shaped cone 204. The delivery apparatus 200 can include an introducer assembly 201 that extends from the cone 204.

In some embodiments, the delivery apparatus 200 includes a forward portion 207 and a rearward portion 206. The rearward portion 206 can include a curved and/or a reduced profile. In some embodiments, an upper portion of the rearward portion 206 of the apparatus 200 is generally rounded towards the proximal end portion 222. In some embodiments, a lower portion of the rearward portion 206 of the apparatus 200 includes a cut-out region that extends from a lower surface of the delivery apparatus 200 towards the proximal end portion 222. For example, the lower portion of the delivery apparatus 200 can have a convex region that extends from the distal end portion 220 towards the proximal end portion 222. The convex region can extend to a lower edge 221 of the lower portion. In some embodiments, the lower portion of the apparatus 200 can include a concave region that extends from the lower edge 221 towards the proximal end portion 222. For example, the concave region of the lower portion can extend upwardly from the lower edge 221 towards the upper portion at the proximal end portion 222. In some configurations, the concave region can define a cutout region. The cutout region can provide a reduced profile to the apparatus 200. In some configurations, the reduced profile allows for the apparatus 200 to include less material, be more lightweight, and/or be more comfortable to hold, among other benefits.

In some embodiments, the external housing 202 includes an opening 212. The opening 212 can provide access to one or more actuators, such as buttons, sliders, and/or levers, among other actuation initiation mechanisms. For example, the delivery apparatus 200 can include a singulation actuator 214 and/or an implant delivery actuator 216. In some embodiments, at least a portion of the singulation actuator 214 and/or the implant delivery actuator 216 extend through the opening 212. In such configurations, the actuators 214, 216 can be easily manipulated and/or accessible by the user. In some embodiments, the singulation actuator 214 facilitates on-demand manual singulation, which, as used herein, can mean isolation, separation, and/or selection of one of the multiple implants for delivery one at a time. The singulation actuator 214 interfaces with internal components (not shown) to effect singulation. In some embodiments, actuation of the implant delivery actuator 216 (e.g., pressing a button extending out of the opening 212) causes the ejection of an implant (e.g., one implant manually singulated as a result of actuation of the singulation actuator 214) out of an introducer tip of the introducer assembly 201 of the delivery apparatus and into a desired first location within the patient's internal eye tissue. In some embodiments, the singulation actuator 214 enables automatic singulation, isolation, and/or selection of respective implants. The implant delivery actuator 216 interfaces with internal components to effect delivery of the implants. In some embodiments, the implant delivery actuator 216 is configured to allow for an infinite number of actuations (e.g., infinite number of button presses) to cause movement of a collet sufficient to deliver an implant out of the introducer tip of the introducer assembly 201. In accordance with several embodiments, the multiple-implant delivery apparatus 200 advantageously generates an implantation impulse to effect implant delivery by capturing and converting the energy used to press the implant delivery actuator 216 (e.g., de-pressing a button). In some embodiments, there is no pre-stored energy prior to actuation of the implant delivery actuator 216, and thus no limit to the number of implant firing sequences or deliveries available.

The multiple-implant delivery apparatus 200 can be advantageously ergonomically shaped for easy gripping and manipulation. In some embodiments, the apparatus 200 can include a general overall shape similar to a conventional writing instrument, such as a fountain pen. In some embodiments, the multiple-implant delivery apparatus 200 can be grasped by the user between the thumb and the middle finger, with the index finger free to manipulate any portion of the apparatus 200. The multiple-implant delivery apparatus 200 may include a finger rest 211, as shown, for example, in FIG. 2A.

In some embodiments, the lower portion of the forward portion 207 of the delivery apparatus 200 can include a plurality of tactile ridges and/or recesses 218. In some embodiments, the tactile ridges and/or recesses 218 provide a textured surface. In some embodiments, the tactile ridges and/or recesses 218 provide the user with a more stable and/or secure gripping surface to grip the delivery apparatus 200 in use.

In some embodiments, as described in more detail below, the external housing 202 is fabricated from a plurality of separate sections. For example, the external housing 202 can include one or more portions, such as half-sections, that can be coupled through various means, such as a snap-fit or press fit configuration or using an adhesive, or can be unitarily formed, among other arrangements. Although snap-fit or press-fit mechanisms of attachment are generally described herein, these attachment mechanisms (for attachment of housing sections to each other and for attachment of members and components residing within the housing) can be replaced, substituted or enhanced with other attachments methods as desired and/or required (e.g., heat stake, glue or other adhesives, screws, welding, retaining by overhangs, and/or positioned by pressing a feature into plastic (with or without heat).

In some embodiments, a plurality of ocular implants is pre-loaded within the multiple-implant delivery apparatus 200 prior to packaging or delivery at the time of manufacture and assembly. In such embodiments, the multiple-implant delivery apparatus 200 can be used to deliver the multiple ocular implants at various desired locations within a mammalian (e.g., human) eye. For example, at least a portion of the introducer assembly 201 can be advanced through a preformed incision or opening in the eye (e.g., an incision in the cornea or limbus of the eye). In another embodiment, at least a portion of the introducer assembly 201 is advanced through external eye tissue (e.g., the cornea or limbus), creating an incision or opening through the eye as it is advanced into the eye tissue. As mentioned above, actuation of the implant delivery actuator 216 can actuate the multiple-implant delivery apparatus 200 and cause the ejection of an implant into a desired first location within the patient's internal eye tissue. In some embodiments, the multiple-implant delivery apparatus 200 can then be repositioned without removing at least a portion of the introducer assembly 201 from the incision and another implant can be delivered to a second location next to or spaced apart from the first location, and additional implants can be delivered to additional locations spaced apart from the second location. In some embodiments, the introducer assembly 201 can be removed from the incision and reinserted through eye tissue through a separate incision in order to deliver the implant to the second implantation site and/or third implantation site. In some configurations, the delivery of the multiple ocular implants advantageously can be performed during an outpatient procedure without extensive surgery.

As mentioned above, in some embodiments, the delivery apparatus 200 includes the introducer assembly 201. The introducer assembly 201 can include (i) an auto-retracting insertion assembly that includes a distal introducer tip 208 and a proximal retraction member 232 and (ii) an insertion tube 356. In some embodiments, at least a portion of the introducer assembly 201 can extend from the distal end portion 220 of the external housing 202 along an axis offset from the longitudinal axis 203 of the delivery apparatus 200. In some embodiments, only the distal introducer tip 208 and/or the insertion tube 356 extends along an axis offset from the longitudinal axis 203. For example, the introducer assembly 201 can extend at an angle α relative to the longitudinal axis 203. In some embodiments, the angle α can be approximately 8 degrees. In some embodiments, the angle α can range from 1-15 degrees, from 1-3 degrees, from 3-5 degrees, from 5-7 degrees, from 7-9 degrees, from 9-11 degrees, from 11-13 degrees, from 13-15 degrees or ranges extending therebetween, or can be any value within the recited ranges.

The angled introducer assembly 201 advantageously provides beneficial ergonomics and more comfortable hand positions of the clinician operator during use. For example, the angled introducer assembly 201 can allow the clinician operator to more easily reach certain portions of the eye. In some embodiments, the angled introducer assembly 201 can allow the clinician operator to rotate the delivery apparatus 200 about an arc to efficiently and more easily access implantation locations spaced apart from each other (e.g., three locations spaced apart at various clock hours (e.g., two clock hours from each other) along a circumference of Schlemm's canal). In some embodiments, the angling of the introducer assembly advantageously allows the clinician operator to sweep out a wider arc to use as much (e.g., up to 50% or more) of the conventional outflow system as possible through a single incision or opening into the eye.

As mentioned above, the introducer assembly 201 can include the insertion tube 356. At least the distal portion of the insertion tube 356 can extend from an opening at a distal terminus of the distal end portion 220 of the external housing 202. In some embodiments, the introducer tip 208 surrounds and/or is guided by the insertion tube 356, which has a lumen. The insertion tube 356 can include a lateral viewing slot described in more detail below (not visible in figure) to facilitate visualization of an implant positioned in a "ready-to-fire" position along a trocar (not visible in figure) extending along and within the lumen of the insertion tube 356. The lateral slot may exhibit any of the structural and/or functional features of the slots described in U.S. Publication No. 2013/0253528 (e.g., Paragraphs [0118]-[0125] and FIG. 19). In some embodiments, the insertion tube 356 can assist in more easily accessing certain portions of the eye. In some embodiments, a plurality of ocular implants can be preloaded into the insertion tube 356 along the trocar.

Figure 3B:
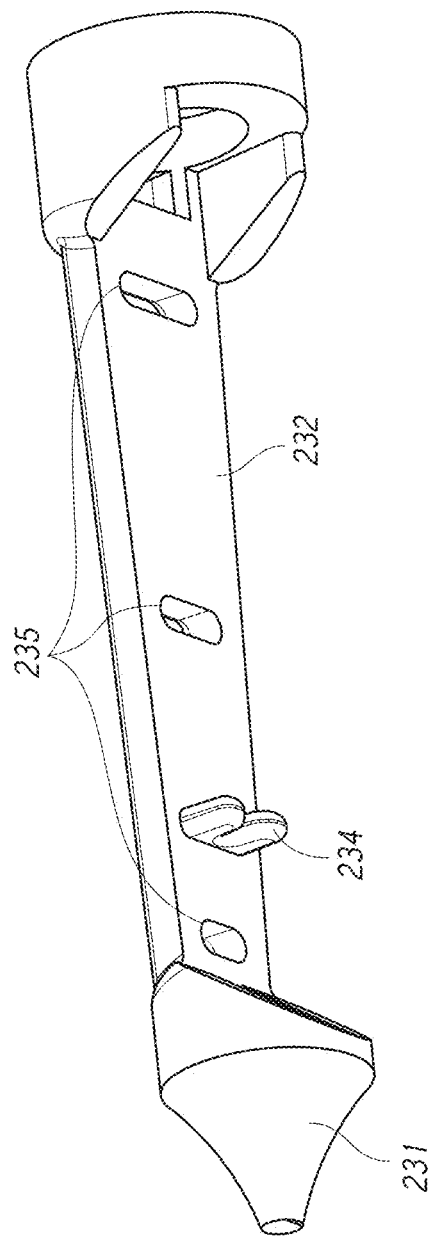
FIG. 3B is a close-up bottom perspective view illustrating the introducer assembly of FIG. 2B.

As shown in at least FIGS. 3A and 3B, the proximal retraction member 232 of the auto-retracting insertion assembly can extend from a mating component on the distal terminus of the distal end portion 220 of the external housing 202. The proximal end of the proximal retraction member 232 may be fixedly or removably coupled to the mating component on the distal terminus of the distal end portion 220. The distal end of the retraction member 232 includes a generally cone-shaped interface component 231 specifically designed to interface with a boundary of a pre-formed incision or opening in eye tissue (e.g., cornea or limbus) and prevent continued advancement of the proximal retraction member within the eye. This interface component 231 of the retraction member 232 may be advantageously shaped and sized to facilitate insertion within incisions or openings of between 1 mm and 4 mm (e.g., between 1 mm and 3 mm, between 2 mm and 4 mm, less than 2 mm).

In some embodiments, the distal introducer tip 208 forms the distal end portion of the auto-retracting insertion assembly. For example, as shown in the illustrated embodiments, the distal introducer tip 208 can extend from the interface component 231 of the retraction member 232. In some embodiments, the distal introducer tip 208 is integrally formed with the proximal retraction member 232. For example, the proximal end portion of the distal introducer tip 208 may reside within and be fixedly coupled to (e.g., adhered to, molded to) the interface component 231 of the retraction member 232. The distal introducer tip 208 can include a hollow needle, among other types of needles. For example, the distal introducer tip 208 can include an interior lumen that can allow the insertion tube 356 to pass therethrough. In some embodiments, the length of the retraction member 232 can be sized such that at least a portion of the distal introducer tip 208 is configured to always surround at least a portion of the length of the insertion tube 356, thereby maintaining coaxial alignment between the insertion tube 356 and the distal introducer tip 208. The distal tip of the distal introducer tip 208 may be beveled to facilitate insertion within eye tissue.

In some embodiments, the proximal retraction member 232 includes a flexible material, such as silicone elastomer, plastic, rubber, or other materials. The proximal retraction member 232 can be configured to bend in use. The proximal retraction member 232 may include multiple openings 235 positioned along its length at locations designed to facilitate bending of the retraction member 232 in a desired or predetermined bending configuration. As shown best in FIG. 3B, a bottom side of the proximal retraction member 232 may include a tube engagement member 234 configured to engage and receive the insertion tube 356. The tube engagement member 234 may include two feet as shown with a slot formed between the two feet. The slot may have a general curve as shown or may have a keyhole shape or configuration. In some embodiments, the tube engagement member 234 is positioned and configured to cause bending of the proximal retraction member 234 in a particular configuration. The proximal retraction member 232 may also be pressed at a location corresponding to the location of the tube engagement member 234 to force the slot of the tube engagement member 234 onto and around the tube, thereby resulting in greater force for insertion. In various embodiments, the column of the proximal retraction member 232 has a tapered width and/or a uniform width. In some embodiments, the proximal retraction member 232 is tapered in a distal direction. For example, the proximal retraction member 232 can include a width that is wider on a proximal side than at a distal side of the proximal retraction member 232. The shape of the proximal retraction member 232 can desirably allow the introducer assembly 201 to be more smoothly inserted into the eye.

In some embodiments, when the delivery apparatus 200 enters the eye, such as at the anterior chamber, at least a portion of the introducer assembly 201 is advanced to the trabecular meshwork. When the interface component 231 of the proximal retraction member 232 reaches a portion of the eye, such as the trabecular meshwork, the retraction member 232 can yield and/or buckle to form a bent or curved "inchworm" configuration. For example, the distal side of the retraction member 232 can slide rearwardly along the insertion tube 356 and a central portion of the retraction member 232 can extend radially outwardly from the distal introducer tip 208 (see FIG. 2B). The retraction member 232 is specifically engineered so that, when the clinician operator is entering the anterior chamber, there is enough force transmitted to push the distal introducer tip 208 and insertion tube 356 into and through the incision formed in the eye tissue (e.g., corneal incision) and into the anterior chamber and yet when the clinician operator wants to advance the insertion tube 356 across the anterior chamber to the trabecular meshwork, the proximal retraction member 232 buckles and yields to "retract" the distal introducer tip 208 and allow the insertion tube 356 to be advanced across the anterior chamber without being surrounded by the distal introducer tip 208. In some embodiments, the forces generated by components of the retraction member 232 are just high enough to get the distal introducer tip 208 through the wound and then the interface component 231 of the retraction member 232 bottoms out on the wound and buckles. The force profile may advantageously be linear or substantially linear or substantially constant during "retraction" (e.g., from the point of buckling or bending to the point of full insertion into the eye). In other embodiments, the force profile may transition from very high during insertion to almost zero through use of a mechanical lockout that would be locked during insertion until some part of the distal introducer tip 208 bottomed out (e.g., on the surface of the cornea) and then the mechanical lockout would be releases, allowing the retraction member 232 to bend and allowing the force to drop to almost zero.

In some embodiments, when the retraction member 232 slides along an exterior surface of the insertion tube 356, the insertion tube 356 can slide through at least a portion of the distal introducer tip 208 and/or the interface component 231 of the retraction member 232 to facilitate delivery of one or more implants according to one or more methods described herein.

In some embodiments, the interface component 231 of the retraction member 232 advantageously acts as a stop for the insertion tube 356 against the cornea or other portion of the eye. In some embodiments, the interface component 231 of the retraction member 232 advantageously helps to seal, limit or prevent leakage of aqueous humor from the anterior chamber of the eye as the interface component 231 sits against the insertion site.

In some embodiments, the introducer assembly 201 includes a stop member 233. In some embodiments, the stop member 233 surrounds at least a portion of the insertion tube 356 extending out of the exterior housing 202 of the delivery apparatus 200. In some embodiments, the insertion tube 356 extends out of a distal end of the stop 233. The stop 233 can stop the retraction member 232 from sliding further proximally along the insertion tube 356 in use. For example, as the interface component 231 of the retraction member 232 slides in a proximal direction, the stop 233 can contact at least a proximal flange portion of the interface component 231. The contact between the stop 233 and the interface component 231 can limit or prevent further proximal movement of the retraction member 232. The stop 233 may advantageously help support the insertion tube 356, thereby keeping the insertion tube in place and inhibiting movement of the insertion tube 356. In some embodiments, distal component 236 of the retraction member 232 can be coupled with distal component 238 of the retraction member 232 to maintain the retraction member 232 in a retracted position (e.g., for training or rethreading an implant back on the trocar outside the eye).

III. Internal Operation of Multiple-Implant Delivery Apparatus

Figure 4:
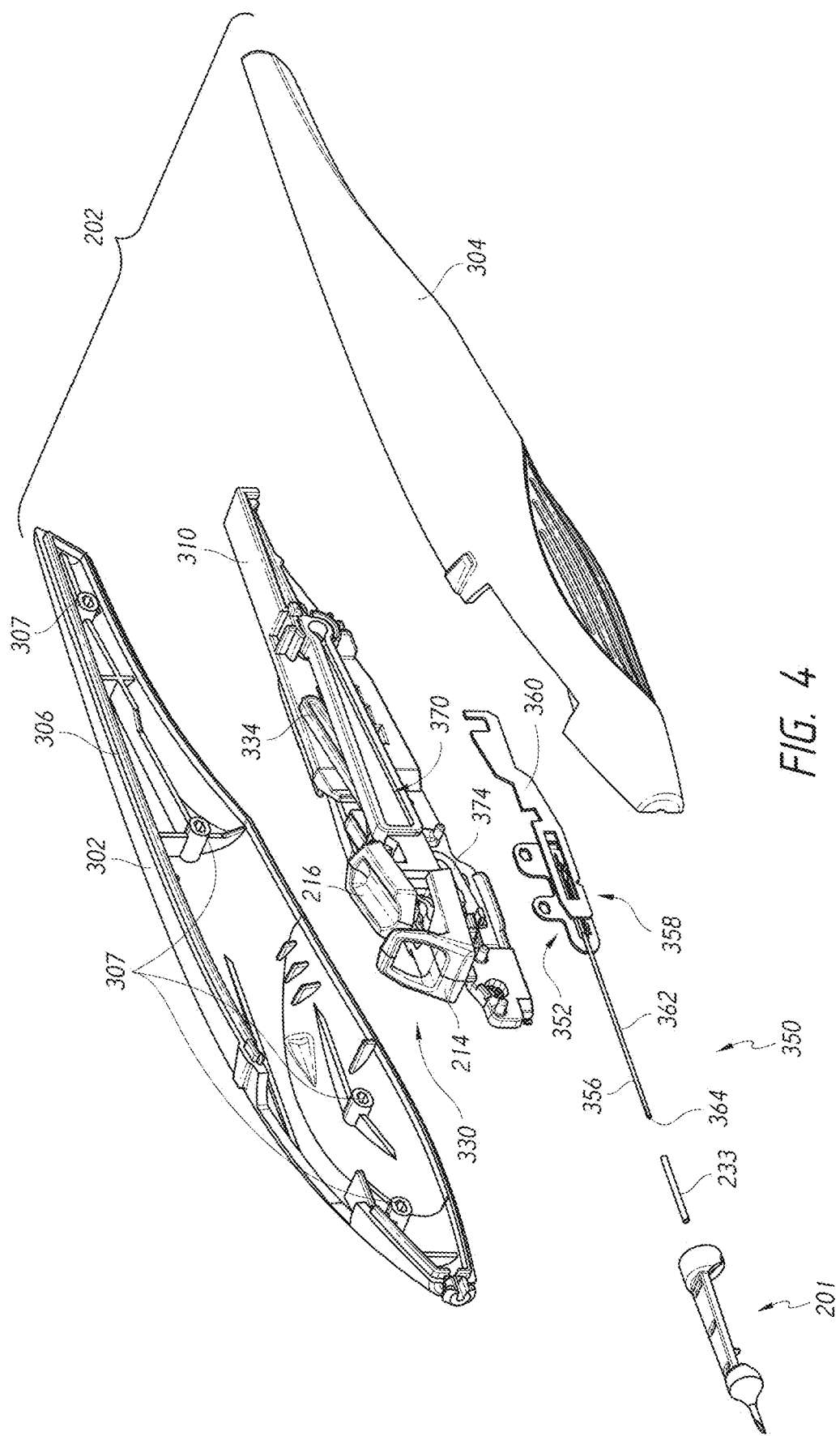
FIG. 4 is a perspective exploded view of the multiple-implant delivery apparatus of FIG. 2A.

FIG. 4 is an exploded perspective view of the multiple-implant delivery apparatus 200. The external components of the multiple-implant delivery apparatus 200 include a left housing 302, a right housing 304, and the introducer assembly 201 (described above).

As shown, the external housing 202 is formed of two separate half-sections (left housing 302 and right housing 304). The left housing 302 can include a left section of the opening 212 and the right housing 304 can include a right section of the opening 212. In alternative embodiments, the external housing 202 could be separated into top and bottom half-sections instead of right and left half-sections. In yet other alternative embodiments, the external housing 202 is formed of more than two sections configured to be attached together to form a contiguous unit.

Figure 5A:
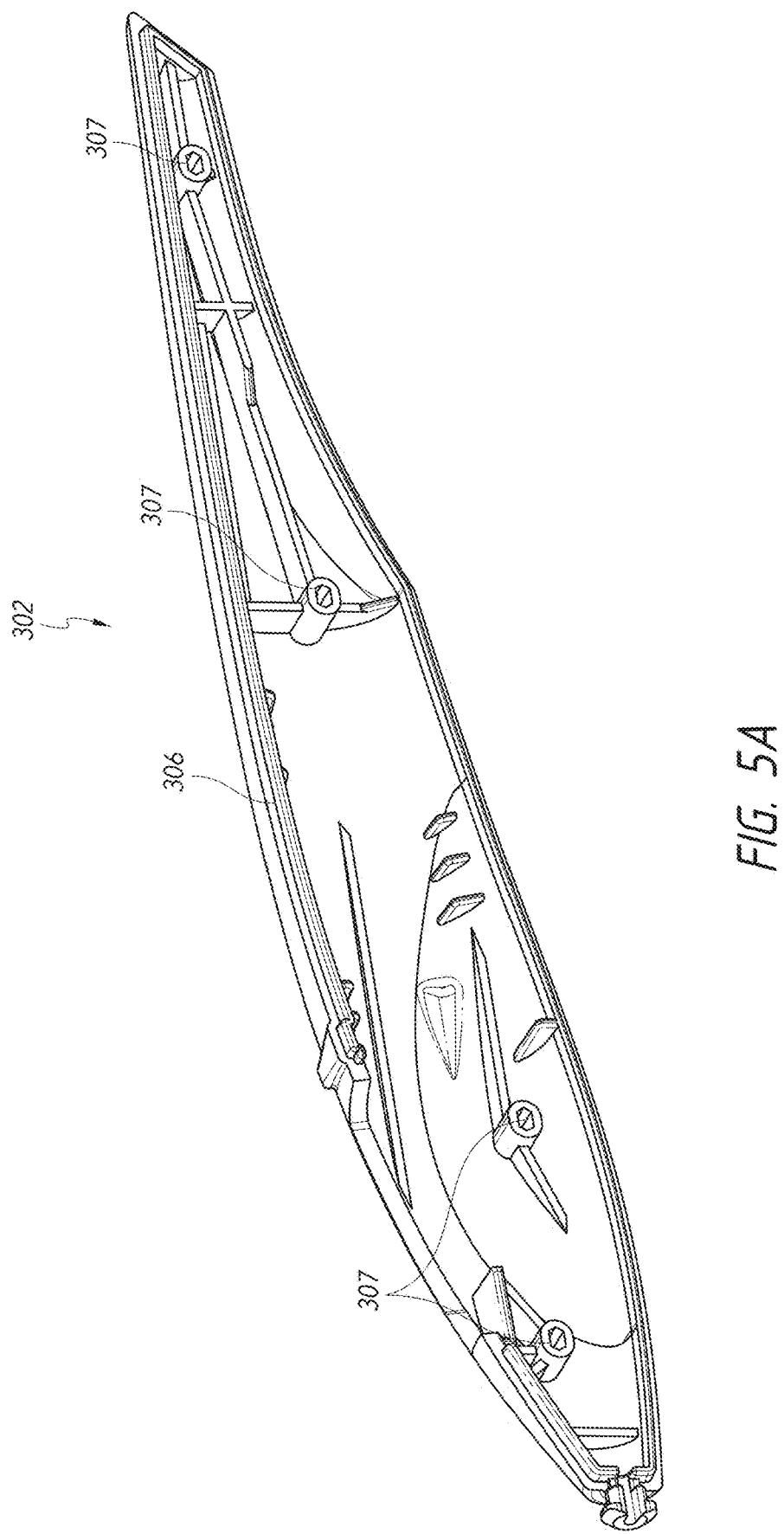
FIG. 5A is a side perspective view of an embodiment of a left housing of the multiple-implant delivery apparatus of FIG. 2A.
Figure 5B:
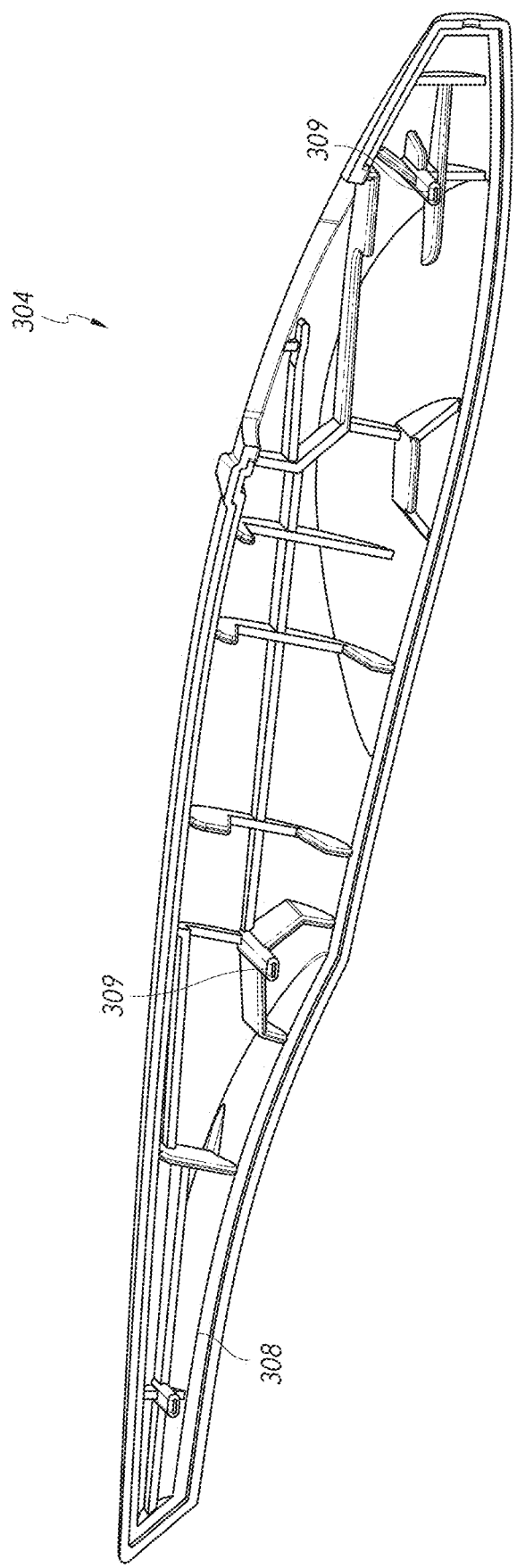
FIG. 5B is a side perspective view of an embodiment of a right housing of the multiple-implant delivery apparatus of FIG. 2A.

FIG. 5A illustrates a side perspective view of the left housing 302 and FIG. 5B illustrates a side perspective view of the right housing 304. The left housing 302 and the right housing 304 can be assembled to form a unitary body. The left housing 302 and the right housing 304 can be coupled through various means, such as a snap-fit or press fit configuration or using an adhesive, or can be unitarily formed, among other arrangements. The left housing 302 and/or the right housing 304 can include various mating features to couple the left and right housings 302, 304 and/or features for receiving, supporting and/or aligning the internal components of the multiple-implant delivery apparatus 200. For example, the left housing 302 can include a rim 306 that protrudes away from the outer surface of the left housing 302 and extends along at least a portion of an inner perimeter of the left housing 302. The rim 306 is configured to couple with a corresponding recess 308 that extends along at least a portion of an inner perimeter of the right housing 304.

In some embodiments, the left housing 302 includes a plurality of snap-fit or press-fit receiving members 307. One or more of the snap-fit or press-fit receiving members 307 can form receptacles that are configured to align with and to receive one or more snap-fit or press-fit engaging members 309 (e.g., flanges, protrusions) that extend from the right housing 304 or other component of the multi-implant delivery apparatus 200. One or more of the snap-fit or press-fit receiving members 307 and/or one or more of the snap-fit or press-fit engaging members 309 can be configured to pass through an opening formed in at least one of the internal components of the multiple-implant delivery apparatus 200 to support the internal components within the external housing 202. Other configurations are contemplated such as the left housing 302 and/or the right housing 304 having one or more of the mating features described above (e.g., the right housing 304 can include the snap-fit or press-fit receiving members 307 and the left housing 302 can include the snap-fit or press-fit engaging members 309. The left and right housings 302, 304 can be coupled to surround at least a portion of the internal components of the multiple-implant delivery apparatus 200. In certain embodiments, there is an audible click when snap-fit receiving members 307 and snap-fit engagement members 309 and/or the rim 306 and recess 308 are fully engaged. In alternative embodiments, the left and right housings 302, 304 can be connected or otherwise coupled to each other via adhesion, screws, glue, welding (e.g., sonic welding), and/or the like. In some embodiments, a proximal tail 223 of the multiple-implant delivery apparatus 200 may be configured to detach from and reattach to the rest of the body (e.g., as indicated by the dashed line) via snap-fit or press-fit coupling mechanisms or configurations.

In various embodiments, the left housing 302 and the right housing 304 are composed of any rigid or semi-rigid material, such as plastic, polymer, metal, composites, or the like. In one embodiment, the left housing 302 and the right housing 304 are molded from Lexan® polycarbonate. In some embodiments, at least a portion of the left housing 302 and/or the right housing 304 is composed of a flexible material, such as silicone or similar elastomeric or flexible polymers (including but not limited to acrylonitrile butadiene styrene (ABS), a blend of polycarbonate and ABS, polystyrene, polypropylene, and/or polyethylene.

With reference to FIGS. 4 and FIGS. 6A-6B, the internal components of the multiple-implant delivery apparatus 200 include a frame 310, a singulation assembly 330 (including the singulation actuator 214, a singulation biasing member 332, and a singulation arm 334), a tube set assembly 350 (including an insertion tube subassembly 352 having an insertion tube carrier 354 and an insertion tube 356), a collet holder assembly 358 having a collet holder 360 and a singulation tube 362, and a trocar assembly 364), an actuation assembly 370 (including the implant delivery actuator 316, an actuator biasing member 372, and an actuator arm 374), and the introducer assembly 201 (described above).

The internal components can be secured to or within the external housing 202 during assembly of the multiple-implant delivery apparatus 200 using various methods of fixation (e.g., adhesion, bonding, gluing, snap-fitting, and the like). The interaction of the internal components and the operation of the multiple-implant delivery apparatus 200 will be discussed in more detail later.

In certain embodiments, the multiple-implant delivery apparatus 200 is disposable or configured for a single use and includes one or more safety mechanisms that prevent reuse. For example, the safety mechanism can be an internal component that renders the instrument inoperable if re-sterilized. In accordance with several embodiments, the safety mechanism is that plastic parts do not survive sterilization with an autoclave. In other embodiments, the multiple-implant delivery apparatus 200 is reloaded with implants, sterilized, and re-used on the same or a different patient.

A. Frame

FIGS. 7A and 7B illustrate an example of the frame 310. The frame 310 can have an overall shape that corresponds to the shape of the external housing to allow the frame 310, among the other internal components of the multiple-implant delivery apparatus 200, to fit and be secured within the external housing 202. For example, the frame 310 can have a proximal portion 402, a distal portion 404, a left side 403, and a right side 405. The proximal portion 404 can be raised relative to the distal portion 404.

The frame 310 can include certain attachment features that secure the frame 310 to the external housing. As shown in FIGS. 7A and 7B, the frame 310 can include one or more openings, slots, receptacles or apertures 406. The openings 406 can be positioned along various portions of the frame 310, such as along the distal portion 404 and/or the proximal portion 402. The frame 310 can include one, two, three, four, five, six, or seven or more openings 406. The openings 406 can pass entirely through a width of the frame 310. The openings 406 can allow certain attachment features, such as the snap-fit or press-fit receiving members 307 and/or the snap-fit or press-fit engagement members 309 to pass through the frame 310 and secure the frame 310 within the external housing 202. Such configurations can help to limit movement of the frame 310 within the external housing 202 when assembled. In some embodiments, the frame 310 includes certain attachment members or features that are configured to secure other internal components to the frame 310.

In some embodiments, at least one of the left and right sides 403, 405 of the frame 310 includes an implant delivery actuator receptacle 408. The receptacle 408 can be shaped to receive and/or secure at least a portion of the implant delivery actuator 216, as described in more detail below. The receptacle 408 can have a generally circular shape, a generally rectangular shape, or other shapes. The shape of the receptacle 408 can allow the implant delivery actuator 216 to pivot about a center of the receptacle 408. The receptacle 408 can be defined by at least one arc-shaped wall that extends outwardly from the right side 405 of the frame 310. The receptacle 408 can be positioned at the proximal portion 402 of the frame 310. In some embodiments, the receptacle 408 is positioned on at least a portion of an upper region of the proximal portion 402 of the frame 310.

As shown, a proximal terminus end of the proximal portion 402 of the frame 310 can include an implant delivery actuator slot 410. The implant delivery actuator slot 410 can be configured to receive and/or secure at least a portion of the implant delivery actuator 216, such as a proximal end portion and/or a proximal terminus end of the actuator 216. The implant delivery actuator slot 410 can be shaped such that at least a portion of the implant delivery actuator 216 sits within the slot 410. The slot 410 can be defined by one or more prongs. For example, at least a first prong 410A can be formed along a wall of the frame 310 and at least a second prong 410B can be spaced apart from the first prong to define the slot 410. The slot 410 can be shaped to limit or prevent lateral movement of the implant delivery actuator 216 when the actuator is assembled to the frame 310. In some embodiments, an upper wall of the slot 410 advantageously helps to limit or prevent upward movement of the proximal portion of the implant delivery actuator 216. Thus, as explained below, in some embodiments, only a portion of the implant delivery actuator 216 rotates about the receptacle 408 when the implant delivery actuator 216 is manipulated.

In some embodiments, the frame 310 includes a singulation frame slot 412. The singulation frame slot 412 can assist in singulation of one or more implants loaded in the multiple-implant delivery apparatus 200. In some embodiments, the singulation frame slot 412 is positioned at the proximal portion 402 of the frame 310. The singulation frame slot 412 may be positioned on the right side 405 of the frame 310. The singulation frame slot 412 can pass entirely through the frame 310.

The singulation frame slot 412 can be shaped to receive at least a portion of the singulation arm 334 (e.g., proximal singulation slot member 456 as shown in FIGS. 9A-9C). In some embodiments, the singulation frame slot 412 includes a plurality of platforms. For example, the singulation frame slot 412 can include one, two, three, four, five, six, seven, eight, or nine or more platforms.

As shown in FIGS. 7A and 7B, the singulation frame slot 412 can include a first platform 414A, a second platform 414B, a third platform 414C, and a fourth platform 414D. The first, second, third, and fourth platforms 414A, 414B, 414C, 414D can extend from an internal distal side of the slot 412. In some embodiments, proximal and/or distal ends of each of the first, second, third, and fourth platforms 414A, 414B, 414C, 414D are positioned offset from one another. For example, the distal end of the first platform 414A can be positioned distal of the distal end of the second platform 414B, the distal end of the second platform 414B can be positioned distal of the distal end of the third platform 414C, the distal end of the third platform 414C can be positioned distal of the distal end of the fourth platform 414C. Similarly, the proximal end portion of the first platform 414A can be positioned proximal of the proximal end portion of the second platform 414B, the proximal end portion of the second platform 414B can be positioned proximal of the proximal end portion of the third platform 414C, the proximal end portion of the third platform 414C can be positioned proximal of the proximal end portion of the fourth platform 414C. As explained in more detail below, the positioning of each of the first, second, third, and fourth platforms 414A, 414B, 414C, 414D can desirably allow at least a portion of the singulation arm 334 to move along one platform to the next platform in an arc-like manner during singulation of an implant.

In some embodiments, the proximal end portion of at least one of the first, second, third, and fourth platforms 414A, 414B, 414C, 414D is at least partially tapered or slanted in a distal direction. The sharp tapered or slanted portions of the proximal end portions of at least one of the first, second, third, and fourth platforms 414A, 414B, 414C, 414D can allow the singulation arm 334 to slide between adjacent platforms without requiring as much force perpendicular to the platform. In some embodiments, the tapered or slanted portions include one, two, or more tapered regions to allow the distal singulation arm collet holder member 458 to return to its original position.

In some embodiments, the frame 310 includes a singulation frame arm slot 416. The slot 416 can be generally L-shaped, among other shapes. The slot 416 can be positioned in at least a portion of the distal portion 404 of the frame 310. In some embodiments, the singulation frame arm slot 416 is sized and adapted to receive and/or support at least a portion of the singulation arm 334. The slot 416 can allow the singulation arm 334 to slide and/or rotate within the slot 416.

In some embodiments, the frame 310 includes an actuator arm attachment member 418. The actuator arm attachment member 418 can extend outwardly from a side of the frame 310, such as from the right side 405 of the frame 310. In some embodiments, the actuator arm attachment member 418 is positioned on the distal portion 404 of the frame 310. In some embodiments, the actuator arm attachment member 418 is configured to secure the actuator arm 374 by passing through the actuator arm connection opening 542 in the actuator arm 374 when the actuator arm 374 is assembled with the frame 310. In some embodiments, the actuator arm attachment member 418 is sized and/or configured to snap to or otherwise reside within at least a portion of the actuator arm 374, such as the actuator arm connection opening 542. As explained in more detail below, the actuator arm 374 can be configured to pivot about the actuator arm attachment member 418.

In some embodiments, the frame 310 includes at least one tube set assembly attachment member 420. In the illustrated embodiment, the frame 310 includes at least two tube set assembly attachment members 420A, 420B and can optionally include additional tube set assembly attachment members 420. The tube set assembly attachment members 420 can extend outwardly from a side of the frame 310, such as from the right side 405 of the frame 310. In some embodiments, the tube set assembly attachment members 420 is positioned on the distal portion 404 of the frame 310. In some embodiments, the tube set assembly attachment members 420 is configured to secure the tube set assembly 350 within the external housing 202 by passing through at least an opening 470 in at least one component of the tube set assembly 350, such as the insertion tube carrier 354, when at least a portion of the tube set assembly 350 is assembled with the frame 310. In some embodiments, the tube set assembly attachment members 420 is sized and/or configured to snap to or otherwise reside within at least a portion of the tube set assembly 350, such as the opening 470.

In some embodiments, the frame 310 includes an actuator arm protrusion platform 422. The actuator arm protrusion platform 442 can extend outwardly from a side of the frame 310, such as from the right side 405 of the frame 310. In some embodiments, the actuator arm protrusion platform 422 is positioned on the distal portion of the frame 310. In some embodiments, the actuator arm protrusion platform 422 is configured to support at least a portion of the actuator arm 374, such as a distal facing side 548A, and an upwardly facing side 548B, as explained in more detail below. In some embodiments, the actuator arm protrusion member 544 is configured to rest on at least a portion of the platform 422.

In some embodiments, the frame 310 includes a singulation actuator track 424. The singulation actuator track 424 can define a space formed between an upper track member 424A and a lower track member 424B that extend outwardly from at least one side of the frame 310, such as the left side 403. The singulation actuator track 424 can be configured to receive and/or secure at least a portion of the singulation actuator 214, such as a proximal portion of the singulation actuator 430. The singulation actuator track 424 can include a singulation track extension portion 426 that extends laterally outwards from the lower track member 424B. The singulation track extension portion 426 can include an upwardly extending portion that extends upwardly from an outer end of the extension portion 426 to help to secure the singulation actuator 214 to the frame 310. The extension portion 426 can help limit or prevent lateral and/or distal movement of the singulation actuator 214 relative to the frame 310. As shown in at least FIG. 7B, the right side of the singulation frame adjustment slot 412 can be positioned within the singulation actuator track 424 on the left side 403 of the frame 310.

B. Singulation Assemblies and Methods

FIGS. 8A and 8B illustrate an example of the singulator assembly 330. The singulation assembly 330 can include the singulation actuator 214, the singulation biasing member 332, and/or the singulation arm 334, among other components. The singulation actuator 214 can include a proximal portion 430, a central transition region 432, and a distal portion 434. The proximal portion 430 can be generally trapezoidal shaped, rectangular, square, or other shape. The proximal portion 430 can be configured to be secured within the singulation actuator track 424 on a side of the frame 310 when assembled. The securement between the proximal portion 430 and the singulation actuator track 424 can help to limit lateral movement of the singulation actuator 214, yet allow proximal movement of the singulation actuator 214. For example, in some embodiments, the singulation actuator track 424 is configured to allow the singulation actuator 214 to slide in a proximal-distal direction along the track 424.

In some embodiments, at least a portion of the proximal portion 430, such as a top surface of the proximal portion 430 is positioned at a higher elevation than at least a portion of the distal portion 434, such as a top surface of the distal portion. The proximal portion 430 and the distal portion 434 can be connected by the central transition region 432. The central transition region 432 can smoothly transition between the proximal portion 430 and the distal portion 434. The central transition region 432 can include a straight portion and a tapered portion that gradually transitions downwardly from the straight portion to the distal portion 434.

In some embodiments, the distal portion 434 includes an actuator lever, such as a handle 436. The handle 436 can extend upwardly and/or rearwardly from the distal-most terminus end of the distal portion 434. In some embodiments, the handle 436 is configured to extend through the opening 208 of the external housing 202 when assembled to allow the user to easily grasp or otherwise manipulate the handle 436. As shown, in some embodiments, the distal portion 434 is generally U-shaped such that a portion of the distal portion 434 is configured to be positioned on the left side 403 of the frame 310 and a portion of the distal portion 434 is configured to be positioned on the right side 405 of the frame 310. Such configurations can desirably provide rigidity and/or structural support to the handle 436. Other shapes and configurations are contemplated.

In some embodiments, the singulation actuator 214 includes a singulation spring protrusion 438. The singulation spring protrusion 438 can be positioned at the region where the tapered region of the central transition region 432 transitions to the distal portion 434. In some embodiments, the singulation spring protrusion 438 is positioned at the distal portion 434 or other portion of the singulation actuator 214. The singulation spring protrusion 438 can extend downwardly and/or outwardly from a main body of the singulation actuator 214. The singulation spring protrusion 438 can be configured to be coupled with the singulation biasing member 332.

The singulation biasing member 332 can include a singulation spring 332 or other biasing material. The singulation spring 332 can include a proximal spring portion 440 and a distal spring portion 442. In some embodiments, the proximal spring portion 440 of the spring 332 is in a generally compressed state in an initial position or configuration in use. For example, the plurality of adjacent coils of the spring 332 can contact one another in the initial position or configuration of the proximal spring portion 440. In some embodiments, the distal spring portion 442 of the spring 332 is in a generally tensioned state in an initial position or configuration in use. For example, the plurality of adjacent coils of the spring 332 can be spaced apart in the initial position or configuration of the distal spring portion 442.

As shown in FIGS. 8A and 8B, the singulation spring protrusion 438 can be coupled with the singulation spring 332 at a transition region 444 of the spring 332. The transition region 444 can be positioned at the portion of the spring 332 that transitions between the distal spring portion 442 and the proximal spring portion 440. In some embodiments, a ratio of a length of the proximal portion 440 to a length of the distal portion 442 is approximately 1:1, 1:2, 1:3, 1:4 or other ratio. In some embodiments, the spring 332 or portions of the spring 332 is angled. For example, in some embodiments, a terminus proximal end of the spring 332 is positioned at a higher elevation than a terminus distal end of the spring 332 when assembled. The spring 332 includes one or more attachment members, such as rings, that can be configured to attach to other components of the multiple-implant delivery apparatus 200. The spring 332 can include a distal ring 448 positioned at the terminus distal end of the spring 332 that can be configured to be coupled with a protrusion 447 positioned at the distal end portion of the left side 403 of the frame 310. The spring 332 can include a proximal ring 446 positioned at the terminus proximal end of the spring 332 that can be configured to be coupled with the singulation arm 334 as described below. The rings 446, 448 may be replaced with other connection or fastening members.

FIGS. 9A-9C illustrate an embodiment of the singulation arm 334. The singulation arm 334 can include a main body portion 450, a distal singulation spring connector 452, a singulation arm connection member 454, a proximal singulation slot member 456, and a distal singulation arm collet holder member 458. In some embodiments, the main body portion 450 is generally triangular shaped. In some embodiments, a distal end portion 462 of the singulation arm 334 has a height or width that is larger than a height or width of a proximal end portion 460 of the singulation arm 334. In some embodiments, the proximal singulation slot member 456 extends outwardly from a left side of the proximal end portion 460. The proximal singulation slot member 456 can be generally rectangular, among other shapes. The proximal singulation slot member 456 can have a flat top surface and/or a flat bottom surface. In some embodiments, the proximal singulation slot member 456 is shaped to easily slide between adjacent platforms 414 of the singulation frame slot 412 of the frame 310 in use.

As mentioned above, the distal singulation spring connector 452 can extend outwardly from the left side of the main body portion 450 of the singulation arm 334 and can be configured to be coupled with the proximal ring 446 of the spring 332. In some embodiments, the distal singulation spring connector 452 is spaced apart from the main body portion 450 by the singulation arm connection member 454. The singulation arm connection member 454 can be configured to reside within the singulation arm slot 416 of the frame 310 to allow the distal singulation spring connector 452 to be positioned at least partially on the left side 403 of the frame 310 and the proximal singulation slot member 456 and the distal singulation arm collet holder member 458 to be positioned on the right side 405 of the frame 310 when assembled.

In some embodiments, the distal singulation arm collet holder member 458 extends outwardly towards the right from an extension of the distal end portion 462 of the singulation arm 334. The distal singulation arm collet holder member 458 is configured to contact or otherwise be positioned within a rear collet holder recess 484 of the collet holder 360 when assembled (see FIG. 6A). When a respective implant of the multiple-implant delivery apparatus 200 is in a "ready to fire" position, the distal singulation arm collet holder member 458 is advantageously always located in the same place regardless of which singulation slot or platform the singulation arm 334 is in or in contact with so that the clinician sees the same implant position prior to each successive implant delivery, thereby providing ease-of-use benefits and peace of mind for the clinician.

Figure 10C:
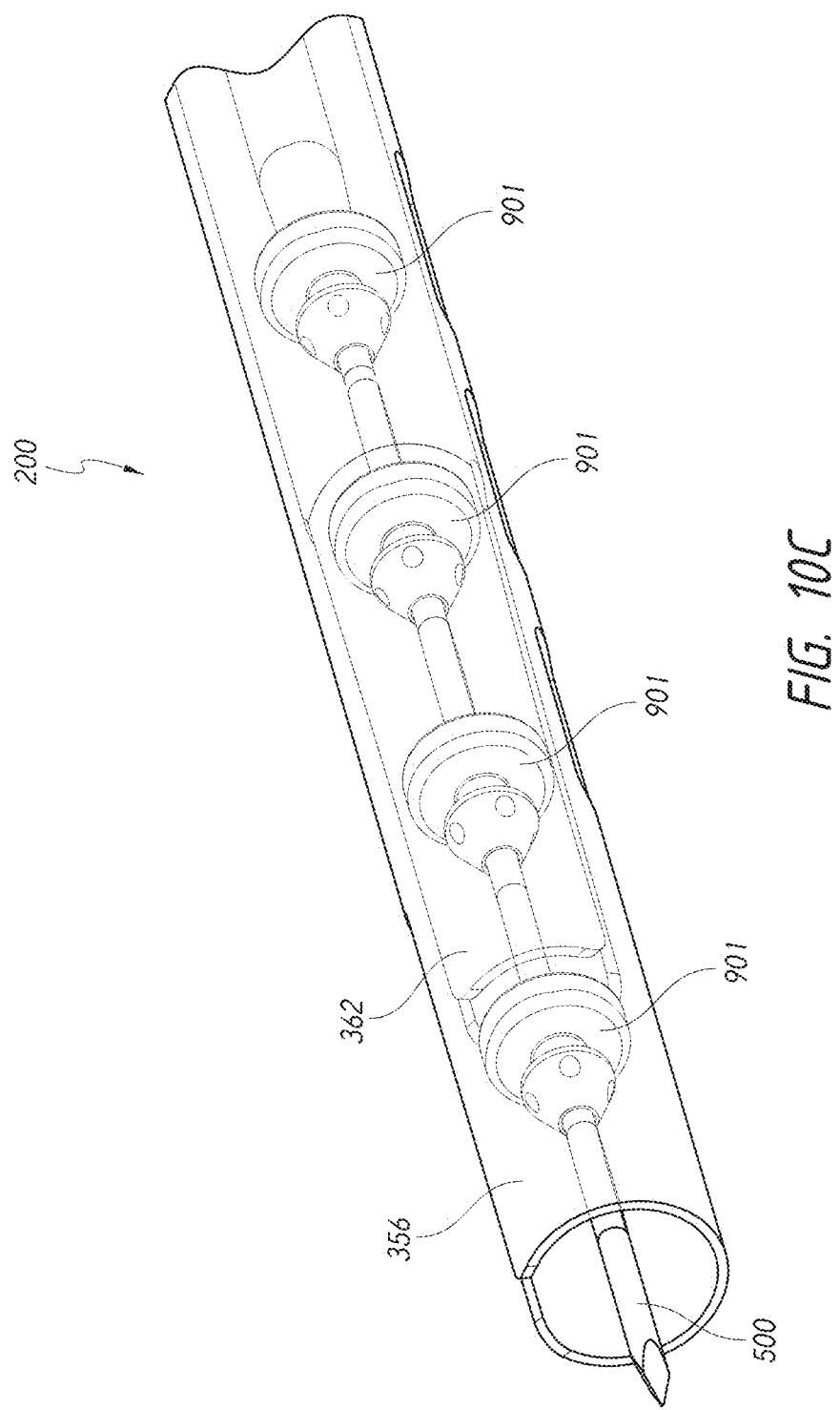
FIG. 10C is a close-up view of a portion of the tube set assembly of FIG. 10A.

In some embodiments, the singulation assembly 330 is configured to interface with the tube set assembly 350 when assembled. As shown in FIGS. 10A-10C, the tube set assembly 350 can include the insertion tube subassembly 352 having an insertion tube carrier 354 and an insertion tube 356; a collet holder assembly 358 having a collet holder 360 and a singulation tube 362; and a trocar assembly 364.

Figure 11A:
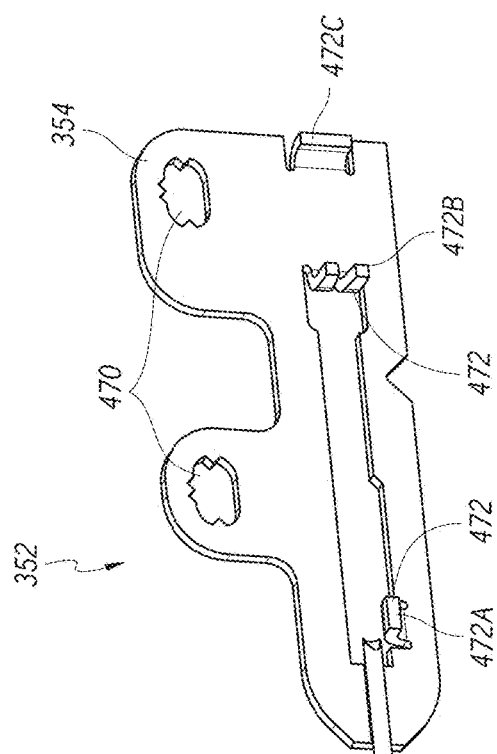
FIG. 11A is a right side perspective view of an embodiment of an insertion tube subassembly of the tube set assembly of FIG. 10A.
Figure 11B:
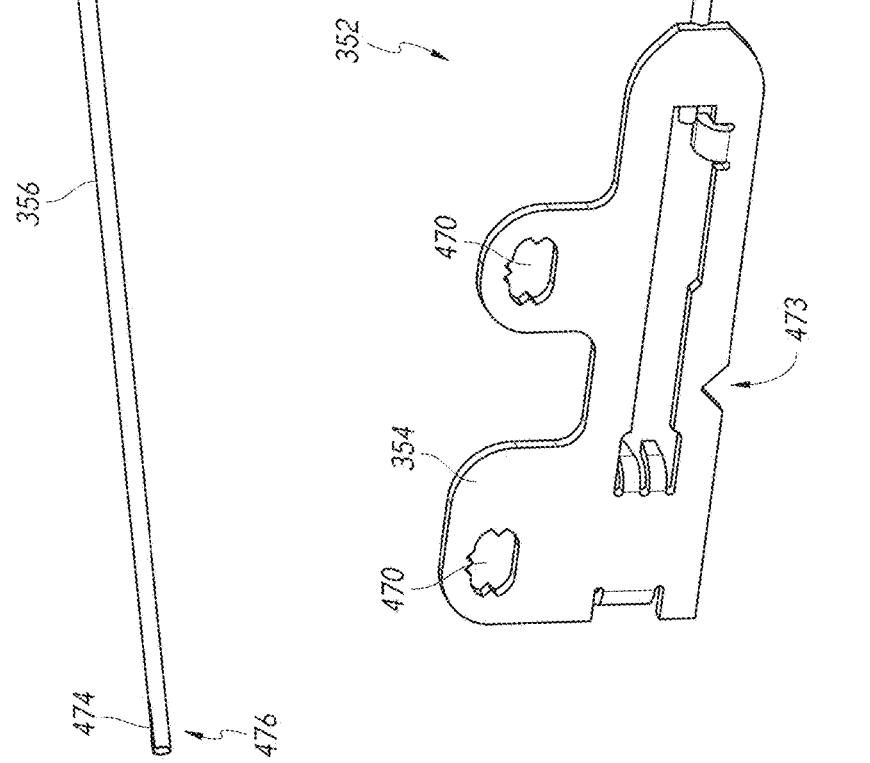
FIG. 11B is a left side perspective view of the insertion tube subassembly of FIG. 11A.

FIGS. 11A and 11B illustrate the insertion tube subassembly 352. The insertion tube subassembly 352 can include the insertion tube carrier 354 and the insertion tube 356. The insertion tube carrier 354 can include at least one opening 470. In some embodiments, the insertion tube carrier 354 includes two, three, four, five, or six or more openings 470. As described above, in some embodiments, the openings 470 are configured to receive the tube set assembly attachment members 420 to secure the tube set assembly 350 within the external housing 202 when at least a portion of the tube set assembly 350 is assembled with the frame 310. In some embodiments, the tube set assembly attachment members 420 is sized and/or configured to snap to, be heat staked to, be screwed to, or otherwise reside within or be received by or engaged with the openings 470. The insertion tube subassembly 352 can be fixedly connected to the frame 310 in use.

In some embodiments, the insertion tube carrier 354 includes a carrier notch 473. The carrier notch 473 can be positioned at approximately a midpoint along a bottom edge of, or anywhere along the insertion tube carrier 354. The carrier notch 473 can be configured to align with a corresponding collet holder notch 488 of the collet holder 358 when assembled. The alignment of the carrier notch 473 with the collet holder notch 488 can indicate an initial position of the collet holder subassembly relative to the insertion tube subassembly 352.

In some embodiments, the insertion tube carrier 354 includes a plurality of tabs 472 that extend outwardly from the insertion tube carrier 354, for example, towards a right side of the carrier 354. As shown, the insertion tube carrier 354 can include a first tab 472A, a second tab 472B, and a third tab 472C. The first tab 472A can be positioned at a distal end portion of the insertion tube carrier 354. The first tab 472A can limit distal movement of the collet holder assembly 358 relative to the insertion tube carrier 354. For example, as explained in more detail below, a distance between the front end of the collet holder 358 and the first tab 472A when the tube set assembly 350 is in an initial position defines the distance the collet holder 358 can translate relative to the insertion tube carrier 354 during implant delivery after the implant delivery actuator 216 is actuated. For example, when the implant delivery actuator 216 is actuated, the collet holder 360 can translate distally and contact the first tab 472A such that the distal end 361 of the collet holder 360 abuts the first tab 472A.

In some embodiments the second tab 472B forms a pronged arrangement including at least two spaced apart prongs defining a slot between the prongs. The pronged arrangement can be configured to pass through a collet holder opening 480 when the collet holder 360 is assembled with the insertion tube carrier 354. The pronged arrangement can allow at least a portion of the trocar assembly 364, such as the backup tube 502 to pass through the spaced apart prongs. The pronged arrangement can desirably help to limit vertical displacement of the trocar assembly 364 when the tube set assembly 350 is assembled. In some embodiments, the second tab 472B is configured to act as a stop to limit proximal movement of the collet holder 358 relative to the insertion tube carrier 354 in use. For example, as discussed below, the collet holder 358 can move proximally during singulation. A distance between a front end of the collet holder opening 480 and the second tab 472B when assembled can define a distance the collet holder 358 moves proximally during singulation. The second tab 472B can act as a stop to provide the maximum proximal distance the collet holder 358 can translate relative to the insertion tube carrier 354. The distances can be designed to be very precise.

In some embodiments, the third tab 472C is positioned at a proximal terminus end of the insertion tube carrier 354. The third tab 472 can extend at least partially through the collet holder opening 480 when the collet holder 360 is assembled with the insertion tube carrier 354. In some embodiments, the third tab 472 is configured to define a backstop to limit proximal movement of the trocar assembly 364 in use.

In some embodiments, the insertion tube 356 is fixedly coupled with the insertion tube carrier 354 by various attachment means, such as by soldering, heat staking, welding, laser welding, laser machining, gluing, or other processes. In some embodiments, a proximal end portion of the insertion tube 356 is coupled with the insertion tube carrier 354, for example, at a distal portion of the right side of the carrier.

FIGS. 12A and 12B illustrate an embodiment of the insertion tube 356 in more detail. In some embodiments, the insertion tube 356 includes a slot 474 formed at the distal end 476 of the insertion tube 356. The slot 474 can be substantially V-shaped, U-shaped, or other shapes. The slot 474 can be configured to allow the user to visualize the implant before and/or after the implant is delivered by the delivery apparatus 200 into the patient's eye. Delivery of an implant can be actuated multiple times until it is in a desired final implantation position, as advantageously determined by visualization through the slot 474.

The insertion tube 356 can define a lumen configured to surround at least a portion of the trocar assembly 364 and/or the singulation tube 362 (see FIG. 10C). The insertion tube 356 can include a plurality of openings 478. The openings 478 can include one, two, three, four, five, or more openings. The number of openings 478 can correspond to the number of pre-loaded implants 901 in the multiple-implant delivery apparatus 200. The openings 478 can be spaced apart axially along an outer circumferential surface of the insertion tube 356. In some configurations, the openings 478 can desirably allow a user to visualize the implants 901 within the tube during manufacture to verify that the desired number of implants 901 are pre-loaded and pre-loaded at the proper location. As shown, the openings 478 may be positioned circumferentially opposite (180 degrees or approximately 180 degrees circumferentially away from) the slot 474.

FIG. 13 shows an embodiment of the collet holder subassembly 358. The collet holder subassembly can include a collet holder 360 and a singulation tube 362. The collet holder 360 can include an opening 480, as described above, that can receive at least a portion of the insertion tube carrier 354, such as at least one of the tabs (e.g., the second tab 472B and/or the third tab 472C). The collet holder opening 480 can be positioned in a distal portion of the collet holder 360 and can pass through a width of the collet holder 360. The collet holder 360 can include a rear collet holder recess 484. The rear collet holder recess 484 can be positioned at a proximal end portion of the collet holder 360. The rear collet holder recess 484 can extend from a top surface 486 of the collet holder 360 downwardly into the collet holder. The rear collet holder recess 484 can be configured to retain at least a portion of the singulation arm 334, such as the distal singulation arm collet holder member 458.

In some embodiments, the collet holder 360 includes a central collet holder recess 482. The central collet holder recess 482 can be positioned in a central region of the collet holder 360. The central collet holder recess 482 can extend from a top surface 486 of the collet holder 360 downwardly into the collet holder. The central collet holder recess 482 can be configured to retain at least a portion of the actuator arm 374, such as the actuator arm protrusion member 544, when the implant delivery actuator 214 is actuated.

The collet holder 360 can include the collet holder notch 488 as briefly referred to above. The collet holder notch 488 can be positioned at approximately a midpoint or distal to the midpoint of the collet holder opening 480 along a bottom edge of the collet holder 360. The collet holder notch 488 can be configured to align with the corresponding carrier notch 473 of the insertion tube carrier 354 when assembled. The alignment of the carrier notch 473 with the collet holder notch 488 can indicate an initial position of the collet holder subassembly relative to the insertion tube subassembly 352.

In some embodiments, the singulation tube 362 is fixedly coupled with the collet holder 360 by various attachment means, such as by soldering, heat staking, welding, laser welding, laser machining, gluing, or other processes. In some embodiments, a proximal end portion of the singulation tube 362 is coupled with the collet holder 360, for example, at a distal portion of the left side of the collet holder. FIG. 14 illustrates an embodiment of the singulation tube 362 in more detail. In some embodiments, the singulation tube 362 includes a slot 490 formed at the distal end 492 of the singulation tube 362. The slot 490 can be substantially V-shaped, U-shaped, or other shapes. The slot 490 can be formed by forming tines in the distal end 492 of the singulation tube 362 (e.g., by laser cutting or machining) to form two or more symmetrical or asymmetrical flanges about a central longitudinal axis of the singulation tube 362. The distal end 492 with formed tines advantageously allows the singulation tube 362 to be retracted over a maximum cross-sectional dimension of a next implant positioned along the trocar 500 when the singulation tube is being retracted proximally during singulation after delivery of a previous implant and then transition back to a configuration that is configured so that a distal terminus of the distal end 492 contacts a distal end of the next implant and propels the next implant out of the delivery apparatus 200 when the implant delivery actuator 214 is actuated to deliver the next implant. The distal end 492 may comprise shape memory or flexible material. In some embodiments, the shape of the slot 490 is configured such that the distal terminus of the distal end 492 is configured to contact a distal end of an implant every time the implant delivery actuator 214 is actuated (e.g., button is pressed). In some embodiments, the distal end 492 and the slot 490 are advantageously configured to allow for an infinite number of actuations.

As shown in FIG. 10C, the singulation tube 362 can define a lumen to surround at least a portion of the trocar assembly 364. In some embodiments, the singulation tube 362 has an outer diameter sized to fit within the insertion tube 356.

FIG. 15A illustrates an embodiment of the trocar assembly 364. The trocar assembly 364 can include a trocar 500 and/or a backup tube 502. FIGS. 15B-15D illustrate embodiments of a splayed trocar configured to facilitate manual singulation of multiple implants on demand (e.g., not automatic).

FIG. 15B illustrates a close-up view of the trocar 500. In accordance with several embodiments, the trocar 500 defines an elongate member (e.g., a wire or rod) on which the multiple implants 901 can be loaded and along which the implants 901 can be advanced. In some embodiments, one or more singulation features are present (e.g., formed or coupled) at various positions along the trocar 500 to cingulate, or separate, the multiple implants 901 so that they are not stacked up directly against one another (e.g., no double-stacking). The singulation features function to keep the implants 901 apart so that they are not touching one another. Without the singulation features (and thus with the implants 901 stacked up directly against one another), the tolerances within the instrument and the tolerances of the implants themselves have to be extremely precise in order to facilitate singulation of each successive individual implant for delivery. In some embodiments, the singulation features are formed by slitting the trocar (e.g., by forming a small incision along a central longitudinal axis of the trocar and entirely through the trocar as shown, for example, in FIG. 15B and then splaying the portion of the trocar 500 with the slit 504 to form a splay 506 (e.g., eyelet or opening) within the trocar 500 (as shown, for example, in FIG. 15B). Splaying the trocar 500 can be performed by inserting a wire or other device through the slit 504 and forcing the slit 504 open. The splays 506 may be formed while maintaining a generally straight geometry. The eyelet or opening can be heat set to maintain the eyelet or opening in a resting, relaxed or unstressed configuration. When sufficient force is applied to the rear of the implant 901 (e.g., by a collet or other advancement member), the implant, the heat set shape of the splay or eyelet is overcome and the implant is advanced over the splay or eyelet. In some embodiments, the splayed trocar 500 is formed by laser cutting, machining or etching a solid elongate member (e.g., cylindrical trocar) to form the splays 506 (e.g., eyelets or openings) at various positions along the length of the trocar 500. The trocar 500 can be made of stainless steel, MP35 superalloy, tungsten, nickel titanium alloy (e.g., nitinol), plastic, or other elastic, flexible, and/or shape memory materials.

In some embodiments, multiple (e.g. one, two, three, four, or more) singulation features (e.g., eyelets, splays, protrusions, balloons) are included along the length of the trocar 500 (depending on the number of implants intended to be included and delivered). An implant 901A can be positioned (e.g., pre-loaded) before (distal of) the first splay 506A so that it is in a "ready-to-fire" position upon initial actuation by a user. A second implant 901B can be loaded or positioned between the first and second splays 506A, 506B, a third implant 901C can be loaded or positioned between the second and third splays 506B, 506C, and so on (as illustrated, for example, in FIG. 15D). In some embodiments, the number of splays may correlate to the number of implants. In some embodiments, an implant is positioned between each splay 506. Thus, each of the implants can be separated and can be easily singulated by manually actuating the singulation actuator 214 without having to be as precise with tolerances and singulation distances. With the trocar 500 having the singulation features, instead of the singulation member having to be positioned between the proximal end of a first stent and the distal end of the second stent stacked up right against the first stent, the singulation member advantageously only has to be positioned within the length of the splay (e.g., eyelet or opening). As one example, the singulation tolerance may be less than 0.004" without the singulation features and may be less than 0.016" with the singulation features (a 4:1 difference in singulation tolerance). The splayed trocar 500 can be used with any number of implant shapes as long as they have a central lumen sized to be advanced along the outer diameter of the trocar. In some embodiments, the implants are ophthalmic implants designed to shunt aqueous humor between an anterior chamber of an eye and Schlemm's canal to facilitate reduction of intraocular pressure to treat glaucoma.

In some embodiments, the trocar 500 is angled or curved in certain embodiments. The trocar 500 can be rigid, semi-rigid, or flexible. In certain embodiments, some portions of the trocar 500 are flexible and other portions are rigid. In embodiments where the trocar 500 can be stiff, the implant can be, but need not be relatively flexible. In certain embodiments, the trocar 500 and the backup tube 502 are advantageously constructed of stainless steel. In other embodiments, the trocar 500 and the backup tube 502 can be constructed of other suitable materials, such as other metals, plastics, or polymers.

The backup tube 502 can surround at least a portion of the trocar 500 to provide additional rigidity to the trocar 500. The backup tube 502 includes a hollow tube having an inner diameter sized to receive the trocar 500. In certain embodiments, backup tube 502 has an inner diameter of about 0.0035 inches; however, the backup tube 502 can have any inner diameter sized so as to receive the trocar 500. As shown, the backup tube 502 can include a chamfered distal end 503. In certain embodiments, the backup tube 503 is advantageously laser welded to the trocar 500 upon assembly. In some embodiments, the backup tube 502 can be bonded to the trocar 500 using other methods of fixation (for example, curing, welding, press-fitting, adhesive). The trocar 500 and backup tube 502 may be cut by laser or centerless ground.

Figures 1, 15E:
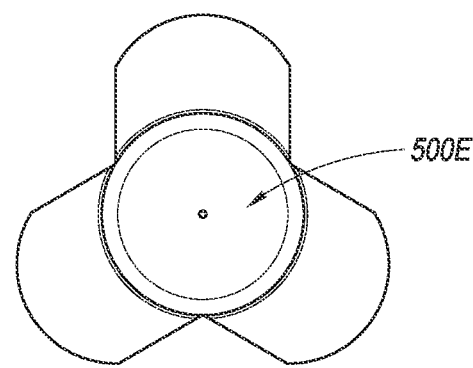
FIGS. 15E-1 to 15E-3 illustrate a front view, perspective view, and side view of an alternative embodiment of a trocar comprising polymeric material.

As mentioned above, the singulation actuator 214 facilitates the singulation (e.g., isolation, separation, and/or selection) of one of the multiple implants for delivery one at a time. The singulation actuator 214 interfaces with internal components (described above) to effect singulation. Several alternative embodiments can be used to effect singulation. For example, FIGS. 15E-15Z illustrate various embodiments that could be implemented instead of the splayed trocar singulation embodiment illustrated in FIGS. 15A-15D. In some embodiments, the singulation features are formed by including nubs or protrusions at various positions along the trocar 500 that are flexible or resilient enough to allow the implants to be advanced over them when sufficient force is applied to the implants.

Figures 2, 15E:
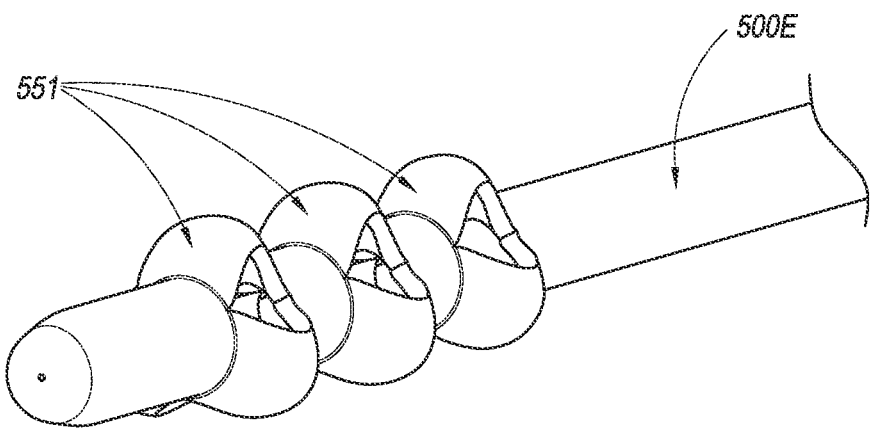
Figures 3, 15E:
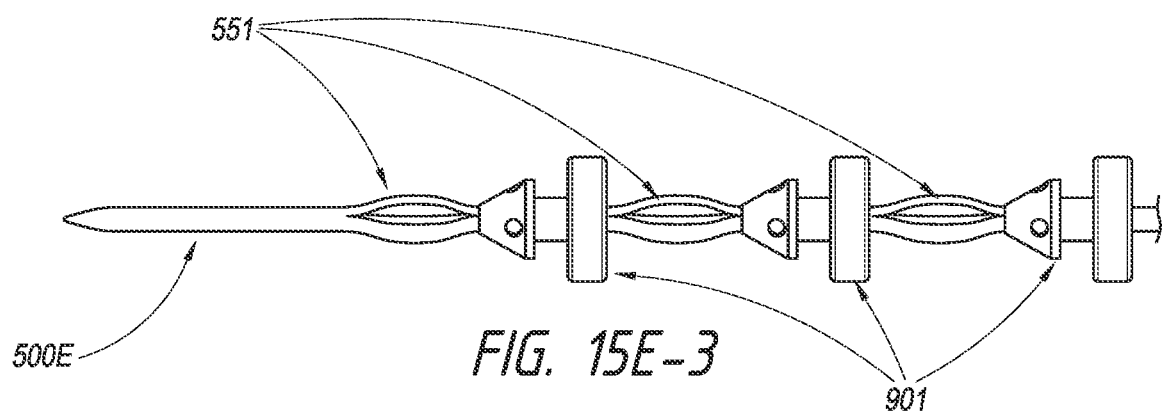

FIGS. 15E-1 to 15E-3 illustrate an embodiment of a singulation design that is similar to the splayed trocar design illustrated and described above in connection with FIGS. 15A-15D but the singulation features are polymer "balloons" instead of splays along the trocar 500E. In this "polymer balloon" embodiment, the trocar 500E is made out of a tubular polymer material and the "balloon" areas (i.e., separation areas) 551 are enlarged with a triple bump (e.g., bumps spaced 120 degrees apart circumferentially as shown in FIGS. 15E-1 to 15E-3) or a double bump (e.g., bumps spaced 180 degrees apart on opposite sides of the trocar 500E, not shown). The "polymer balloon" embodiment may include the structural or functional features described in connection with the splayed trocar embodiment of FIGS. 15A-15D.

Figure 15F:
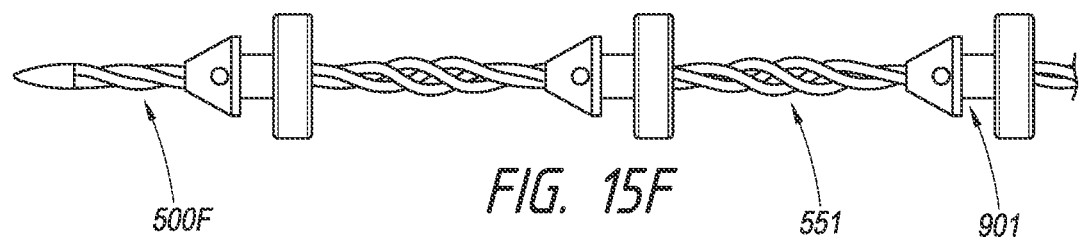
FIG. 15F illustrates a side view of an alternative embodiment of a trocar formed of a plurality of braided wires.

FIG. 15F illustrates an embodiment of a twisted trocar singulation design. In this embodiment, the trocar 500F comprises a plurality of wires twisted together. The wires are twisted tightly in most locations, but in the specified implant separation areas 551, the wires are configured (e.g., twisted or arranged in such a manner) to allow the outer diameter of the trocar 500F to enlarge at the separation areas. During singulation, as a respective implant 901 moves forward (e.g., distally), the twisted wires compress, thereby allowing the implant 901 to pass over the separation area.

Figures 1, 15G:
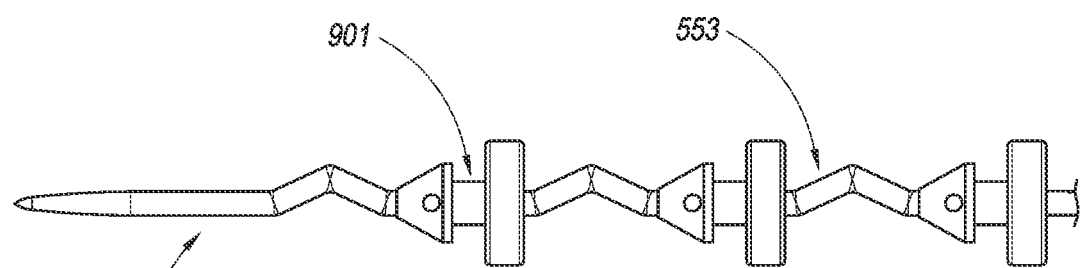
Figures 2, 15G:
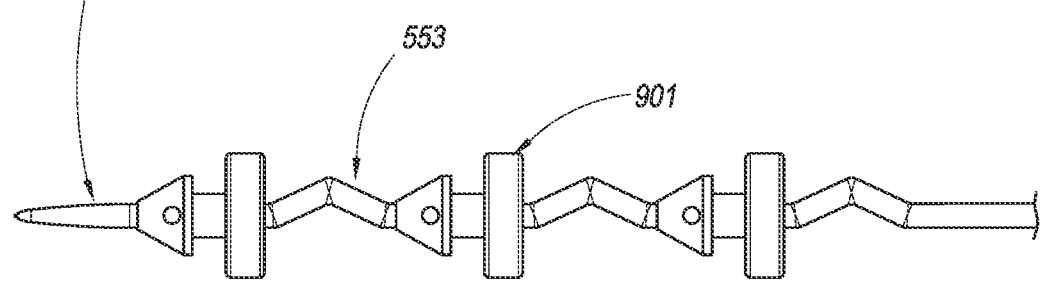

FIGS. 15G-1 and 15G-2 illustrate an embodiment of a "bent trocar" singulation design. This singulation design includes a trocar 500G having multiple singulation features in the form of bend regions 553 along the length of the trocar 500G that are spaced so as to effectively separate the plurality of implants 901. The "bent trocar" design provides a mechanical separation of the implants 901 that is strong enough to prevent movement while the multiple-implant delivery apparatus 200 is not in use, but weak enough to deflect flat (straighten out) during singulation (e.g., when sufficient force is exerted on the implant in the distal direction to straighten out the adjacent bend region). FIG. 15G-2 shows the implants 901 after being singulated to the next distal position by the singulation actuator 214. Each implant 901 in FIG. 15G-2 has been advanced distally over the respective bend region that was distally adjacent to each respective implant 901 in FIG. 15G-1.

Figures 1, 15H:
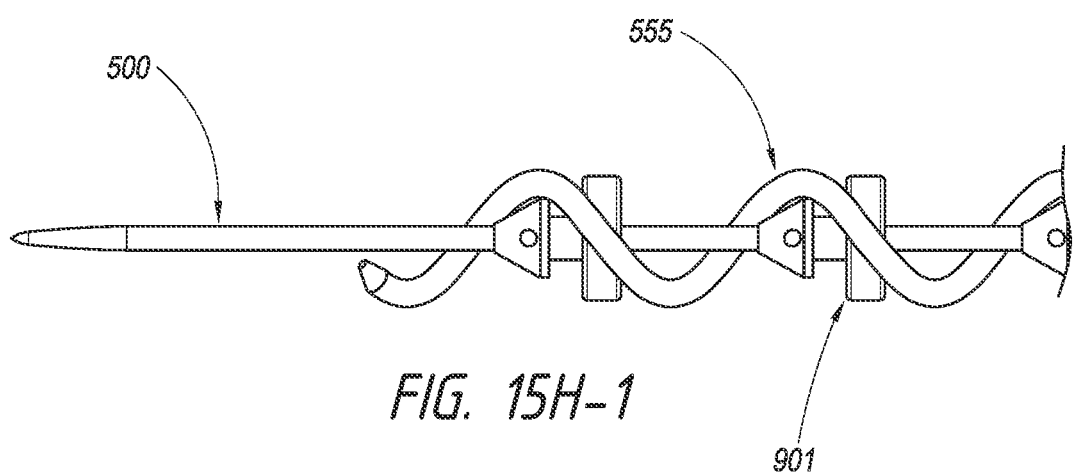
Figures 2, 15H:
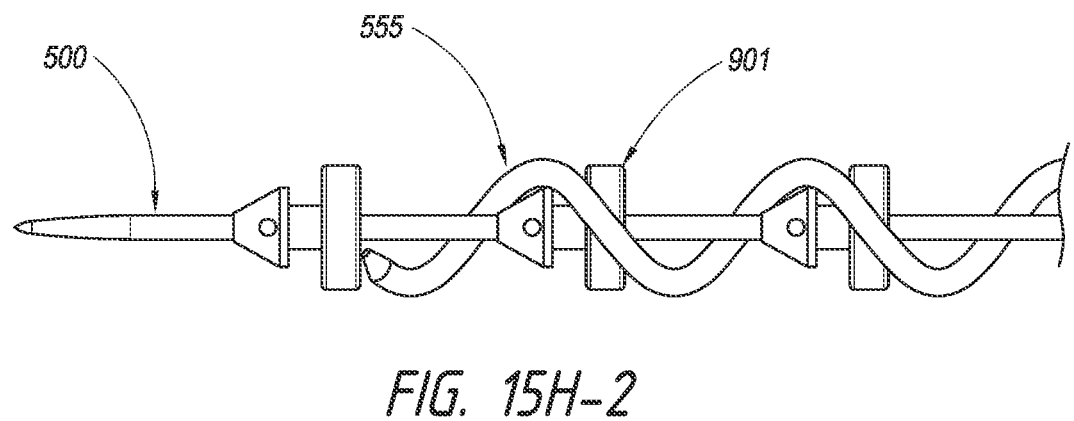

FIGS. 15H-1 and 15H-2 illustrate an embodiment of a "corkscrew" singulation design. The "corkscrew" singulation design includes a secondary wire 555 that is spiral-shaped and is configured to wrap around the trocar 500. The spiral wire 555 effectively separates the implants 901 and can advance the implants 901 forward when the wire 555 is turned, or rotated. FIG. 15H-2 shows the implants after having been moved distally along the trocar 500 by the wire 555.

Figures 1, 15I:
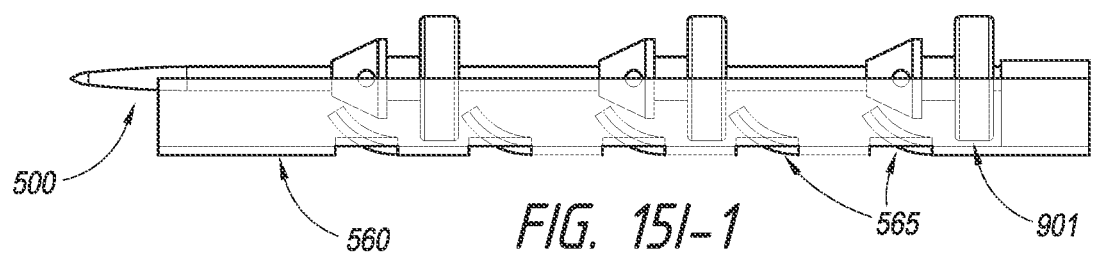
Figures 2, 15I:
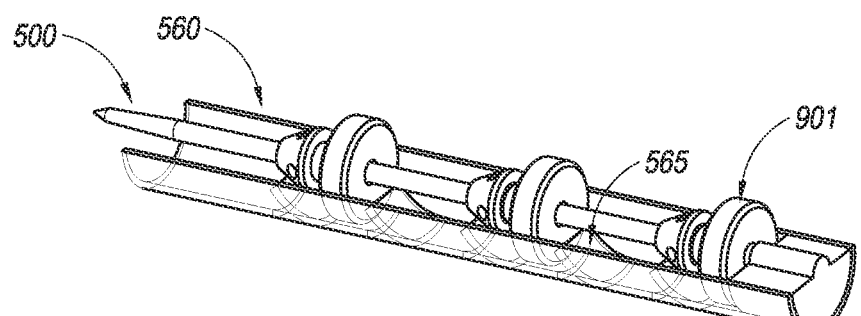
Figures 3, 15I:
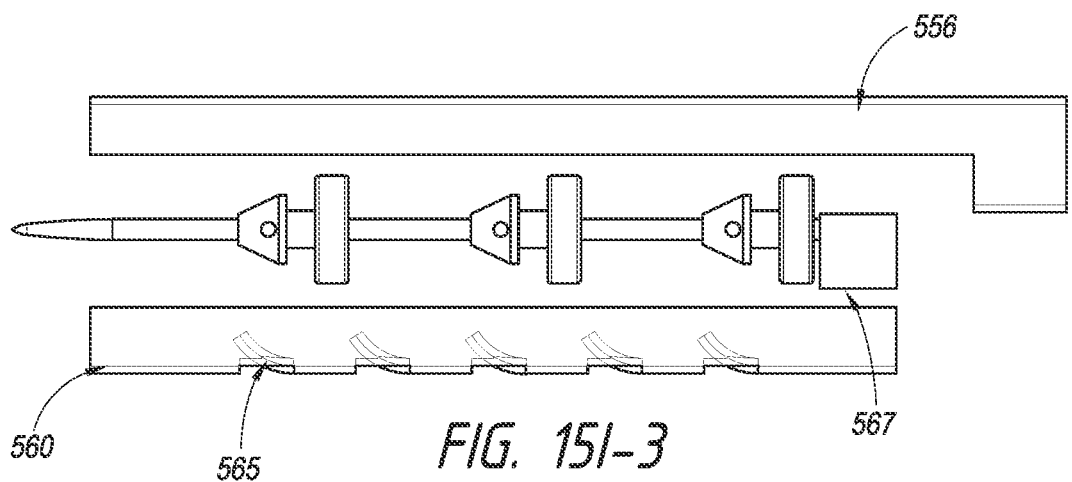
Figures 4, 15I:
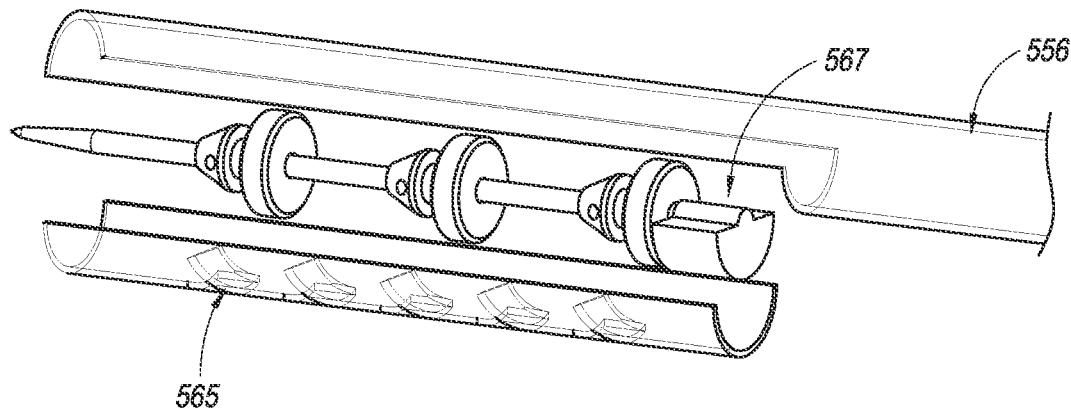
Figure 15J:
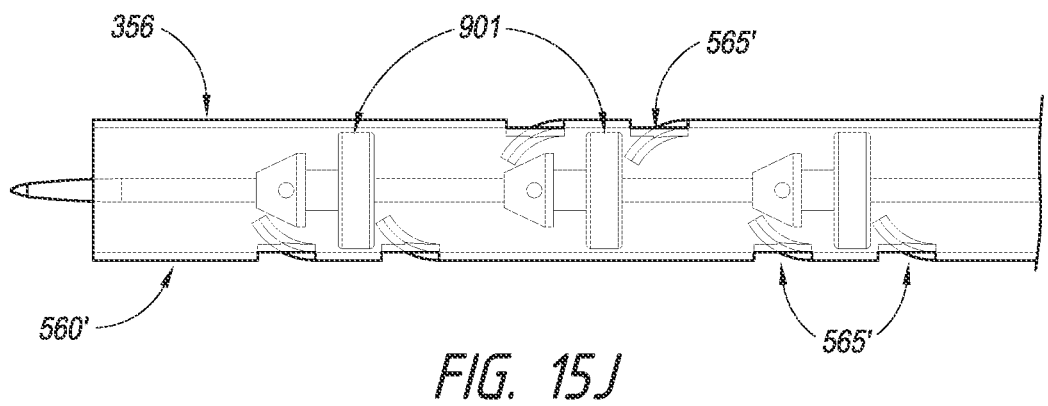
FIG. 15J illustrates a side view of another embodiment of an ice cube tray singulation assembly having cut-out tabs on opposite sides of the insertion tube.

FIGS. 15I-1 to 15I-4 illustrate an embodiment of an "ice cube tray" singulation design. The "ice cube tray" embodiment includes a semi-circular "tube" portion 560 with cut-out tabs 565 bent inward. The tabs 565 are positioned in front of and behind each implant 901, thereby securing each respective implant's initial position along the trocar 500. During singulation, each implant 901 can cause the adjacent tab(s) 565 to bend downward due to the force applied on the implant by the singulation actuator 214, thereby allowing each implant 901 to move forward, or distally. The semi-circular tube portion 560 can be affixed to a preassembled multiple-implant delivery apparatus prior to shipping or after shipping but prior to surgery. The semi-circular "tube" portion 560 may be coupled to or form a portion of the insertion tube 356. As shown in FIGS. 15I-3 and 15I-4, the semi-circular tube portion 560 can be attached or coupled to a corresponding tubular member 556 to form a complete insertion tube 556 to surround the trocar 500. The insertion tube 356 may replace or incorporate any of the structural or functional features of the insertion tube 356 described herein. In one embodiment, the force sufficient to cause the implants 901 to bend the adjacent tab(s) 565 inward can be provided by a pusher member 567. FIG. 15J illustrates an embodiment of a singulation design that is similar to the "ice cube tray" design, but the tube 560' is fully enclosed and the opposite side of the tube 560' also includes alternating cut-out tabs 565'. The advancement of the implants 901 for this alternating cut-out tabs embodiment may operate similarly to that described for the "ice-cube tray" embodiment.

Figures 1, 15K:
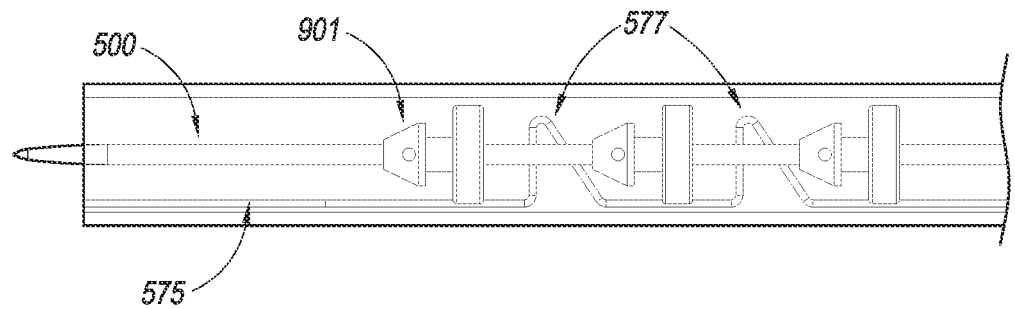
Figures 2, 15K:
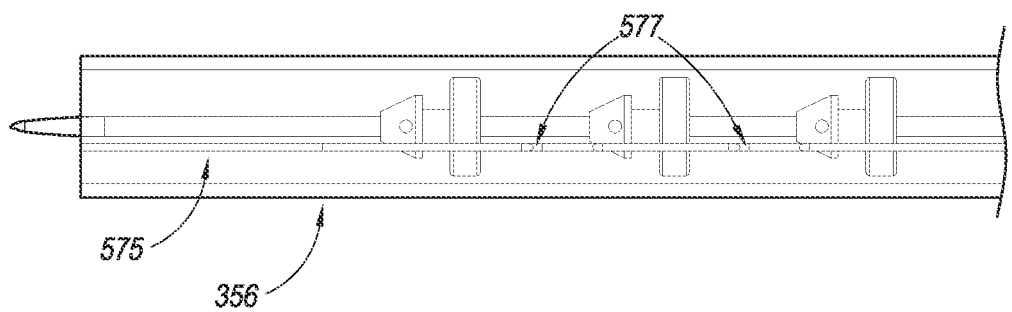
Figures 3, 15K:
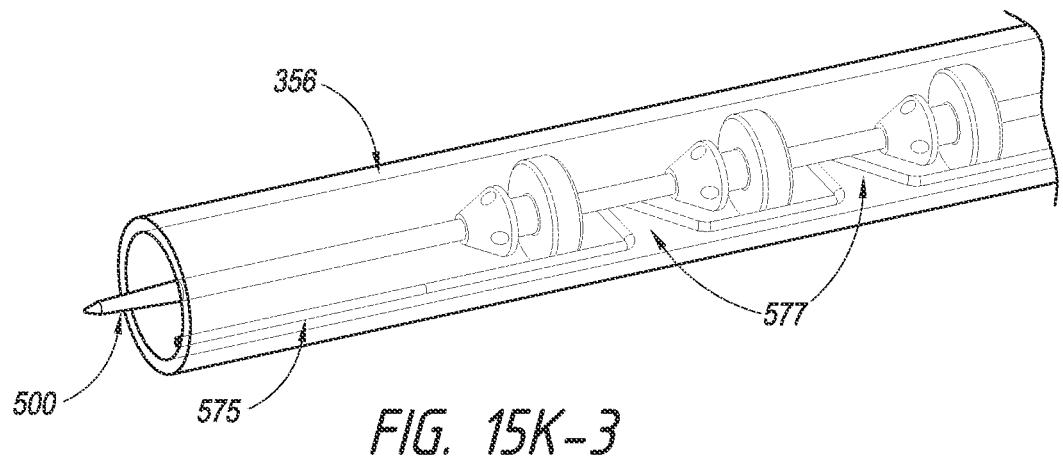
Figures 1, 15L:
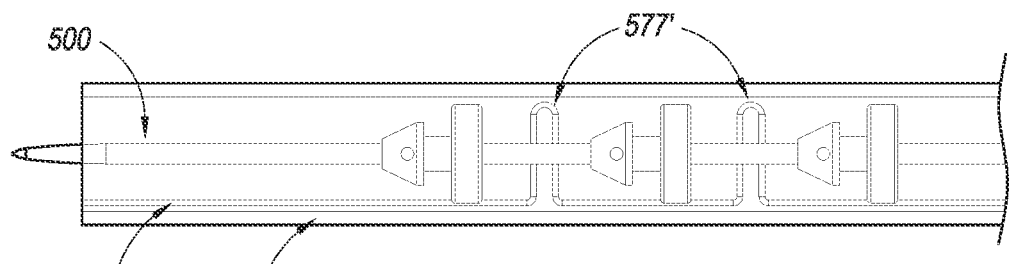
Figures 2, 15L:
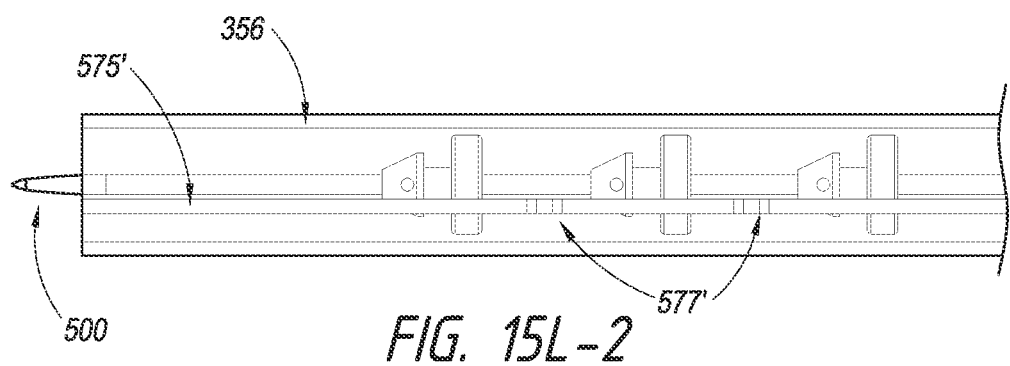
Figures 3, 15L:
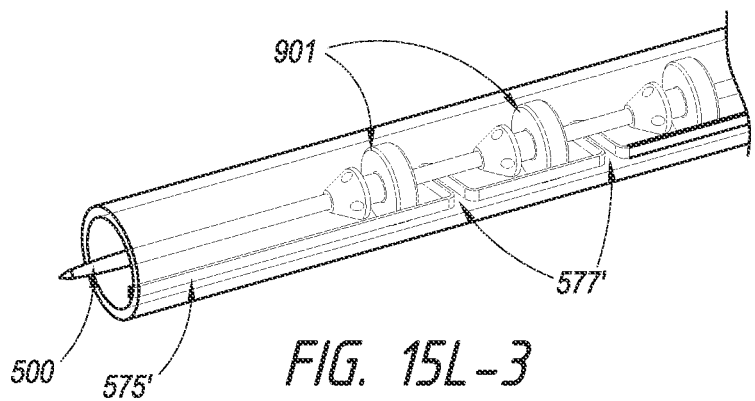

FIGS. 15K-1 to 15K-3 illustrate an embodiment of a spring wire singulation implementation. A spring wire 575 is positioned along the trocar 500 that includes the plurality of implants 901. The spring wire 575 is bent at multiple spaced-apart locations in a configuration designed to keep the implants 901 separate in their natural state, but the spring wire 575 can be rotated so that the bent regions or portions 577 are rotated out of the way so as not to obstruct advancement of the implant(s) 901 during singulation, as shown in FIG. 15K-3. The bent regions can form a triangular shape or a "shark-fin" shape or other angled shape. The embodiment illustrated in FIGS. 15L-1 to 15L-3 is similar to the spring wire singulation implementation but the wire 575' has a flat wire shape (e.g., an elongated U shape) that can bend flat over itself out of the way during singulation. FIG. 15L-3 illustrates the wire 575' rotated so that the bent regions or portions 577' are rotated out of the way so as not to obstruct advancement of the implant(s) 901 during singulation.

Figure 15M:
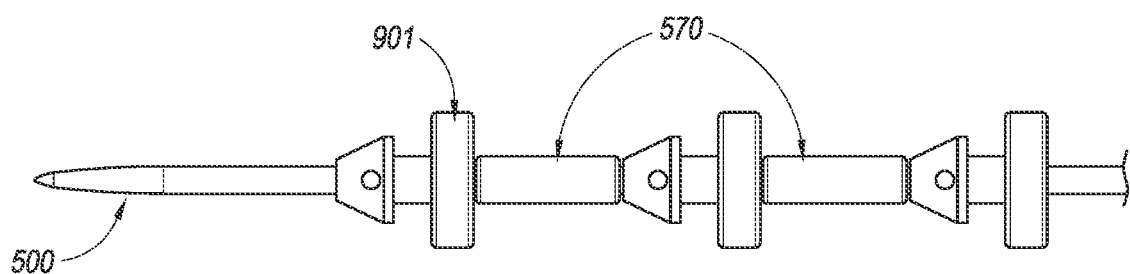
FIG. 15M illustrates an embodiment of a singulation assembly including multiple bioerodible spacers positioned between adjacent implants along the trocar.

FIG. 15M illustrates an embodiment of a singulation implementation that includes bioerodible spacers 570 positioned along the length of the trocar 500 at spaced-apart locations. The spacers 570 may be made, for example, from a rapidly erodible biocompatible polymer. Before entering the eye, the spacers 570 keep the implants 901 in their specified starting location. After entering the eye the spacers 570 rapidly erode, thereby allowing the implants to be singulated freely.

Figures 1, 15N:
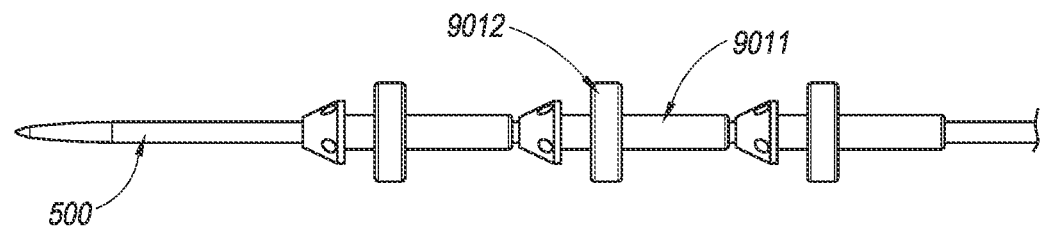
Figures 2, 15N:
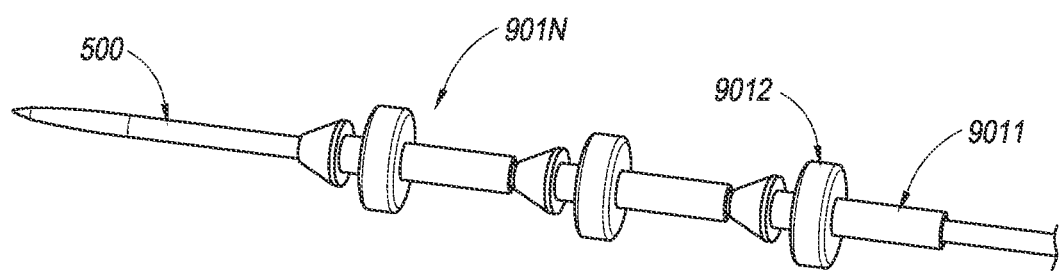
Figures 3, 15N:
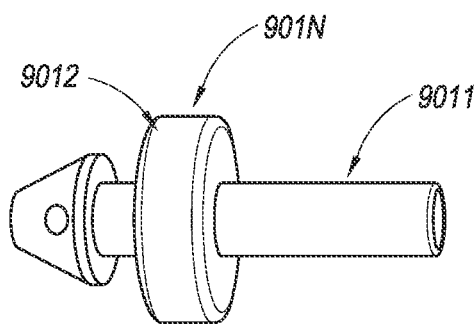

FIGS. 15N-1 to 15N-3 illustrate an embodiment of a singulation implementation in which the implants themselves are configured (e.g. sized and designed) to facilitate singulation. Each implant 901N includes an elongated snorkel 9011 extending proximally from a rear flange 9012 of the implant 901N. The elongated snorkel 9011 on this stent design provides a built-in separation of the implants 901N. The elongated snorkel 9011 provides a zone for a component of the singulation actuator 214 to land as the singulation actuator 214 is retracted, and then as it moves forward it pushes on the rear flange 9012 of the implant 901N. FIG. 15N-3 illustrates an embodiment of the implant 901N. The length of the elongated snorkel 9011 can vary depending on the desired spacing between the implants 901N.

Figure 16E:
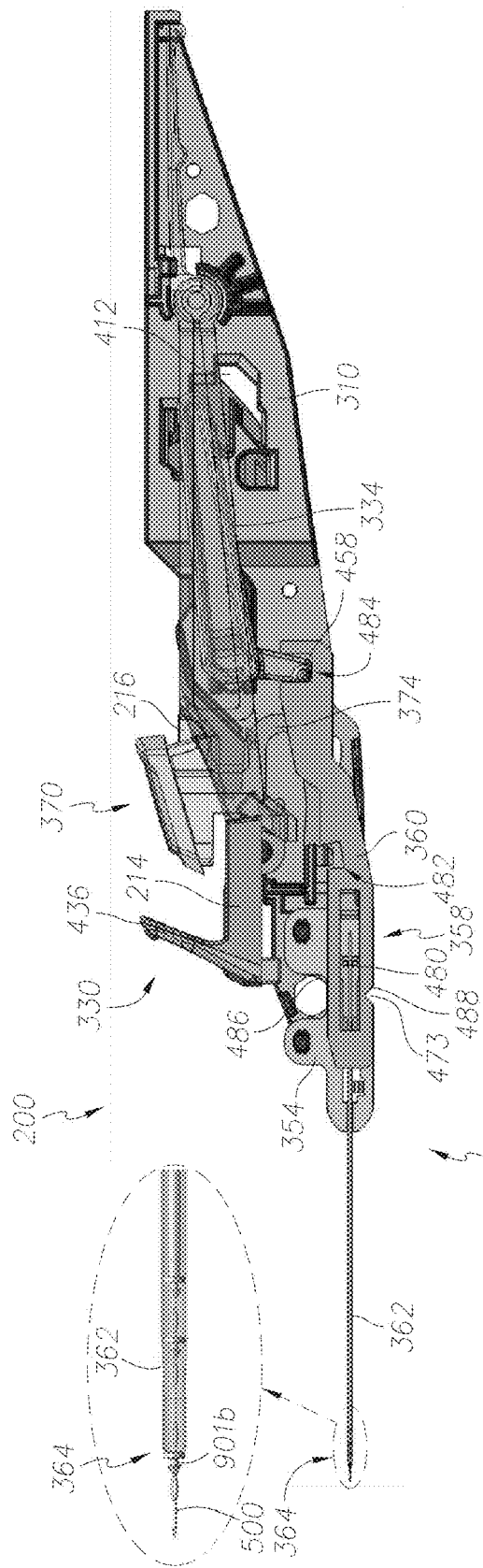
FIG. 16E is right side view of the internal components of the multiple-implant delivery apparatus of FIG. 16A in a third singulation position.
Figure 16F:
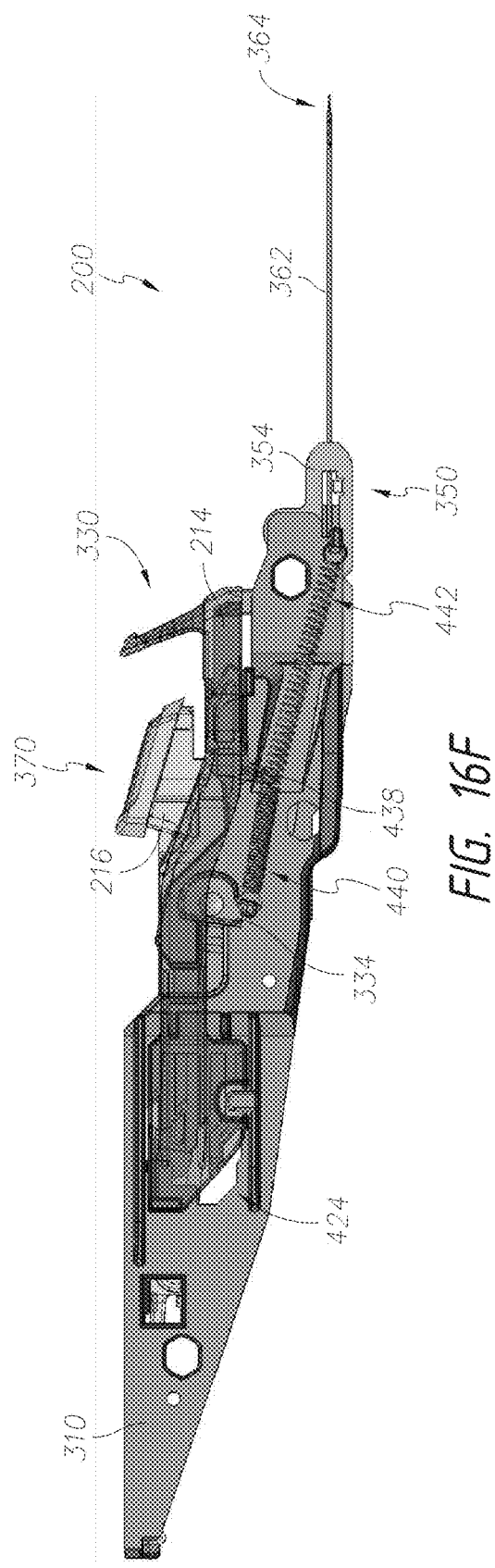
FIG. 16F is a left side view of the internal components of the multiple-implant delivery apparatus in the third singulation position.

FIGS. 16A-16F illustrate configurations of components of the multiple-implant delivery apparatus 200 at various stages before, during, and after singulation of an implant to help illustrate how singulation is carried out in the illustrated embodiment. FIGS. 16A and 16B illustrate an example first or initial position or configuration of several of the components of the multiple-implant delivery apparatus 200. For example, this first or initial position or configuration may be how the multiple-implant delivery apparatus 200 is shipped for initial use. In this initial configuration, the delivery apparatus 200 is ready to deliver the first implant. FIGS. 16C and 16D illustrate an example second position or configuration of the internal components during singulation of a second implant after delivery of the first implant. In this second position or configuration, the delivery apparatus 200 has isolated the second implant for delivery but has not yet advanced the second implant to the "ready-to-fire" position along the trocar 500. FIGS. 16E and 16F illustrate a third position or configuration of the components after singulation of the second implant has been completed and the second implant has been moved to the "ready-to-fire" position, which is the same position on the trocar 500 as the "ready-to-fire" position that the first implant was in for the initial position or configuration of FIGS. 16A and 16B. In some embodiments, the transition between the second and third position or configuration is performed in a continuous manner (e.g., fluid or uninterrupted) and not considered as separate, discrete steps or configurations from an operator's perspective.

First, the handle 436 of the singulation actuator 214 can receive a force, such as a manual rearward force 600 initiated by a thumb or finger of a user. As the singulation actuator 214 translates proximally (e.g., rearwardly or toward the user, or operator) relative to the frame 310, the distal singulation spring connector 452 translates proximally. As mentioned above, the distal spring portion 442 of the spring 332 is in tension and the proximal spring portion 440 of the spring 332 is also in tension when in a normal resting configuration.

As the proximal spring portion 440 of the spring 332 reaches its minimum tension when the singulation actuator 214 continues to move proximally within the singulation actuator track 424 of the frame 310, the proximal portion 430 of the singulation actuator 214 pushes the singulation arm 334 (e.g., the proximal singulation slot member 456) proximally. Once the proximal singulation slot member 456 slides along one of the platforms 414 (e.g., the first platform 414A) within the singulation frame slot 412, the proximal singulation slot member 456 reaches the proximal end of the platform 414A (see FIGS. 16C and 16D). Due to the force applied by the proximal spring portion 440, the proximal singulation slot member 456 slides downwardly along the tapered rear edge of the platform 414A. The tapered rear edge of the first platform 414A can cause the proximal singulation slot member 456 to slide distally into contact with the distal end portion of the second platform 414B. By releasing the singulation actuator 214, the tension stored in the distal spring portion 442 causes the singulation actuator 214 to return to its original position (e.g., the ready-to-fire position as shown in FIGS. 16E and 16F).

At the same time, when the singulation actuator 214 moves proximally, the distal singulation arm collet holder member 458 moves proximally within the rear collet holder recess 484 and contacts a proximal wall of the rear collet holder recess 484. When the singulation actuator 214 continues to move proximally within the singulation actuator track 424 of the frame 310, the proximal portion 430 of the singulation actuator 214 pushes the singulation arm 334 (e.g., the distal singulation arm collet holder member 458 and the proximal singulation slot member 456) proximally. This causes the collet holder subassembly 358 to slide proximally relative to the insertion tube carrier 354 as the distal singulation arm collet holder member 458 contacts the proximal wall of the rear collet holder recess 484. When the collet holder subassembly 358 slides proximally relative to the insertion tube carrier 354, the splayed distal end 492 of the singulation tube 362 and the singulation tube slot 490 pass over the next implant loaded on the trocar 500 until the distal terminus of the singulation tube 362 is positioned proximal to the proximal end of the next implant (as shown in the close-up detailed view of FIG. 16C showing the distal end of the delivery apparatus 200).

When the singulation actuator 214 is released (e.g., such as when a manual rearward force 600 is removed), the collet holder 360 moves distally a distance until the collet holder notch 488 and the insertion tube carrier notch 473 are in alignment. In this position, the distal end of the singulation tube 362 is positioned immediately adjacent the proximal end of the implant and in a "ready to fire" position (as shown in the close-up detailed view of FIG. 16E showing the distal end of the delivery apparatus 200). The insertion tube 356 is not shown in FIGS. 16A-16E so that internal components can be viewed.

C. Implant Delivery Assemblies

The multiple-implant delivery apparatus 200 can include the implantation actuator assembly 370. The implantation actuator assembly 370 can include the implant delivery actuator 216, an actuator biasing member 372, and an actuator arm 374. As described above, in some embodiments, at least a portion of the implant delivery actuator 216 extends through the opening 212, such as a trigger portion 510 (e.g., button) of the implant delivery actuator 216. The implant delivery actuator 216 can be easily manipulated and/or accessible by the user. In some embodiments, actuation of the implant delivery actuator 216 causes the ejection of an implant (e.g., one implant singulated as a result of actuation of the singulation actuator 214) out of the insertion tube 356 of the delivery apparatus and into a desired first location within the patient's internal eye tissue. The implant delivery actuator 216 interfaces with internal components, such as other components or subassemblies of the multiple-implant delivery apparatus 200 or other components of the actuator assembly 370, to effect delivery of the implants. In some embodiments, the implant delivery actuator 216 is configured to allow for an infinite number of actuations since it does not rely on pre-stored energy.

Figure 17:
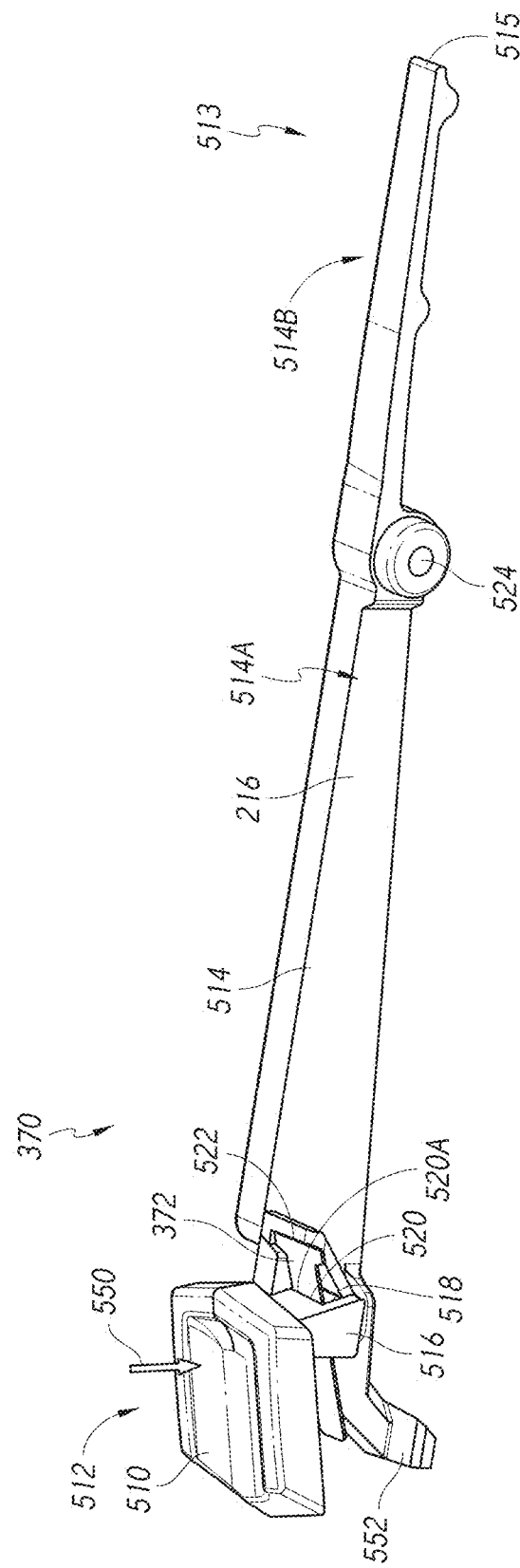
FIG. 17 is perspective view of an embodiment of an actuation assembly of the multiple-implant delivery apparatus of FIG. 2A.

FIG. 17 illustrates an embodiment of the implantation actuator assembly 370 including the implant delivery actuator 216 and the actuator biasing member 372. The implant delivery actuator 216 can include a trigger portion 510 (e.g., button), and a main body portion 514. The trigger portion 510 can be positioned at a distal end portion 512 of the implant delivery actuator 216. The trigger portion 510 can include a recess and/or surface to receive a user's finger or thumb to allow the user to easily find and press on the implant delivery actuator 216. The trigger portion 510 can extend upwardly from the main body portion 514. The trigger portion 510 can extend through the opening 212 to be easily accessed by the user.

In some embodiments, the implant delivery actuator 216 includes a trigger connection portion 516. The trigger connection portion 516 can connect the trigger portion 510 with the main body portion 514. The trigger connection portion 516 can extend laterally from the main body portion 514 and/or upwardly from the main body portion 514. In some embodiments, the trigger connection portion 516 includes a biasing member opening 518. The biasing member opening 518 can be defined by the space formed between a top wall 520 of the opening and a biasing member platform 522 of the implant delivery actuator 216. In some embodiments, the biasing member opening 518 is configured to receive and support the actuator biasing member 372.

Figure 18:
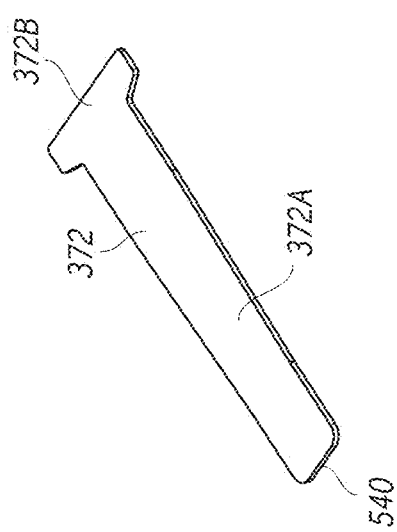
FIG. 18 is a perspective view of an embodiment of an actuation biasing member of the actuation assembly of FIG. 17.

As shown in FIG. 18, the actuator biasing member 372 can be generally T-shaped. For example, the actuator biasing member 372 can have a first portion 372A and a second portion 372B. The first portion 372A can extend in a generally longitudinal direction. The second portion 372B can extend laterally outwardly from either side of the first portion 372A at one end of the first portion 372A. The actuator biasing member 372 can include a spring, such as a leaf spring, a metal, plastic, or other material. The spring can advantageously be pre-loaded so that the spring already has about 30% of the spring force included. In some embodiments, a single spring can be used for both activation and trigger reset. The energy required to effect delivery of an implant may be provided by the actuator biasing member 372 (e.g., spring). The energy is generated in the actuator biasing member 372 (e.g., spring) from the pressing of the trigger portion 510 (e.g., button).

Referring back to FIG. 17, the biasing member 372 can be configured to be positioned within the biasing member opening 518. As shown, the actuator biasing member 372 can be positioned such that at least a portion of the first portion 372A is positioned on one side (e.g., a distal side) of the top wall 520 and at least a portion of the second portion 372B and/or the first portion 372A is positioned on the other side (e.g., a proximal side) of the top wall 520. The portion positioned on the proximal side of the top wall 520 can be configured to be supported at least partially by the biasing member platform 522. In some embodiments, at least a portion of the top wall 520, such as a proximal edge 520A of the top wall 520 exerts a force on the biasing member 372 when assembled.

In some embodiments, the distal portion 512 includes an actuator foot 552 that extends outwardly from the main body portion 514 and is configured to contact a top wall of the lower arm portion 532 of the actuator arm 374, as explained below.

In some embodiments, the main body portion 514 of the implant delivery actuator 216 extends in a proximal direction from the trigger portion 510. The main body portion 514 can have a distal region 514A and a proximal region 514B. The distal region 514A can have a generally straight top surface and a generally tapered bottom surface. The proximal region 514B can have a vertical thickness that is generally thinner than the distal region 514B. The proximal region 514B and the distal region 514A can be connected by an implant delivery actuator pivot member 524. In some embodiments, the connection between the proximal region 514B and the distal region 514B, and/or the shape of the proximal and/or distal regions 514B, 514A is configured to allow the proximal region 514B to flex in use relative to the distal region 514B. The implantation delivery actuator pivot member 524 can extend outwardly from the main body portion 514. The implantation delivery actuator pivot member 524 can be generally circular, among other shapes. The implantation delivery actuator pivot member 524 can be configured to fit within the implant delivery actuator receptacle 408 to allow the implant delivery actuation assembly 370 to pivot in use. As described above, the implant delivery actuator 216 can include a proximal portion 513 having a proximal terminus end 515. The proximal terminus end 515 can be shaped to fit within the implant delivery actuator slot 410 when assembled with the frame 310. Such configurations can help to limit lateral movement of the implant delivery actuator slot 410 when assembled. In some embodiments, when the implant delivery actuator 216 has been actuated, proximal terminus end 515 of the actuator 216 contacts the portion of the frame 310 positioned between the first prong 410A and second prong 410B. As described below, when the user releases the implant delivery actuator 216, the deflection in the proximal region 514B caused by contact with the portion of the frame 310 helps to cause the implant delivery actuator 216 to rotate back into an initial position.

Figure 19:
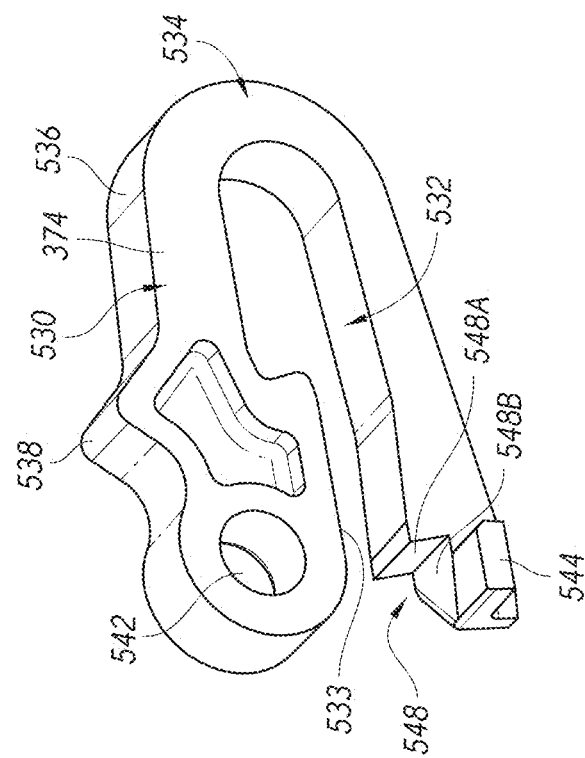
FIG. 19 is a perspective view of an embodiment of an actuator arm of the actuation assembly of FIG. 17.

FIG. 19 illustrates an embodiment of the actuator arm 374. The actuator arm 374 can be generally U-shaped, among other shapes. The actuator arm 374 can form a spring, or other biasing member to bias the delivery implant actuator 216. The actuator arm 374 can include an upper arm portion 530 and a lower arm portion 532 connected by an arced portion 534. The upper arm portion 530 can include a top surface 536 and a bottom surface 533. The top surface 536 can include an upward extension portion 538 that extends upwardly from the top surface 536. The upward extension portion 538 can have a generally triangular shape. The upward extension portion 538 can be configured to contact a distal end portion 540 of the first portion 372A of the actuator biasing member 372 when activating the implantation actuator assembly 370.

In some embodiments, the upper arm portion 530 includes an actuator arm connection opening 542. The actuator arm connection opening 542 passes through a width of the actuator arm 374. The actuator arm connection opening 542 is configured to receive the actuator arm attachment member 418 when the actuator arm 374 is assembled with the frame 310. In some embodiments, the actuator arm attachment member 418 is sized and/or configured to snap to or otherwise reside within at least a portion of the actuator arm 374, such as the actuator arm connection opening 542. As explained in more detail below, the actuator arm 374 can be configured to pivot about the actuator arm attachment member 418.

In some embodiments, the lower arm portion 532 includes an actuator arm protrusion member 544. The actuator arm protrusion member 544 can extend outwardly from the lower arm portion 532. The actuator arm protrusion member 544 can be generally rectangular shaped. The actuator arm protrusion member 544 can be positioned generally above the central collet holder recess 482 in an initial position when the actuator arm 374 is assembled with the frame 310. When assembled to the frame 310, the actuator arm protrusion member 544 can contact the actuator arm protrusion platform 422. In some embodiments, the actuator arm protrusion platform 422 is adapted to support at least a portion of the actuator arm 374.

In some embodiments, the lower arm portion 532 includes a stepped region 548 at the distal end portion of the lower arm portion 532. For example, the stepped region 548 includes a distal facing side 548A and an upwardly facing side 548B. The upwardly facing side 548B is generally aligned with a top surface of the actuator arm protrusion member 544. The distal facing side 548A is configured to contact a proximal end portion of the platform 422 of the frame 310 when assembled.

As mentioned above, the singulation actuator 214 facilitates the user-initiated singulation, isolation, and/or selection of one of the multiple implants for delivery one at a time. The singulation actuator 214 interfaces with internal components (described above) to effect singulation. After singulation, the next implant may be actuated for delivery.

Figure 20A:
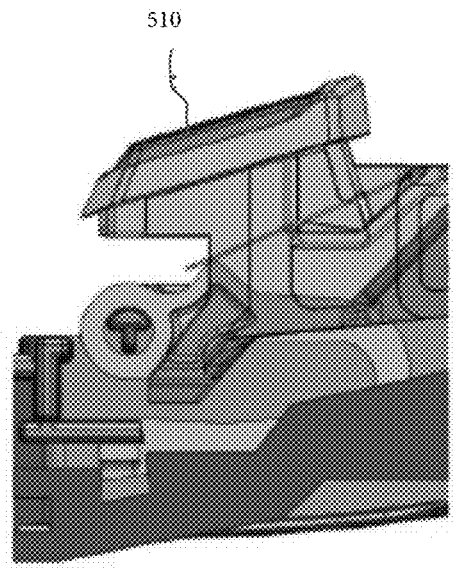
FIGS. 20A-20D are partial cross-section views illustrating components of the multiple-implant delivery apparatus of FIG. 2A at various stages of an implant delivery cycle.

FIGS. 20A-20D illustrate an embodiment of how various components of the multiple-implant delivery apparatus 200 interact to effect delivery of an implant. The same process can occur for delivery of any or all of the implants. FIG. 20A illustrates the components prior to initiation of implant delivery when the components are in an initial resting configuration.

Figure 20B:
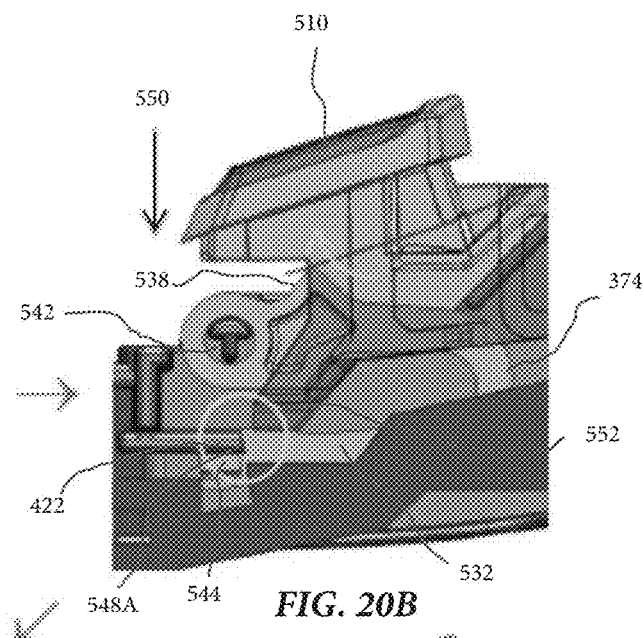

As mentioned above, the implant delivery actuation assembly 370 is configured to allow for an infinite (e.g., unlimited) number of actuations. With reference to FIG. 20B, when the implant delivery actuator trigger portion 510 receives a downward force 550 (e.g., press by a user's thumb or finger), the implantation delivery assembly (e.g., the implant delivery actuator 216 and the actuator biasing member 372) attempts to rotate about the pivotable connection between the implant delivery actuator 216 (the implant delivery actuator pivot member 524) and the frame 310 at the implant delivery actuator receptacle 408 (shown best in FIG. 7A). As mentioned above, when this occurs, the proximal region 514B (shown best in FIG. 17) of the implant delivery actuator 216 deflects slightly when the proximal terminus end 515 (shown best in FIG. 17) of the implant delivery actuator 216 presses against the portion of the frame 310 positioned between the first prong 410A and second prong 410B (shown best in FIG. 7A).

In some embodiments, downward movement of the trigger portion 510 causes at least a portion of the distal end portion 540 of the first portion 372A (e.g., distal terminus or a portion spaced one or two millimeters away from the distal terminus) of the actuator biasing member 372 (shown best in FIG. 18) to contact and/or press down on the upwardly extending portion 538 of the actuator arm 374. In some embodiments, continued downward movement of the implant delivery actuator trigger portion 510 causes the actuator lever, or foot, 552 to contact a top, or upper, wall of the lower arm portion 532 of the actuator arm 374. Such contact can cause the implant actuator arm protrusion member 544 to slide into the central collet holder recess 482 and the distal facing side 548A of the stepped region 548 to contact a proximal end portion of the platform 422 of the frame 310.

Figure 20C:
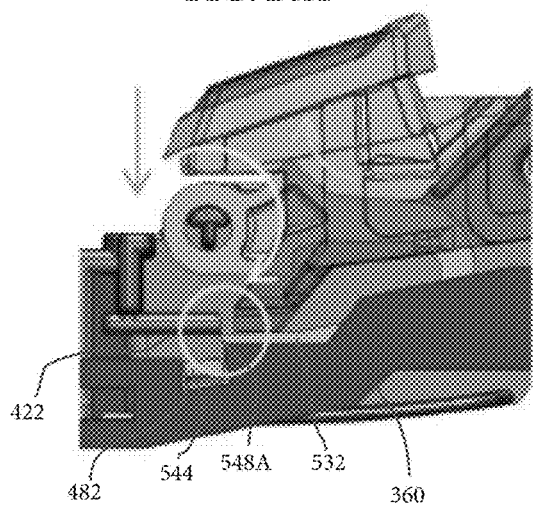
Figure 20D:
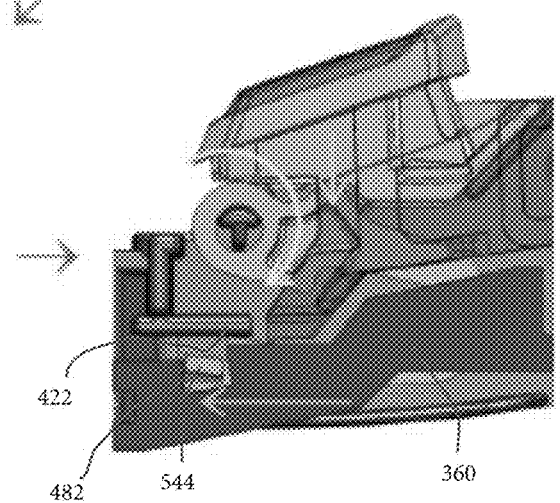

As shown in FIG. 20B, the actuator arm 374 is unable to rotate due to the mating of the sear surfaces between the proximal end portion of the platform 422 of the frame 310 and the distal facing side 548A of the stepped region 548 at the distal end portion of the lower arm portion 532 of the actuator arm 374. With reference to FIG. 20C, in some embodiments, continued downward movement of the trigger portion 510 generates enough pressure on the lower arm portion 532 of the actuator arm 374 to cause it to flex, which causes the distal facing side 548A of the lower arm portion 532 of the actuator arm 374 to slide downwardly along the proximal end portion of the platform 522 until the sear surfaces disengage, thereby allowing the actuator arm 374 to rotate about the pivotable connection between the actuator arm 374 (the actuator arm connection opening 542) and the frame 310 at the actuator arm attachment member 418. Once the distal facing side 548A passes the proximal end portion of the platform 522, the spring force in the biasing member 372 that is captured and converted to energy from the downward movement of the trigger portion 510 causes the implantation actuator arm protrusion member 544 to move forward a short distance, contacting a proximal side wall of the central collet holder recess 482 (see FIG. 20D). This causes distal movement of the collet holder 360, causing the singulation tube 362 to move distally and push an implant towards the end of the trocar 500 to deliver the implant into the proper position within eye tissue. At this stage, the collet holder notch 488 is positioned distally of the carrier notch 473 (not shown). The trigger portion 510 can be actuated an infinite (e.g., unlimited) number of times to push the implant into the proper position in the eye since the mechanism does not rely on a pre-stored, limited supply of energy. When the trigger portion 510 is released, the proximal region 514B of the implant delivery actuator 216 unbends and the actuator foot 552 lifts a bottom surface 533 of the upper arm portion 530 of the actuator arm 374 (see FIG. 19), rotating the actuator arm 374 into the initial position or configuration and allowing the collet holder 360 to translate proximally into the initial position or configuration. At this point, the collet holder notch 488 and the carrier notch 473 are aligned again. Accordingly, no collet return spring is required to reset the collet holder 360 to the initial position or configuration. The collet holder 360 is held in a forward position until the operator releases the trigger portion 510; it does not automatically return to the initial position or configuration.

IV. Example Method of Use of Multiple-Implant Delivery Apparatus

Figure 21A:
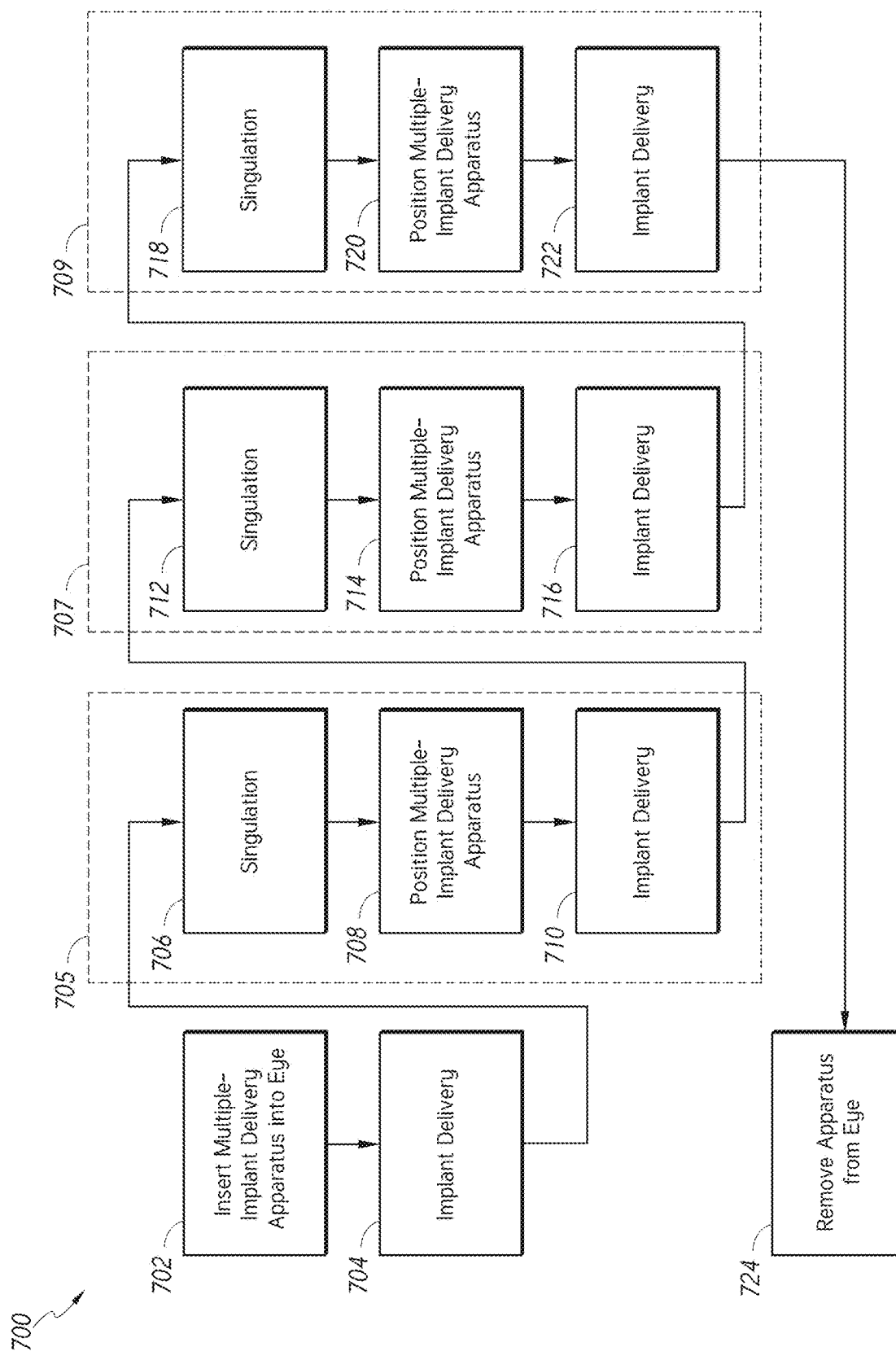
FIG. 21A is an example method of using the implant delivery apparatus.

FIG. 21A illustrates an example method 700 of operating the multiple-implant delivery apparatus 200. At block 702, a user or operator, such as a doctor or clinician, can insert a portion of the multiple-implant delivery apparatus into the patient's eye and advance it to a location adjacent a desired implantation site. The user can grip the multiple-implant delivery apparatus 200 and rotate their hand so that their elbow is positioned by a side of the user's body. In some embodiments, the apparatus is rotated significantly in the user's hand (e.g., rotated right between 10 and 90 degrees with respect to a central longitudinal axis of the apparatus 200).

Figure 21B:
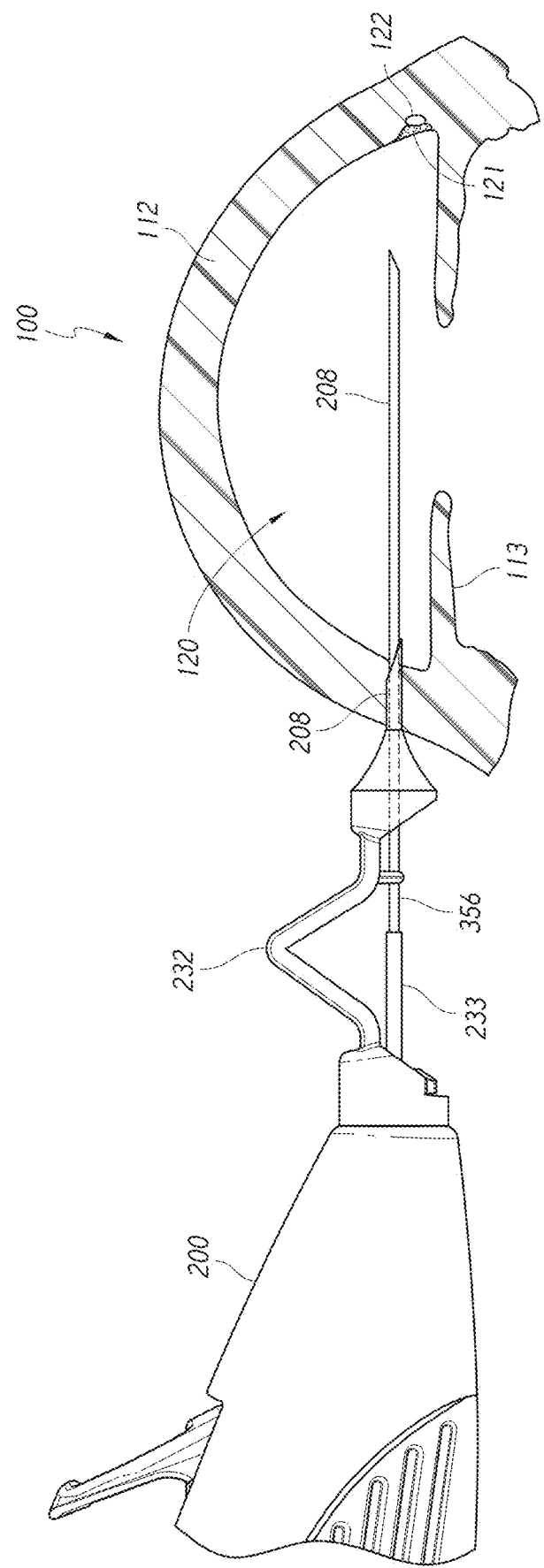
FIG. 21B is a schematic and partial sectional view of a portion of an eye illustrating insertion of the multiple-implant delivery apparatus within the eye.

FIG. 21B illustrates the insertion of the multiple-implant delivery apparatus 200 within the eye 100. In one embodiment, a small self-sealing incision or opening is made in the cornea 112 at or near the limbus or in other external surface area of the eye. In certain embodiments, the introducer assembly 201 is inserted from a site transocularly situated from the desired implantation site, at block 702. The distal introducer tip 208 is then advanced through the incision or opening across the anterior chamber 120 toward the desired implantation site within the trabecular meshwork 121 (e.g., under gonioscopic guidance). Although FIG. 21B illustrates an ab interno method of insertion, it should be appreciated that ab externo methods of insertion are also contemplated.

Referring back to FIG. 21A, at block 704, upon reaching the desired implantation site adjacent or in the trabecular meshwork 121, the user presses the implant delivery actuator 216 to deliver the pre-loaded implant (e.g., a first pre-loaded implant). The advancement position can be determined by visualization (e.g., imaging or fiberoptic) or tactile methods or by depth markings or a depth stop. At this point, the first implant is ready to be delivered to the desired implantation site upon depression of the implant delivery actuator 216 by the user. The implant is delivered according to methods described above.

Optionally, the operator can deliver a second implant according to a method 705 of delivering the second implant. At block 706, the operator can manually actuate the singulation actuator 214 according to methods described above to select the second implant 901B. At block 708, the operator can remove the trocar 500 from the first implantation site in the internal eye tissue. The multiple-implant delivery apparatus 200 can then be moved to facilitate delivery to a second desired implantation site for the second implant 901B within the same eye by simply withdrawing the apparatus 200 within the eye and repositioning and/or reorienting the apparatus 200 (e.g., rotating the operator's hand to rotate the apparatus 200 back left to a straight configuration with elbow against the operator's side). Thus, the multiple-implant delivery apparatus 200 can advantageously deliver two ocular implants at multiple locations within the eye without necessitating removal of the apparatus 200 from the eye to reload another implant. Once the multiple-implant delivery apparatus 200 is positioned in the correct position, the implant can be delivered at block 710 by actuating the implant delivery actuator 216 according to methods described above. In some embodiments, the implant delivery actuator 216 is configured to allow for an infinite number of actuations of a single implant until the second implant 901B is properly positioned within the eye.

Optionally, the operator can deliver a third implant according to a method 707 of delivering the third implant. At block 712, the operator can manually actuate the singulation actuator 214 according to methods described above to select the third implant 901C. At block 714, the operator can remove the trocar 500 from the second implantation site in the internal eye tissue. The multiple-implant delivery apparatus 200 can then be moved to facilitate delivery to a third desired implantation site for the third implant 901C within the same eye by simply withdrawing the apparatus within the eye and repositioning and/or reorienting the apparatus 200 (e.g., operatory lifting his or her elbow outwardly away from the operator's side and then rotating the operator's hand to the left by between 10 and 90 degrees to rotate the apparatus 200 left). Thus, the multiple-implant delivery apparatus 200 can advantageously deliver three ocular implants at multiple locations within the eye without necessitating removal of the apparatus from the eye to reload another implant. Once the multiple-implant delivery apparatus 200 is positioned in the correct position, the implant can be delivered at block 716 by actuating the implant delivery actuator 216 according to methods described above. In some embodiments, the implant delivery actuator 216 is configured to allow for an infinite number of actuations until the third implant 901C is properly positioned within the eye.

Optionally, the operator can deliver a fourth implant according to a method 709 of delivering the fourth implant. At block 718, the operator can manually actuate the singulation actuator 214 according to methods described above to select the fourth implant 901D. At block 720, the operator can remove the trocar 500 from the third implantation site in the internal eye tissue. The multiple-implant delivery apparatus 200 can then be moved to a fourth desired implantation site for delivery of the fourth implant 901D within the same eye by simply withdrawing the apparatus within the eye and repositioning and/or reorienting the apparatus 200. Thus, the multiple-implant delivery apparatus 200 can advantageously deliver four ocular implants at multiple locations within the eye without necessitating removal of the apparatus from the eye to reload another implant. Once the fourth implant 901D is selected, the singulation actuator 214 includes a stop to prevent the operator from pulling back on the actuator to select another implant. Once the multiple-implant delivery apparatus 200 is positioned in the correct position, the fourth implant can be delivered at block 722 by actuating the implant delivery actuator 216 according to methods described above. In some embodiments, the implant delivery actuator 216 is configured to allow for an infinite number of actuations until the fourth implant is properly positioned within the eye.

At block 724, the multiple-implant delivery apparatus 200 can be removed from the eye (after delivery of one implant, two implants, three implants or four implants). In some embodiments, the singulation and positioning steps can be reversed (i.e., singulation can be performed after relocating the apparatus to a location adjacent a subsequent desired implantation site). In accordance with several embodiments, every successive implantation appears (e.g., location of implant in visualization slot) and feels the same to the clinician using the multiple-implant delivery apparatus 200 regardless of how many implants are included in the apparatus or actually implanted because of the manual actuation of the singulation.

V. Example Implants and Implantation Locations

Figure 22:
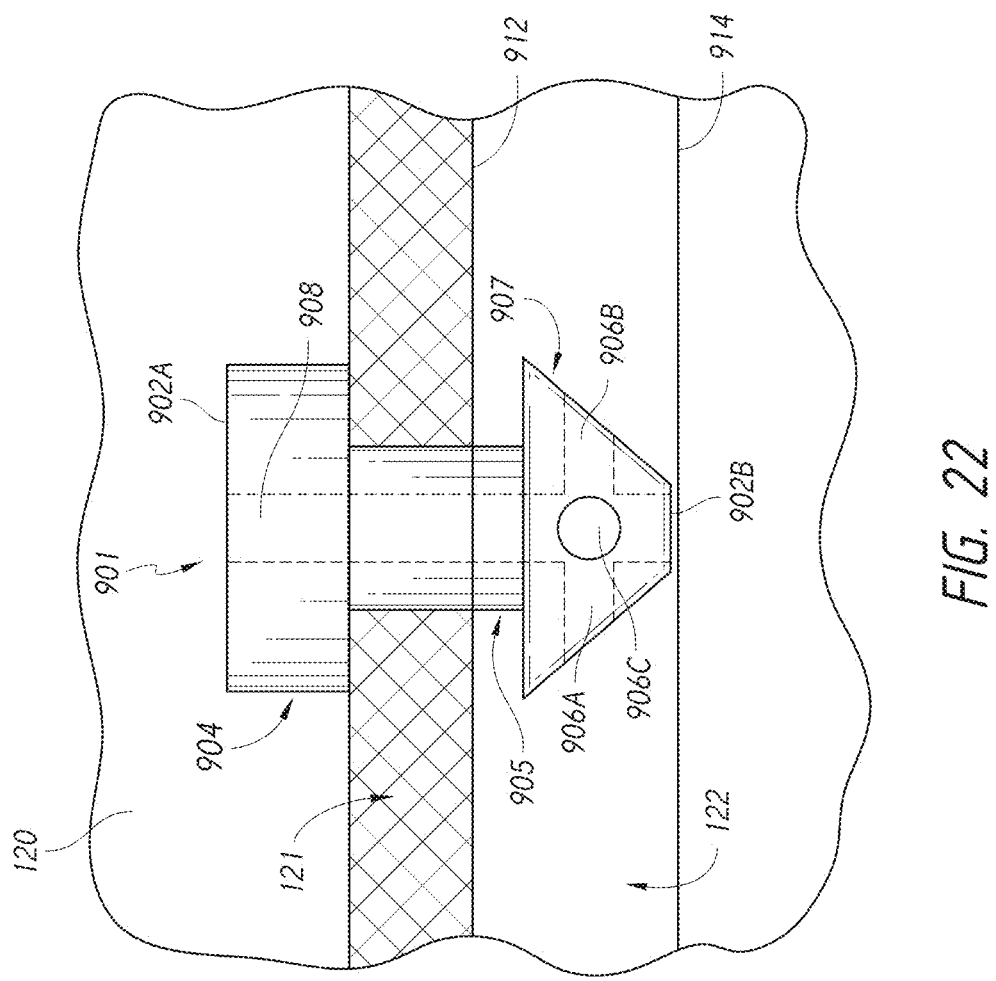
FIG. 22 is an enlarged schematic and partial sectional view of Schlemm's canal and the trabecular meshwork of an eye illustrating the position and operation of an ocular implant delivered by the multiple-implant delivery apparatus of FIG. 2A.

FIG. 22 illustrates an example implant implanted in the eye. The aqueous humor flows from the anterior chamber 120, through an inlet lumen 908, and then out through one, two or more outlet ports 906 (e.g., four outlet ports 906A, 906B, 906C and a fourth outlet port not seen opposite outlet port 906C) to be directed in both directions along Schlemm's canal 122. In some embodiments, the implant 901 includes an axial outlet port in communication with the inlet lumen 908 that is located along a distal end 902B to potentially direct flow in an axial direction if the distal end 902B is not obstructed. Alternatively, flow could be directed in only one direction through a single outlet port 906A or flow could be directed in two directions through two outlet ports 906A and 906B, depending on a rotational position of the implant 901 within Schlemm's canal or other physiologic outflow pathway upon implantation. More than two outlet ports 906 can be efficaciously used, as needed or desired to increase outflow or reduce the potential for obstruction of the outlet ports to flow within Schlemm's canal 122. For example, in some embodiments, four outlet ports can be oriented at 90 degrees with respect to the inlet lumen 908 and with respect to adjacent outlet ports such that an outlet port is positioned at every 90 degree rotation of the implant 901. The use of four or more outlet ports may increase the likelihood that at least two outlet ports are oriented to facilitate flow within Schlemm's canal 122 without rotational adjustment or orientation after delivery or implantation. The proximal end of the distal portion 907 can abut the inner wall 912 of Schlemm's canal 122, and the distal end of the proximal portion 904 can abut the trabecular meshwork 121 upon delivery. Accordingly, the implant 901 can be secured in place by the proximal and distal portions of the implant 901 abutting opposite sides of the trabecular meshwork 121. In some embodiments, the distal end 902B is in contact with the outer wall 914 of Schlemm's canal 122. As described above, the implant delivery actuator 216 of the multiple-implant delivery apparatus 200 may be actuated multiple times until the implant 901 is in the desired final implantation location. In alternative embodiments, the implant 901 can be implanted such that an outlet of the implant 901 is positioned in a physiologic outflow pathway other than Schlemm's canal 122.

At least some of the disclosed embodiments include implants that provide a fluid flow path for conducting aqueous humor from the anterior chamber of an eye to a physiologic outflow pathway to reduce intraocular pressure, preferably below episcleral venous pressure without hypotony. The implants can have an inflow portion and an outflow portion. The outflow portion of the implant preferably is disposed at or near a distal end of the implant. When the implant is implanted, the inflow portion may be sized and configured to reside in the anterior chamber of the eye and the outflow portion may be sized and configured to reside in a physiologic outflow pathway. In some embodiments, the outflow portion may be sized and configured to reside in Schlemm's canal. In other embodiments, the outflow portion may be sized and configured to reside at least partially in the supraciliary region of the uveoscleral outflow pathway or the suprachoroidal space.

In some embodiments, the implants have a generally sharpened forward end and are self-trephinating, i.e., self-penetrating, so as to pass through tissue without pre-forming an incision, hole or aperture. The sharpened forward end can be, for example, conical or tapered. The tip can be sufficiently sharp to pierce eye tissue. The tip also can be sufficiently blunt so as not to substantially penetrate eye tissue. The taper angle of the sharpened end can be, for example, about 30°±15° in some embodiments. The radius of the tip can be about 70 to about 200 microns. Where an outlet opening is formed at the distal end of the implant, the distal portion can gradually increase in cross-sectional size in the proximal direction, preferably at a generally constant taper or radius or in a parabolic manner. In some embodiments including an outlet opening at the distal end, the diameter of the axial outlet opening formed at the distal end may be between 40 and 200 microns (e.g., 40 microns, 60 microns, 80 microns, 100 microns, 120 microns, 120 microns, 140 microns, 160 microns, 180 microns). Additionally, in such embodiments, an annulus may be formed between an edge defined by the outer circumference of the axial outlet opening and an edge defined by the intersection of the distal tip surface and the conical or tapered section of the distal portion. The width of this annulus may advantageously be sufficiently small such that, after the trocar has created a pilot hole in eye tissue (e.g., trabecular meshwork), the distal portion can expand eye tissue surrounding the pilot hole as the implant is advanced into the eye tissue. The eye tissue can then retract around an intermediate portion of the eye implant. If the annulus width is not sufficiently small, the distal portion may potentially push, rather than expand, the eye tissue.

The implants may be of varied lengths and sizes to optimize flows. In some embodiments, the implant has sufficient length such that the outflow portion resides in a physiologic outflow pathway and the inflow portion is exposed to the anterior chamber. In some embodiments, the length of the implant from the portion residing in the anterior chamber to the portion residing in the physiologic outflow pathway may be about 0.001 mm to about 5 mm, about 0.01 mm to about 1 mm, about 0.1 mm to about 0.5 mm, or overlapping ranges thereof. In some embodiments, the length of the implant is about 0.05, 0.10, 0.15, 0.20, 0.25, 0.30, 0.35, 0.40, 0.45, or 0.50 mm.

The implant is preferably made of one or more biocompatible materials. Suitable biocompatible materials include, for example, polypropylene, polyimide, glass, nitinol, polyvinyl alcohol, polyvinyl pyrolidone, collagen, chemically-treated collagen, polyethersulfone (PES), poly(styrene-isobutyl-styrene), Pebax, acrylic, polyolefin, polysilicon, polypropylene, hydroxyapetite, titanium, gold, silver, platinum, other metals, ceramics, plastics and a mixture thereof. The implants can be manufactured by sintering, micro machining, laser machining, and/or electrical discharge machining. However, other suitable manufacturing methods can be used.

If desired, more than one implant of the same or different type may be implanted. Additionally, implantation may be performed in combination with other surgical procedures, such as cataract surgery. All or a portion of the implant may be coated, e.g. with heparin, preferably in the flow path, to reduce blood thrombosis or tissue restenosis. In accordance with several embodiments, the same multiple-implant delivery apparatus 200 may be used to deliver different sizes or types of implants without having to reconfigure or readapt the apparatus. For example, implants with different maximum outer cross-sectional dimensions may be used in the multiple-implant delivery apparatus. The different sizes or types of implants may be implanted during a single procedure at a single time or in separate procedures at separate times. For example, if desired, a multiplicity of implants having different flow capacities and/or sizes may be implanted.

Although the multiple-implant delivery apparatus 200 has been described herein with respect to delivery of ocular implants within internal eye tissue, the multiple-implant delivery apparatus 200 could be used or adapted to singulate and deliver multiples of other types of implants within the body. Examples of the ocular implants that could be used with the multiple-implant delivery apparatus 200 include implants, stents, or shunts of the shape, size and scale of those described and illustrated in U.S. Pat. Nos. 7,135,009; 9,301,875; 7,867,186; and U.S. Publication No. 2014/0276332.

VI. Kits and Additional Language

According to some embodiments, a kit (e.g., system or collection of items for a common purpose) for addressing ocular disorders is provided. The tem "kit" as used herein should be given its ordinary meaning and should include any system, grouping and/or collection of devices, systems, components, features, materials and/or the like provided for a common goal. In one embodiment, the kit comprises one or more of the following: a delivery apparatus (such as the multiple-implant delivery apparatus 200 described herein), a plurality of drainage implants (such as the drainage implants described herein), an incising member, and a sensor (such as a pressure sensor, an intraocular pressure sensor, an analyte sensor, a glucose sensor, or any other sensor configured for placement within an eye). In some embodiments, the drainage implants are pre-loaded within or on the delivery apparatus during manufacture and assembly prior to shipping. In other embodiments, the drainage implants are not pre-loaded. The kit can further comprise instructions for using the various devices, components and/or other features of the kit for a particular procedure or treatment protocol. For example, such instructions for use can include details regarding the order in which the devices, systems or other components are used, the duration of use and/or the like.

While certain embodiments of the disclosure have been described, these embodiments have been presented by way of example only, and are not intended to limit the scope of the disclosure. Indeed, the novel methods, systems, and devices described herein may be embodied in a variety of other forms. For example, embodiments of one illustrated or described implant can be combined with embodiments of another illustrated or described implant. Moreover, the implants described above can be utilized for other purposes. For example, the implants can be used to drain fluid from the anterior chamber to other locations of the eye or outside the eye. In some embodiments, the systems comprise various features that are present as single features (as opposed to multiple features). Conversely, various features that are described in the context of a single implementation can also be implemented in multiple implementations separately or in any suitable subcombination. Multiple features or components are provided in some embodiments. Some embodiments have been described in connection with the accompanying drawings. However, it should be understood that the figures are not necessarily drawn to scale. Distances, angles, etc. are merely illustrative and do not necessarily bear an exact relationship to actual dimensions and layout of the devices illustrated. Components can be added, removed, and/or rearranged. Furthermore, various omissions, substitutions and changes in the form of the methods, systems, and devices described herein may be made without departing from the spirit of the disclosure.

Conditional language, for example, among others, "can," "could," "might," or "may," unless specifically stated otherwise, or otherwise understood within the context as used, is generally intended to convey that certain embodiments include, while other embodiments do not include, certain features, elements and/or steps. Thus, such conditional language is not generally intended to imply that features, elements and/or steps are in any way required for one or more embodiments or that one or more embodiments necessarily include logic for deciding, with or without user input or prompting, whether these features, elements and/or steps are included or are to be performed in any particular embodiment. The section headings used herein are merely provided to enhance readability and are not intended to limit the scope of the embodiments disclosed in a particular section to the features or elements disclosed in that section. The terms "comprising," "including,", "having," and the like are synonymous and are used inclusively, in an open-ended fashion, and do not exclude additional elements, features, acts, operations, and so forth. Also, the term "or" is used in its inclusive sense (and not in its exclusive sense) so that when used, for example, to connect a list of elements, the term "or" means one, some, or all of the elements in the list.

Any methods disclosed herein need not be performed in the order recited. The methods disclosed herein include certain actions taken by a practitioner; however, they can also include any third-party instruction of those actions, either expressly or by implication. For example, actions such as "advancing a delivery apparatus" include "instructing advancing a delivery apparatus." The ranges disclosed herein also encompass any and all overlap, sub-ranges, and combinations thereof. Language such as "up to," "at least," "greater than," "less than," "between," and the like includes the number recited. Numbers preceded by a term such as "about" or "approximately" include the recited numbers or an amount that is within less than or equal to 10% of the stated amount. For example, "about 200 microns" includes "200 microns." Terms or phrases preceded by a term such as "substantially" or "generally" include the recited term or phrase. The term "generally" as used herein represents a value, amount, or characteristic that predominantly includes or tends toward a particular value, amount, or characteristic. For example, "substantially V-shaped" includes "V-shaped" and "generally rounded" includes "rounded."

For purposes of this disclosure, certain aspects, advantages, and novel features are described herein. Not necessarily all such advantages may be achieved in accordance with any particular embodiment. Thus, for example, those skilled in the art will recognize that the disclosure may be embodied or carried out in a manner that achieves one advantage or a group of advantages as taught herein without necessarily achieving other advantages as may be taught or suggested herein.

What is claimed is:

1. An implant delivery apparatus configured to deliver a plurality of implants for treating an ocular disorder, the apparatus comprising:
   an external housing comprising:
      an opening;
      a trigger button configured to be actuated by a user extending out of the opening to effect implant delivery;
      a singulation portion comprising a singulation actuator extending out of the opening, the singulation actuator being configured to be manually actuated by the user so as to singulate a respective one of the plurality of implants for delivery upon each manual actuation of the singulation actuator such that the plurality of implants are delivered one at a time;

an introducer tube extending from the external housing at an angle offset from a longitudinal axis of the implant delivery apparatus; and a trocar configured to extend within and through the introducer tube, wherein the plurality of implants are configured to be positioned and advanced along the trocar.

2. The implant delivery apparatus of claim 1, further comprising:

an auto-retracting introducer assembly configured to surround at least a portion of the introducer tube, the introducer assembly comprising a flexible proximal retraction member that is configured to buckle along its length and a distal introducer tip that is configured to be inserted through an opening in eye tissue to facilitate insertion of the introducer tube within an eye, wherein a proximal end of the proximal retraction member is coupled to a distal end portion of the external housing, and wherein a distal end of the proximal retraction member comprises an interface component sized and shaped to interface with a boundary of the opening in the eye tissue and to prevent continued advancement of the distal introducer tip within the eye such that the proximal retraction member buckles along its length as the introducer tube is advanced further within the eye through the opening in the eye tissue.

3. The implant delivery apparatus of claim 2, wherein the interface component is generally cone-shaped.

4. The implant delivery apparatus of claim 2, wherein the proximal retraction member comprises multiple openings positioned along its length at spaced-apart locations designed to facilitate bending of the proximal retraction member in a desired bending configuration.

5. The implant delivery apparatus of claim 1, wherein each manual actuation of the singulation actuator causes the respective one of the plurality of implants to be positioned in a same "ready-to-fire position" along the trocar.

6. The implant delivery apparatus of claim 5, further comprising a singulation tube operably coupled to the singulation actuator, wherein the singulation tube is configured to engage a proximal end of one of the plurality of implants and advance the respective implant to the "ready-to-fire position" along the trocar upon the manual actuation of the singulation actuator.

7. The implant delivery apparatus of claim 1, wherein the trigger button is operably coupled to an actuation biasing member that is configured to generate an implantation impulse sufficient to effect implant delivery by capturing and converting energy used to press the trigger button without use of pre-stored energy that is stored prior to pressing of the trigger button.

8. The implant delivery apparatus of claim 7, wherein the actuation biasing member comprises a leaf spring.

9. The implant delivery apparatus of claim 1, wherein the plurality of implants comprises at least three implants.

10. The implant delivery apparatus of claim 1, wherein the trocar comprises a plurality of separation regions positioned at spaced-apart locations along a length of the trocar, the separation regions configured to separate the plurality of implants from each other until the singulation actuator of the singulation portion interacts with a respective one of the plurality of implants upon manual actuation of the singulation actuator by the user.

11. The implant delivery apparatus of claim 10, wherein the separation regions comprise splayed trocar regions comprising a plurality of slits around a circumference of the trocar at the plurality of spaced-apart locations, and wherein the splayed trocar regions comprise a heat set shape such that in a resting configuration, the plurality of slits are splayed outward such that a cross-sectional dimension of the trocar along the splayed trocar regions is larger than a cross-sectional dimension of the trocar between the splayed trocar regions.

12. The implant delivery apparatus of claim 1, wherein the angle is between 5 and 12 degrees.

13. An implant delivery apparatus configured to deliver a plurality of implants for treating an ocular disorder, the apparatus comprising:

an external housing comprising:
an opening; an
a trigger button configured to be actuated by a user extending out of the opening,
wherein the trigger button comprises an actuator that is configured to be manually actuated by the user to effect implant delivery;
an actuation biasing member operably coupled to the trigger button such that, upon pressing of the trigger button, energy sufficient to deliver a respective implant of the plurality of implants is generated by the actuation biasing member without use of pre-stored energy that is stored prior to pressing of the trigger button; and a trocar configured to extend from a distal end of the external housing, wherein the plurality of implants are configured to be positioned and advanced along the trocar.

14. The implant delivery apparatus of claim 13, wherein the actuation biasing member comprises a leaf spring.

15. The implant delivery apparatus of claim 14, wherein the leaf spring is configured to bend upon pressing of the trigger button by the user, thereby generating the energy sufficient to effect delivery of the respective implant.

16. The implant delivery apparatus of claim 13, further comprising a singulation handle extending out of the opening, wherein the singulation handle is configured to be manually actuated by the user so as to facilitate on-demand manual singulation to effect selection of one of the plurality of implants for delivery one at a time.

17. The implant delivery apparatus of claim 13, wherein the trocar comprises multiple singulation regions spaced apart along a length of the trocar, the singulation regions being configured to facilitate mechanical separation of the plurality of implants from each other.

18. The implant delivery apparatus of claim 17, wherein the singulation regions comprise splayed regions formed by slits in the trocar at each of the singulation regions.

19. An implant delivery apparatus configured to deliver a plurality of implants for treating an ocular disorder, the apparatus comprising:

an external housing comprising:
an opening;
a trigger button extending out of the opening, the trigger button configured to be manually actuated by a user to effect implant delivery;
a singulation handle extending out of the opening, the singulation handle configured to be manually actuated by the user so as to facilitate on-demand manual singulation to effect selection of a respective one of the plurality of implants for delivery of the plurality of implants one at a time; and a trocar configured to extend from a distal end of the external housing, wherein the plurality of implants are configured to be positioned and advanced along the trocar, wherein the trocar comprises a plurality of separation regions formed by slits along a length of the trocar at spaced-apart locations along the length of the trocar, the separation regions configured to mechanically separate the plurality of implants from each other until a singulation actuator operably coupled to the singulation handle interacts with the respective one of the plurality of implants upon manual actuation of the singulation handle by the user.

20. The apparatus of claim 19, wherein the separation regions comprise splayed regions formed by slits in the trocar at each of the spaced-apart locations along the length of the trocar, wherein the splayed regions comprise a heat set shape such that, in a resting configuration, the slits are splayed outward such that a cross-sectional dimension of the trocar along the splayed regions is larger than a cross-sectional dimension of the trocar between the splayed regions.

* * * * *